United States Patent [19]
Cheshire et al.

[11] Patent Number: 5,977,105
[45] Date of Patent: Nov. 2, 1999

[54] COMPOUNDS

[75] Inventors: David Cheshire, Chilwell; David Cladingboel, Mountsorrel; David Hardern, Sutton Bonington; Michael Stocks, Long Eaton, all of United Kingdom

[73] Assignee: Astra Pharmaeuticals Ltd., Kings Langley, United Kingdom

[21] Appl. No.: 08/793,918

[22] PCT Filed: Dec. 4, 1996

[86] PCT No.: PCT/SE96/01595

§ 371 Date: Mar. 3, 1997

§ 102(e) Date: Mar. 3, 1997

[87] PCT Pub. No.: WO97/20815

PCT Pub. Date: Jun. 12, 1997

[30] Foreign Application Priority Data

| Dec. 6, 1995 | [GB] | United Kingdom | .................... | 9524920 |
| May 4, 1996 | [GB] | United Kingdom | .................... | 9609403 |
| Oct. 22, 1996 | [GB] | United Kingdom | .................... | 9622412 |

[51] Int. Cl.⁶ ........................ A01N 43/66; C07D 211/70; C07D 211/72
[52] U.S. Cl. ........................... 514/241; 546/340; 546/344
[58] Field of Search ............................ 514/241; 546/340, 546/344

[56] References Cited

FOREIGN PATENT DOCUMENTS

| 0 264 114 A1 | 4/1988 | European Pat. Off. . |
| 0 267 439 | 5/1988 | European Pat. Off. . |
| 0 267 439 A2 | 5/1988 | European Pat. Off. . |
| 0 391 624 | 10/1990 | European Pat. Off. . |
| 90/12006 | 10/1990 | WIPO . |

*Primary Examiner*—D. Margaret Mach
*Attorney, Agent, or Firm*—Nixon & Vanderhye

[57] ABSTRACT

A compound of formula I,

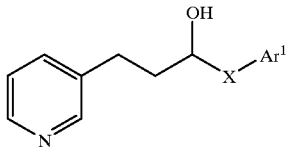

I wherein—

X represents $(CH_2)_nO$, $(CH_2)_nS$ or $C_2$ alkylene;

n represents 1 or 2;

$Ar^1$ represents indanyl, tetrahydronaphthyl, naphthyl or phenyl, which latter two groups may be substituted by one or more substituents selected from chloro, fluoro, $OR^1$, $O(CH_2)_mCONR^{20}R^{21}$, $C(O)R^2$, $C_{1-6}$ alkyl (optionally substituted by one or more fluorine atoms), pyridyl, thiazinyl, phenyl or $C_{7-9}$ alkylphenyl which latter two groups are optionally substituted by one or more substituent selected from halo, nitro, $OR^3$, $C_{1-6}$ alkyl (optionally substituted by one or more fluorine atoms), $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$ and $SO_2NR^{17}R^{18}$;

m represents an integer 1 to 3;

$R^1$, $R^2$ and $R^3$ independently represent H, $C_{1-10}$ alkyl (optionally substituted by one or more fluorine atoms), $C_{7-9}$ alkylphenyl or phenyl, which latter group is optionally substituted by hydroxy; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently represent H, $C_{1-6}$ alkyl (optionally substituted by one or more fluorine atoms) or phenyl;

in which any alkyl group present may be interrupted by one or more oxygen atoms;

provided that when X represents $CH_2CH_2$, $Ar^1$ may not represent phenyl or phenyl substituted with one or more substituents $OR^1$, in which $R^1$ represents $C_{1-10}$ alkyl;

or a pharmaceutically acceptable derivative thereof, may be used for the treatment of a reversible obstructive airways disease or allergic conditions of the skin, nose and eye.

14 Claims, No Drawings

COMPOUNDS

This application is a 371 of PCT/SE96/01595, filed Dec. 4, 1996.

This invention relates to pharmaceutically useful compounds, their use as medicaments, pharmaceutical formulations including them and methods for their preparation.

European Patent Applications EP-A-0 264 114 and EP-A-0 267 439 disclose certain phenylalkyl- and phenylalkoxypyridine alkanol derivatives and their use as platelet-activating factor (PAF) antagonists. Example 11 of EP-A-0 267 439 (G. D. Searle & Co.) shows α-[3-(4-methoxyphenyl)ethyl]-3-pyridinepropanol:

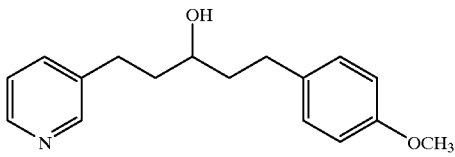

According to the present invention, there is provided a compound of formula I,

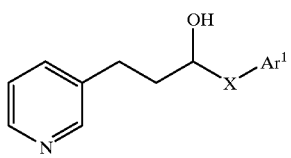

I wherein—

X represents $(CH_2)_nO$, $(CH_2)_nS$ or $C_2$ alkylene;

n represents 1 or 2;

$Ar^1$ represents indanyl, tetrahydronaphthyl, naphthyl or phenyl, which latter two groups may be substituted by one or more substituents selected from chloro, fluoro, $OR^1$, $O(CH_2)_mCONR^{20}R^{21}$, $C(O)R^2$, $C_{1-6}$ alkyl (optionally substituted by one or more fluorine atoms), pyridyl, thiazinyl, phenyl or $C_{7-9}$ alkylphenyl which latter two groups are optionally substituted by one or more substituent selected from halo, nitro, $OR^3$, $C_{1-6}$ alkyl (optionally substituted by one or more fluorine atoms), $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$ and $SO_2NR^{17}R^{18}$;

m represents an integer 1 to 3;

$R^1$, $R^2$ and $R^3$ independently represent H, $C_{1-10}$ alkyl (optionally substituted by one or more fluorine atoms), $C_{7-9}$ alkylphenyl or phenyl, which latter group is optionally substituted by hydroxy; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently represent H, $C_{1-6}$ alkyl (optionally substituted by one or more fluorine atoms) or phenyl;

in which any alkyl group present may be interrupted by one or more oxygen atoms;

provided that when X represents $CH_2CH_2$, $Ar^1$ may not represent phenyl or phenyl substituted with one or more substituents $OR^1$, in which $R^1$ represents $C_{1-10}$ alkyl;

or a pharmaceutically acceptable derivative thereof, hereinafter referred to together as "the compounds of the invention".

We prefer X to represent $CH_2O$, $CH_2S$ or $C_2$ alkylene and $Ar^1$ to represent— naphthyl, which may be substituted by one or more substituents selected from chloro, fluoro, $OR^1$, $O(CH_2)_mCONR^{20}R^{21}$, and $C_{1-6}$ alkyl (optionally substituted by one or more fluorine atoms); or biphenylyl, which may be substituted on the ring adjacent to X by one or more substituents selected from chloro, fluoro, $OR^1$, $O(CH_2)_mCONR^{20}R^{21}$ and $C_{1-6}$ alkyl (optionally substituted by one or more fluorine atoms), and on the ring remote from X by one or more substituent selected from halo, nitro, $OR^3$, $C_{1-6}$ alkyl (optionally substituted by one or more fluorine atoms), $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$ and $SO_2NR^{17}R^{18}$.

Pharmaceutically acceptable derivatives include solvates and salts. Particular salts which may be mentioned include hydrochloride, hydrobromide, sulfonate, tosylate methanesulfonate and oxalate.

Alkylene groups which X may represent and the alkyl portion of alkylphenyl groups which $R^1$, $R^2$ and $R^3$ may represent may be saturated or unsaturated. Alkylphenyl groups are attached via the alkyl part of the group to the rest of the compound (and may be unsaturated or interrupted by one or more oxygen atoms), as distinct from phenyl substituted by alkyl. Alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ may represent or which may be substituted on one or more of the aromatic rings forming part of $Ar^1$ may be saturated or unsaturated, straight-chain or branched, and cyclic or acyclic (including alkyl groups substituted with a cycloalkyl group such as cyclopropylmethyl).

According to the invention there is also provided a process for the preparation of compounds of formula I as hereinbefore defined which comprises:

(a) reduction of a corresponding compound of formula II,

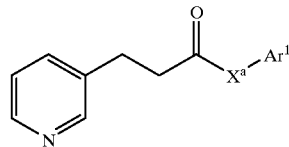

II wherein $X^a$ represents $(CH_2)_nS$, $(CH_2)_nO$ or $C_2$ alkylene and $Ar^1$ is as hereinbefore defined, with a suitable reducing agent (e.g. sodium borohydride) for example at room temperature in the presence of a suitable organic solvent (e.g. ethanol);

(b) preparation of a compound of formula I, wherein X represents $CH_2S$, CH=CH or C≡C, by reaction of 3-(3-pyridyl)-1-propionaldehyde with a compound of formula III, <p style="text-align:center">MZAr<sup>1</sup></p>

MZAr¹        III wherein M represents Li, Na, K or MgHal where Hal represents Cl, Br or I, Z represents $CH_2S$, CH=CH or C≡C and $Ar^1$ is as hereinbefore defined, for example at or below room temperature in the presence of a suitable organic solvent (e.g. tetrahydrofuran);

(c) preparation of a compound of formula I, wherein X $CH_2S$, $CH_2O$ or $(CH_2)_2$, by reaction of (±)-3-(2-oxiranylethyl)pyridine either with a compound of formula IV, MYAr¹        IV wherein Y represents O, S or $CH_2$ and M and $Ar^1$ are as hereinbefore defined, for example at or below room in a suitable solvent (e.g. dimethylformamide or tetrahydrofuran), or with a compound of formula VII,

 VII wherein Y and Ar¹ are as hereinbefore defined, for example by heating in the presence of a suitable base (e.g. sodium hydroxide) and an appropriate solvent system (e.g. aqueous ethanol);

(d) preparation of a compound of formula I, wherein X represents $CH_2S$, $CH_2O$ or $(CH_2)_2$, by reaction of a compound of formula V,

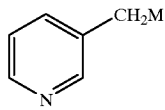 V wherein M is as hereinbefore defined with a compound of formula VI,

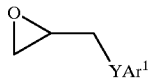 VI wherein Ar¹ and Y are as hereinbefore defined, for example at or below room temperature in the presence of a suitable organic solvent (e.g. tetrahydrofuran or diethyl ether);

(e) preparation of a compound of formula I, wherein X represents $CH_2S$, $CH_2O$ or $(CH_2)_2$, by reaction of α-(chloromethyl)-3-pyridinepropanol either with a compound of formula IV,

 IV wherein Y, M and Ar¹ are as hereinbefore defined, for example at or below room temperature in a suitable solvent (e.g. dimethylformamide or tetrahydrofuran), or with a compound of formula VII,

 VII wherein Y and Ar¹ are as hereinbefore defined, for example by heating in the presence of a suitable base (e.g. sodium hydroxide) and an appropriate solvent system (e.g. aqueous ethanol);

(f) preparation of a compound of formula I, wherein X represents $CH_2O$ or $CH_2S$, by reaction of a compound of formula IV or VII, as hereinbefore defined, with a suitably protected and activated derivative of 4-(3-pyridyl)-1,2-butanediol, for example at 60° C. in the presence of suitable base (e.g. sodium hydride) and an appropriate organic solvent (e.g. dimethylformamide);

(g) preparation of a compound of formula I, wherein X is as hereinbefore defined and Ar¹ represents an —Ar³—Ar⁴ group in which Ar³ represents naphthylene or phenylene optionally substituted by one or more substituents selected from chloro, fluoro, $OR^1$, $O(CH_2)_mCONR^{20}R^{21}$, $C(O)R^2$, $C_{1-6}$ alkyl (optionally substituted by one or more fluorine atoms) and Ar⁴ represents pyridyl, thiazinyl or phenyl which latter group is optionally substituted by one or more substituents selected from halo, nitro, $OR^3$, $C_{1-6}$ alkyl (optionally substituted by one or more fluorine atoms), $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$, $SO_2NR^{17}R^{18}$, by reaction of a compound of formula VIII,

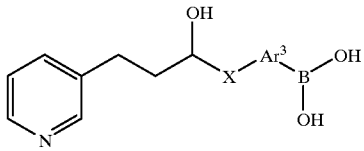 VIII wherein X and Ar³ are as hereinbefore defined, with an aryl halide of formula XX Ar⁴Hal      XX wherein Hal represents triflate, Cl, Br or I and Ar⁴ is as hereinbefore defined, under the conditions of the Suzuki reaction (*Synthetic Communications* 11(7), 513–519, 1981) for example at 100° C. in the presence of a suitable catalyst and base (e.g. tetrakis(triphenylphosphine)palladium(0) and aqueous sodium carbonate) in a suitable solvent (e.g. ethanol/toluene);

(h) preparation of a compound of formula I wherein X is C≡C by reaction between a compound of formula X,

 X where Q represents Br, I or triflate and Ar¹ is as hereinbefore defined, with 5-(3-pyridyl)pent-1-yn-3-ol under a suitable catalytic system (e.g. bis(triphenylphosphine)palladium(II) chloride and triethylamine) in a suitable solvent (e.g. dimethylformamide) with heating (e.g. at 90° C.) or at room temperature in the presence of catalytic copper(I) halide;

(i) preparation of a compound of formula I, wherein X is as hereinbefore defined and Ar¹ represents an —Ar³—Ar⁴ group in which Ar³ and Ar⁴ are as hereinbefore defined, by reaction of a compound of formula XI,

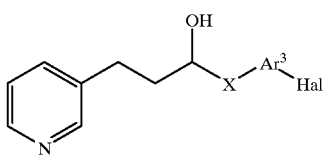 XI wherein Hal represents Cl, Br, I or triflate and X and Ar³ are as hereinbefore defined, with an arylboronic acid of formula XXI,

 XXI wherein Ar⁴ is as hereinbefore defined, under the conditions of the Suzuki reaction (*Synthetic Communications* 11(7), 513–519, 1981) for example at 100° C. in the presence of a suitable catalyst and base (e.g. tetrakis(triphenylphosphine)palladium(0) and aqueous sodium carbonate) in a suitable solvent (e.g. ethanol/toluene);

(j) reduction of a compound of formula XII,

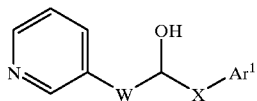

XII wherein W represents CH=CH or C≡C and X and Ar¹ are as hereinbefore defined, by reduction with a suitable reducing agent (e.g. hydrogen) in the presence of a suitable catalyst (e.g. palladium on charcoal) in a suitable solvent (e.g. ethanol);

(k) preparation of a compound of formula I, wherein X is CH=CH, by reaction of a phosphonium salt of formula XIII,

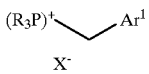

XIII wherein R is an aryl group such as phenyl, X⁻ is chloride, bromide or iodide and Ar¹ is as hereinbefore defined, with a suitably protected derivative of 2-hydroxy-4-(3-pyridyl) butyraldehyde, for example at −60° C. in the presence of a suitable base (e.g. lithium diisopropylamide), in a suitable solvent (e.g. tetrahydrofuran), or reaction of a compound of formula XXII,

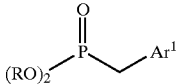

XXII wherein R represents $C_{1-6}$ alkyl or aryl and Ar¹ is as hereinbefore defined, with a suitably protected derivative of 2-hydroxy-4-(3-pyridyl)butyraldehyde, for example at room temperature in the presence of a suitable base (e.g. lithium diisopropylamide), in a suitable solvent (e.g. tetrahydrofuran);

(l) preparation of a compound of formula I, wherein X is $(CH_2)_2O$ or $(CH_2)_2S$, by reaction between a compound of formula VII, as hereinbefore defined, an optionally protected and suitably activated derivative of 5-(3-pyridyl)-1,3-pentanediol for example at 60° C. in the presence of a suitable base (e.g. sodium hydride) and an appropriate organic solvent (e.g. dimethylformamide);

(m) preparation of a compound of formula I, wherein X is $CH_2CH_2$, by reaction of a corresponding compound of formula I wherein X is C≡C with a suitable reducing agent (e.g. hydrogen) in the presence of a suitable catalyst (e.g. palladium on charcoal) in a suitable solvent (e.g. ethanol);

(n) preparation of a compound of formula I, wherein X is $CH_2CH_2$, by reaction of a corresponding compound of formula I wherein X is CH=CH with a suitable reducing agent (e.g. hydrogen) in the presence of a suitable catalyst (e.g. palladium on charcoal) in a suitable solvent (e.g. ethanol);

(o) preparation of a compound of formula I, wherein X is trans-CH=CH, by reaction of a corresponding compound of formula I wherein X is C≡C with a suitable reducing agent (e.g. Red-Al®) in a suitable solvent (e.g. toluene);

(p) preparation of a compound of formula I, wherein X is cis-CH=CH, by reaction of a corresponding compound of formula I wherein X is C≡C with a suitable reducing agent (e.g. hydrogen) in the presence of a suitable catalyst (e.g. palladium on barium sulfate) in a suitable solvent (e.g. ethanol);

(q) preparation of a compound of formula I, wherein X is CH=CH, by reaction of a compound of formula IX with 5-(3-pyridyl)-1-penten-3-ol, for example at 100° C. in the presence of an appropriate catalytic system (e.g. palladium (II) acetate, tri-o-tolylphosphine, and triethylamine) and a suitable solvent (e.g. acetonitrile);

(r) preparation of a compound of formula I, wherein X is as hereinbefore defined and Ar¹ represents an —Ar³—Ar⁶ group in which Ar³ is as hereinbefore defined and Ar⁶ represents a $C_{7-9}$ alkylphenyl group which is optionally substituted by one or more substituents selected from halo, nitro, OR³, $C_{1-6}$ alkyl (optionally substituted by one or more fluorine atoms), C(O)R⁴, C(O)OR⁵, C(O)N(R⁶)R⁷, CN, $CH_2OR^{14}$, $CH_2NR^{15}R^{16}$, N(R⁸)R⁹, N(R¹⁰)SO₂R¹¹, N(R¹²)C(O)R¹³, OC(O)R¹⁹, by reaction between a compound of formula XI and a compound of formula XXV, UAr⁶         XXV wherein U represents a $C_{2-3}$ alkylenyl group and Ar⁶ is as hereinbefore defined, for example at 100° C. in the presence of an appropriate catalytic system (e.g. palladium(II) acetate, tri-o-tolylphosphine, and triethylamine) and a suitable solvent (e.g. acetonitrile);

(s) reduction of a compound of formula XXVI,

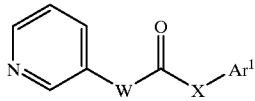

XXVI wherein W, X and Ar¹ are as hereinbefore defined under suitable reaction conditions;

(t) preparation of a compound of formula I, wherein Ar¹ represents naphthyl or phenyl optionally substituted by one or more substituents selected from chloro, fluoro, OR¹, $O(CH_2)_mCONR^{20}R^{21}$, C(O)R², $C_{1-6}$ alkyl (optionally substituted by one or more fluorine atoms), or by phenyl or $C_{7-9}$ alkylphenyl which latter two groups are optionally substituted by one or more substituent selected from halo, nitro, OR³, $C_{1-6}$ alkyl (optionally substituted by one or more fluorine atoms), C(O)R⁴, C(O)OR⁵, C(O)N(R⁶)R⁷, CN, $CH_2OR^{14}$, $CH_2NR^{15}R^{16}$, N(R⁸)R⁹, N(R¹⁰)SO₂R¹¹, N(R¹²)C(O)R¹³, OC(O)R¹⁹ and SO₂NR¹⁷R¹⁸, from a corresponding compound of formula I including a group convertible to a halo, OR¹, $O(CH_2)_mCONR^{20}R^{21}$, C(O)R², alkyl, fluoroalkyl, nitro, OR³, C(O)R⁴, C(O)OR⁵, C(O)N(R⁶)R⁷, CN, $CH_2OR^{14}$, $CH_2NR^{15}R^{16}$, N(R⁸)R⁹, N(R¹⁰)SO₂R¹¹, N(R¹²)C(O)R¹³, OC(O)R¹⁹ or SO₂NR¹⁷R¹⁸ group by functional group interconversion by methods well known to those skilled in the art;

wherein any functional group present may be protected before reaction occurs and deprotected to give the compounds of formula I.

In a further aspect of the invention there is provided compounds of formula II and XII, as defined above.

Compounds of formula II wherein $X^a$ represents $(CH_2)_2S$ or $(CH_2)_2O$, may be prepared by reaction of 5-(3-pyridyl)-1-penten-3-one with a compound of formula VII as hereinbefore defined, for example in the presence of a suitable base (e.g. triethylamine) and an appropriate organic solvent (e.g. toluene) under conditions well known to those skilled in the art.

Compounds of formula II wherein $X^a$ represents $(CH_2)_2$ or CH=CH may be prepared by reaction of 5-(3-pyridyl)-1-penten-3-ol or 5-(3-pyridyl)-1-penten-3-one respectively with a compound of formula IX,

 IX wherein Hal represents Cl, Br, I or triflate and $Ar^1$ is as hereinbefore defined, for example at 100° C. in the presence of an appropriate catalytic system (e.g. palladium(II) acetate, tri-o-tolylphosphine and triethylamine) and a suitable solvent (e.g. acetonitrile).

Compounds of formula II wherein X and $Ar^1$ are as hereinbefore defined may also be prepared by reduction of a corresponding compound of formula XIV,

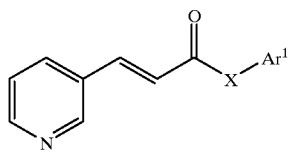 XIV wherein X and $Ar^1$ are as hereinbefore defined, for example using a suitable catalytic reduction system (e.g. palladium on charcoal and ammonium formate), at elevated temperature (e.g. reflux) in the presence of suitable solvent (e.g. ethanol).

In a further aspect of the invention there is provided a compound of formula XIV, as defined above.

The reduction of the compound of formula II to the compound of formula I may be done using a selective or non-selective reducing agent. In the former case, $X^a$ would be the same in both compounds. In the latter case, however, $X^a$ may be an unsaturated group in the compound of formula II, which is converted to $(CH_2)_2$ in the final product. It will be appreciated that a compound of formula XIV may also be converted to a compound of formula I without the need to isolate the compounds of formula II formed in situ, if a non-selective reducing agent is used.

Compounds of formula III may be prepared by reacting a corresponding compound of formula XV,

 XV wherein $Ar^1$ and Z are as hereinbefore defined with an appropriate base in the presence of a suitable organic solvent.

Compounds of formula IV wherein Y represents O or S may be prepared by reacting a corresponding compound of formula VII as hereinbefore defined, with an appropriate base (e.g. a metal hydride) in the presence of a suitable organic solvent (e.g. dimethylformamide or tetrahydrofuran).

Compounds of formula IV wherein Y represents $CH_2$ may be prepared by reaction of a compound of formula XXXII,

 XXXII wherein $Ar^1$ is as hereinbefore defined, with a suitable base (e.g. tert-butyllithium) in a suitable solvent (e.g. tetrahydrofuran) at low temperature (e.g. −100° C.); or by treatment of a compound of formula XXXIII,

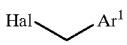 XXXIII where Hal represents, Cl, Br or I, with magnesium metal in a suitable solvent (e.g. tetrahydrofuran) and forming a Grignard reagent.

Compounds of formula V may be prepared by reacting 3-picoline with an appropriate base (e.g. lithium diisopropylamide) in the presence of a suitable organic solvent (e.g. tetrahydrofuran).

Compounds of formula VI may be prepared by reaction of a corresponding compound of formula VII, as hereinbefore defined, with epichlorohydrin or a suitably activated glycidol derivative in the presence of an appropriate base-solvent system (e.g. caesium carbonate in acetonitrile or aqueous ethanolic potassium hydroxide).

Non-commercial compounds of formula VII, wherein $Ar^1$ represents an $-Ar^3-Ar^4$ group in which $Ar^3$ and $Ar^4$ are as hereinbefore defined, may be conveniently prepared by Suzuki reaction (*Synthetic Communications* 11(7), 513–519, 1981) between a suitable aryl halide and a suitable arylboronic acid, for example, reaction between $Ar^4$Hal and an arylboronic acid of formula XXIII,

 XXIII or reaction between $Ar^4B(OH)_2$ and an aryl halide of formula XXIV,

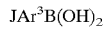 XXIV wherein J represents OH, SH or a suitably protected version of these groups and $Ar^3$ is as hereinbefore defined.

Non-commercial arylboronic acids may be prepared from a suitable aryl halide (e.g. Compounds of formula XI, XX, XXIII) by treatment with a suitable base (e.g. tert-butyllithium) and subsequent reaction with a trialkyl borate (e.g. triisopropyl borate) in a suitable solvent (e.g. tetrahydrofuran).

It will be appreciated by those skilled in the art that boronic acids can exist as various anhydrides and the use of such compounds in producing a compound of formula I are within the scope of this invention (especially e.g. a compound of formula VIII) and also alkylarylborates which can take part in the processes described.

Compounds of formula VII where Y is S and where $Ar^1$ is as hereinbefore defined may be prepared by the hydrolysis of an S-thiocarbamate which in turn is prepared from the corresponding O-thiocarbamate by heating in a high boiling solvent (e.g. dimethylaniline) which in turn is prepared by reaction of a compound of formula VII where Y is O and is a known compound or is prepared as hereinbefore defined or is easily prepared by those skilled in the art.

Compounds of formula VIII may be prepared from compounds of formula XVI,

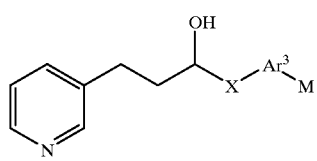 XVI wherein X, $Ar^3$ and M are as hereinbefore defined, by reaction with a trialkyl borate (e.g. triisopropyl borate) in a suitable solvent (e.g. tetrahydrofuran).

Compounds of formula XVI may be prepared from compounds of formula XI by treatment with a suitable base (e.g. tert-butyllithium) in a suitable solvent (e.g. tetrahydrofuran).

Compounds of formula XI can be prepared using the methods hereinbefore defined replacing $Ar^1$ with a group $Ar^3Hal$ where Hal represents, Cl, Br, I or triflate or a functional group (e.g. amino) that is subsequently converted to halogen by methods well known to those skilled in the art and $Ar^3$ is as hereinbefore defined.

Compounds of formula XII can be prepared by reaction between a 3-halopyridine (e.g. 3-iodopyridine) and a compound of formula XVII,

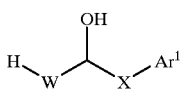

XVII wherein X represents $(CH_2)_nO$, $(CH_2)_nS$ or $(CH_2)_2$ and W and $Ar^1$ are as hereinbefore defined, for example, in the presence of a catalyst (e.g. bis(triphenylphosphine) palladium(II) chloride) and a suitable base (e.g. triethylamine) in a suitable solvent (e.g. acetonitrile) with heating or at room temperature with or without copper(I) salt catalysis.

Compounds of formula XVII can be prepared from a compound of formula XVIII,

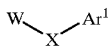

XVIII wherein X represents $(CH_2)_nO$, W and $Ar^1$ are as hereinbefore defined by ozonolysis followed by treatment with a reducing agent (e.g. triphenylphosphine) followed by addition of a suitable organometallic reagent (e.g. vinylmagnesium bromide or ethynylmagnesium bromide) in a suitable solvent (e.g. dichloromethane).

Compounds of formula XVIII wherein X represents $(CH_2)_nO$ or $(CH_2)_nS$ and W and $Ar^1$ are as hereinbefore defined may be prepared from a compound of formula XXXI,

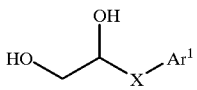

XXXI wherein X represents $(CH_2)_nO$ or $(CH_2)_nS$ and $Ar^1$ is as hereinbefore described by treatment with a suitable oxidant (e.g. sodium metaperiodate) in a suitable solvent (e.g. aqueous methanol) followed by treatment with a suitable organometallic reagent (e.g. vinylmagnesium bromide or ethynylmagnesium bromide) in a suitable solvent (e.g. dichloromethane).

Compounds of formula XIV may be prepared by reaction of a compound of formula XIX,

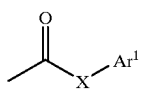

XIX wherein $Ar^1$ is as hereinbefore defined, with 3-pyridinecarboxaldehyde for example at room temperature in the presence of an appropriate base (e.g. aqueous sodium hydroxide) and an appropriate organic solvent (e.g. ethanol).

5-(3-Pyridyl)pent-1-yn-3-ol can be prepared by reaction of 3-(3-pyridyl)-1-propionaldehyde with trimethylsilylacetylene in the presence of a base (e.g. n-butyllithium) in a suitable solvent (e.g. tetrahydrofuran) followed by desilylation of the alkyne using suitable reagents (e.g. potassium carbonate in methanol).

Compounds of formula XXVI wherein W represents CH=CH and X and $Ar^1$ are as hereinbefore defined may be prepared by reaction of pyridine-3-carboxaldeyde and a compound of formula XXVII,

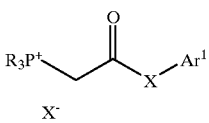

XXVII wherein R is an aryl group such as phenyl, $X^-$ is chloride, bromide or iodide and X and $Ar^1$ are as hereinbefore defined, or a compound of formula XXVIII,

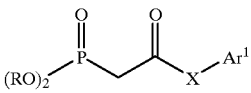

XXVIII wherein R is an aryl group such as phenyl or a $C_{1-6}$ alkyl group for example in the presence of a base (e.g. lithium diisopropylamide) in a suitable solvent (e.g. tetrahydrofuran) at room temperature or with heating.

Compounds of formula XXVII may be prepared by reaction of a triarylphosphine (e.g. triphenylphosphine) with a compound of formula XXIX,

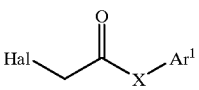

XXIX wherein Hal represents, Cl, Br or I and X and $Ar^1$ are as hereinbefore defined, under conditions well known to those skilled in the art. Compounds of formula XXIX may be prepared from the corresponding alcohol by oxidation (e.g. with chromic acid). The corresponding halohydrins may be prepared by acid-catalysed ring opening of the corresponding epoxides (e.g. a compound of formula VI).

Compounds of formula XXVIII may be prepared by reaction of a compound of formula XXIX with a $C_{1-6}$ trialkyl phosphite (e.g. triethyl phosphite) under conditions well known to those skilled in the art.

Compounds of formula XXVIII may also be prepared by reaction of a dialkyl methanephosphonate (e.g. dimethyl methanephosphonate) with a compound of formula XXX wherein R represents $C_{1-6}$ alkyl, X represents $CH_2O$ or $CH_2S$ and $Ar^1$ is as hereinbefore defined in the presence of a suitable base (e.g. n-butyllithium) in a appropriate solvent (e.g. tetrahydrofuran) at low temperature (e.g. −78° C.).

XXX

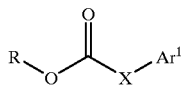

Compounds of formula XXX may be prepared in the case where X and $Ar^1$ are as hereinbefore described by reaction between a compound of formula VII with an α-haloacetic acid ester in the presence of a base (e.g. potassium carbonate) in a suitable solvent (e.g. acetone).

3-(Oxiranylethyl)pyridine may be prepared by reacting 3-(3-pyridyl)-1-propionaldehyde with trimethylsulfoxonium iodide and sodium hydride, at or below room temperature in an inert atmosphere in the presence of a suitable organic solvent such as dimethyl sulfoxide.

(±)-α-(Chloromethyl)-3-pyridinepropanol may be prepared by the reaction of 3-picoline with epichlorohydrin, for example at −10° C. in the presence of a suitable base (e.g. lithium diisopropylamide) and an appropriate organic solvent (e.g. tetrahydrofuran).

2-Hydroxy-4-(3-pyridyl)butyraldehyde may be prepared by suitable protection of the secondary hydroxyl group (e.g. as the benzoate ester) followed by the oxidation of the primary hydroxyl group of 4-(3-pyridyl)-1,2-butanediol by methods well known to those skilled in the art (e.g. as described hereinafter).

5-(3-Pyridyl)-1,3-pentanediol can be conveniently prepared by ozonolysis of 6-(3-pyridyl)hex-1-en-4-ol followed by reductive work up with a suitable reducing agent (e.g. sodium borohydride) in a suitable solvent (e.g. methanol). 6-(3-Pyridyl)hex-1-en-4-ol can be conveniently prepared by reaction between 3-(3-pyridyl)-1-propionaldehyde and allylmagnesium halide in a suitable solvent (e.g. tetrahydrofuran).

4-(3-Pyridyl)-1,2-butanediol may be prepared by acid hydrolysis of 4-(3-pyridyl)-1,2-O-isopropylidenebutane-1,2-diol in the presence of a suitable acid (e.g. aqueous hydrochloric acid). 4-(3-Pyridyl)-1,2-O-isopropylidenebutane-1,2-diol may be prepared by reduction of 4-(3-pyridyl)-1,2-O-isopropylidenebut-3-ene-1,2-diol which latter compound may in turn be obtained by reaction of 3-pyridylmethyltriphenylphosphonium chloride (*J. Med. Chem.* (1986) 29, 1461) and 2,3-O-isopropylideneglyceraldehyde (see e.g. *Organic Synthesis* (1995) 72, 1 and 6), e.g. as described hereinafter.

Protection and activation of 4-(3-pyridyl)-1,2-butanediol and 5-(3-pyridyl)-1,3-pentanediol may be achieved by producing a corresponding compound in which the secondary hydroxyl group is protected, for example by means of an organosilyl group such as a tert-butyldimethylsilyl substituent, and the primary hydroxyl group is activated to a suitable leaving group, for example a tosylate group. Alternatively, a bivalent substituent such as O,O-sulfonyl may be used to give a cyclic sulfate, whereby one substituent fulfils the role of both protection and activation.

5-(3-Pyridyl)pent-1-en-3-one may be prepared by oxidation of 5-(3-pyridyl)-1-penten-3-ol in the presence of a suitable oxidising agent (e.g. chromic acid) and an appropriate organic solvent (e.g. acetone). 5-(3-Pyridyl)-1-penten-3-ol may be prepared by reaction 3-(3-pyridyl)-1-propionaldehyde with vinyl magnesium bromide, for example at 0° C. in the presence of a suitable organic solvent (e.g. tetrahydrofuran).

3-(3-Pyridyl)-1-propionaldehyde is known in the literature (see Example 3 of International Patent Application WO-A-92/19593).

Compounds of formula III, IV, VI, VII, IX, X, XV, XVIII, XIX, XX, XXI, XXII, XXIII, XXIV, XXV, XXVII, XXVIII, XXIX, XXX, XXXI, XXXII and XXXIII are either prepared as described above, are commercially available, are well known in the literature or may be prepared conveniently using known techniques.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include organosilyl groups (e.g. tert-butyldimethylsilyl, tert-butyldiphenylsilyl or trimethylsilyl), benzyl and tetrahydropyranyl. Suitable protecting groups for amino include tert-butoxycarbonyl or benzyloxy carbonyl. Suitable protecting groups for carboxylic acid include $C_{1-6}$ alkyl or benzyl esters.

The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

"Functional group interconversion" includes the possibility of converting a hydrogen atom into a functional group and vice versa. Among possible functional group interconversions are, to make the substituted naphthyl or first phenyl group:

conversion of $OR^1$ where $R^1$ represents hydrogen to $OR^1$ where $R^1$ represents alkyl (optionally substituted by one or more fluorine atoms) or alkylphenyl;

conversion of $OR^1$ where $R^1$ represents alkyl (optionally substituted by one or more fluorine atoms) or alkylphenyl to $OR^1$ where $R^1$ represents hydrogen;

conversion of $OR^1$ where $R^1$ represents hydrogen to $O(CH_2)_mCONR^{20}R^{21}$;

conversion of $O(CH_2)_mCONR^{20}R^{21}$ where $R^{20}$ or $R^{21}$ represent hydrogen to $O(CH_2)_mCONR^{20}R^{21}$ where $R^{20}$ or $R^{21}$ represent $C_{1-6}$ alkyl (optionally substituted by one or more fluorine atoms) or phenyl;

conversion of hydrogen attached to an aromatic ring to $C(O)R^2$ by the Friedel-Crafts reaction;

conversion of $C(=CH_2)R^2$ to $C(O)R^2$ by ozonolysis;

conversion of amino to chloro, fluoro or hydroxy;

conversion of $O(CH_2)_mCO(O)R^{22}$, wherein $R^{22}$ represents $C_{1-6}$ alkyl, to $O(CH_2)_mCONR^{20}R^{21}$; and conversion of $CH(OH)R^2$ to $C(O)R^2$;

and to make the substituted second phenyl or alkylphenyl group:

conversion of hydrogen to halo or nitro;

conversion of amino to halo, hydroxy or CN;

conversion of nitro to amino;

conversion of $OR^3$ where $R^3$ represents hydrogen to $OR^3$ where $R^3$ represents alkyl (optionally substituted by one or more fluorine atoms) or alkylphenyl;

conversion of $OR^3$ where $R^3$ represents alkyl (optionally substituted by one or more fluorine atoms) or alkylphenyl to $OR^3$ where $R^3$ represents hydrogen;

conversion of C(=CH$_2$)R$^4$ to C(O)R$^4$ by ozonolysis;

conversion of C(O)OR$^5$ where R$^5$ represents hydrogen to C(O)OR$^5$ where R$^5$ represents alkyl (optionally substituted by one or more fluorine atoms) or phenyl;

conversion of C(O)OR$^5$ where R$^5$ represents alkyl (optionally substituted by one or more fluorine atoms) or phenyl to C(O)OR$^5$ where R$^5$ represents hydrogen;

conversion of C(O)OR$^5$ to C(O)N(R$^6$)R$^7$;

conversion of C(O)N(R$^6$)R$^7$ to COOH;

conversion of one C(O)N(R$^6$)R$^7$ group to another C(O)N(R$^6$)R$^7$ group by transamidation;

conversion of one C(O)OR$^5$ group to another C(O)OR$^5$ group by transesterification;

conversion of one halo group to another halo group, optionally via on organotin reagent;

conversion of C(O)OR$^5$ or CHO to CH$_2$OH;

conversion of CHO to CH$_2$NR$^{15}$R$^{16}$;

conversion of N(R$^8$)R$^9$ where R$^8$ or R$^9$ represent hydrogen to N(R$^8$)R$^9$ where R$^8$ or R$^9$ represent alkyl (optionally substituted by one or more fluorine atoms);

conversion of NHR$^{10}$ to N(R$^{10}$)SO$_2$R$^{11}$;

conversion of NHR$^{12}$ to N(R$^{12}$)C(O)R$^{13}$;

conversion of OH to OC(O)R$^{19}$;

conversion of CH(OH)R$^4$ to C(O)R$^4$;

conversion of methyl to CH$_2$Hal, where Hal represents halogen, and then to CH$_2$OR$^{14}$; and conversion of CH$_2$Hal, where Hal represents halogen, to CH$_2$NR$^{15}$R$^{16}$.

Thus according to a further aspect of the invention there is provided a corresponding compound of formula I wherein Ar$^1$ represents optionally substituted naphthyl or phenyl further including a substituent selected from amino, O(CH$_2$)$_m$CO(O)R$^{22}$ and CH(OH)R$^2$ or Ar$^1$ represents naphthyl or phenyl substituted with at least one group including phenyl or C$_{7-9}$ alkylphenyl further including a substituent selected from CH(OH)R$^4$ and CH$_2$Hal, wherein R$^{22}$ represents C$_{1-6}$ alkyl, Hal represents halogen and m, R$^2$ and R$^4$ are as hereinbefore defined, except that R$^4$ does not represent hydrogen.

The compounds of the invention may also contain one or more asymmetric carbon atoms and may therefore exhibit optical and/or diastereoisomerism. All stereoisomers are included within the scope of the invention.

Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques.

Alternatively, the desired optical isomers may be made by the following techniques:

(i) Reaction of the appropriate optically active starting materials under conditions which will not cause racemisation. For example, optically active 4-(3-pyridyl)-1,2-O-isopropylidenebut-3-ene-1,2-diol may be prepared by reaction of 3-pyridylmethyltriphenylphosphonium chloride (*J. Med. Chem.* (1986) 29, 1461) with optically active 2,3-O-isopropylideneglyceraldehyde (*Organic Synthesis* (1995) 72, 1 and 6). Optically active 4-(3-pyridyl)-1,2-O-isopropylindenebut- 3-ene-1,2-diol may then be used to prepare compounds of formula I wherein X is as hereinbefore defined.

(ii) Inversion of one optically active isomer of a compound of formula I to another under appropriate reaction conditions. Inversion reactions may proceed by conversion of the OH group in an optically active isomer of a compound of formula I into a suitable leaving group, followed by inversion of the chiral centre using an appropriate nucleophile. For example, certain optically active isomers of compounds of formula I may be reacted with triphenylphosphine and diethyl azodicarboxylate, followed by inversion using benzoic acid. The resultant benzoate may then be hydrolysed to the corresponding alcohol using an appropriate base.

Derivatisation, for example with a homochiral acid followed by separation of the diastereomeric derivatives by conventional means (e.g. HPLC, chromatography over silica) followed by regeneration of the compounds of the invention from the homochiral derivative by appropriate means well known to those skilled in the art. For example racemic mixtures of compounds of formula I may be reacted with an appropriate homochiral resolving agent (e.g. (2S)-5-oxo-1-(2-oxo-2-phenylacetyl)pyrrolidine-2-carboxylic acid) separated and subsequently regenerated by hydrolysis. (2S)-5-Oxo-1-(2-oxo-2-phenylacetyl)pyrrolidine-2-carboxylic acid may be prepared by reaction of L-(–)-pyroglutamic acid tert-butyl ester (*J. Med. Chem.* (1985) 28, 1596) with benzoylformyl chloride followed by deprotection in the presence of trifluoroacetic acid.

The compounds of the invention are useful because they possess pharmacological activity and more particularly activity in the modulation of inflammatory and allergic conditions, for example as shown in the test described below. They are therefore indicated as pharmaceuticals.

The compounds may be used in the treatment of reversible obstructive airways disease or allergic conditions of the skin, nose and eye.

The compounds of the invention are indicated for use in the treatment or prevention of autoimmune, inflammatory, proliferative and hyperproliferative diseases, and of cutaneous manifestations of immunologically-mediated diseases, for example rheumatoid arthritis, psoriasis, atopical dermatitis, contact dermatitis and further eczematous dermatitides, urticaria, cutaneous eosinophilias, acne, Alopecia areata, eosinophilic fascitis, atherosclerosis and the like.

The compounds of the invention are also indicated in the treatment of respiratory diseases, for example sarcoidosis, farmer's lung and related diseases, fibroid lung, idiopathic interstitial pneumonia and reversible obstructive airways diseases which latter includes conditions such as asthma (e.g. bronchial asthma, allergic asthma, intrinsic asthma, extrinsic asthma and dust asthma), particularly chronic or inveterate asthma (e.g. late asthma and airway hyperresponsiveness), bronchitis and the like.

The compounds of the invention are also indicated the treatment of certain eye diseases such as vernal conjunctivitis, and in the treatment certain skin diseases including dermatomyositis and photoallergic sensitivity and periodontal disease.

The compounds of the invention are also indicated in the treatment of inflammation of mucosa and blood vessels such as gastric ulcers, vascular damage caused by ischaemic diseases and thrombosis, ischaemic bowel disease, inflammatory bowel disease and irritable bowel syndrome and also in the treatment of myocardial injury resulting from ischaemic heart disorders.

Further, the compounds of the invention are indicated in the treatment of diseases including inflammations/allergies such as rhinitis, including all conditions characterised by inflammation of the nasal mucus membrane, such as acute rhinitis, allergic rhinitis, atrophic rhinitis, chronic rhinitis including rhinitis caseosa, hypertrophic rhinitis, rhinitis purulenta and rhinitis sicca, rhinitis medicamentosa, membranous rhinitis including croupous, fibrinous and pseudomembranous rhinitis, scrofulous rhinitis, seasonal rhinitis including rhinitis nervosa (hay fever) and vasomotor rhinitis. Of particular interest are allergic rhinitis and seasonal rhinitis including rhinitis nervosa (hay fever).

The compounds of the invention are also indicated in the treatment of nasal polyps and allergic manifestations of the nasopharynx other than those described hereinbefore, and intestinal conditions such as Coeliac disease, eosinophilic gastro-enteritis, mastocytosis, Crohn's disease and ulcerative colitis; and food related allergic diseases which have symptomatic manifestation remote from the gastrointestinal tract, for example migraine, rhinitis and eczema.

Of particular interest amongst the above indications is use of the compounds of the invention in a reversible obstructive airways disease, most particularly asthma and especially the prophylaxis of asthma.

According to a further aspect of the invention there is thus provided the use of a compound of formula I, as hereinbefore defined, or a pharmaceutically acceptable derivative thereof, as active ingredient in the manufacture of a medicament for the treatment of a reversible obstructive airways disease.

Administration of the compounds of the invention may be topical (for example by inhalation to the lung). The compounds of the invention may be inhaled as a dry powder which may be pressurised or non-pressurised.

In non-pressurised powder compositions, the active ingredient in finely divided form may be used in admixture with a larger sized pharmaceutically acceptable inert carrier.

The composition may alternatively be pressurised and contain a compressed gas, e.g. nitrogen, or a liquefied gas propellant. In such pressurised compositions, the active ingredient is preferably finely divided. The pressurised composition may also contain a surface active agent.

The pressurised compositions may be made by conventional methods.

The compounds of the invention may be administered systemically (for example by oral administration to the gastrointestinal tract). The active ingredient may be formulated together with known adjuvants, diluents or carriers using conventional techniques to produce tablets or capsules for oral administration to the gastrointestinal tract.

Examples of suitable adjuvants, diluents or carriers for oral administration in the form of tablets, capsules and dragees include microcrystalline cellulose, calcium phosphate, diatomaceous earth, a sugar such as lactose, dextrose or mannitol, talc, stearic acid, starch, sodium bicarbonate and/or gelatin.

According to a further aspect of the invention there is provided a pharmaceutical composition including a compound of formula I as hereinbefore defined or a pharmaceutically acceptable derivative thereof, in admixture with a pharmaceutically acceptable adjuvant diluent or carrier.

Suitable doses for such oral administration are in the range from 0.3 to 30 mg kg$^{-1}$ day$^{-1}$, for example 3 mg kg$^{-1}$ day$^{-1}$.

According to a further aspect of the present invention, there is provided a method of treatment of a reversible obstructive airways disease, which method comprises administration of a therapeutically effective amount of a compound of formula I as hereinbefore defined, or a pharmaceutically acceptable derivative thereof, to a person suffering from, or susceptible to, the disease.

It will be understood by those skilled in the art that certain functional groups in the compounds of the invention may be protected using appropriate protecting groups as hereinbefore described to form "protected derivatives" of compounds of the invention. It will also be appreciated that, although such protected derivatives may not possess pharmacological activity as such, they may be administered and thereafter metabolised in the body to form compounds of the invention which are pharmacologically active. Such derivatives may therefore be described as "prodrugs". All protected derivatives and prodrugs of compounds of formula I are included within the scope of the invention.

The compounds of the invention have the advantage that they may be more efficacious, be less toxic, be longer acting, have a broader range of activity, be more potent, produce fewer side effects, be more easily absorbed than, or that they may have other useful pharmacological properties over, compounds known in the prior art.

The pharmacological activity of the compounds of the invention may be tested by the method of E. Wells et al, 'Characterization of primate bronchoalveolar mast cells: II—inhibition of histamine, LTC$_4$ and PGD$_2$ release from primate bronchoalveolar mast cells and a comparison with rat peritoneal mast cells', *J. Immunol.*, vol. 137, 3941, 1986.

The invention is illustrated by the following Examples.

In the following examples compounds were further purified, where necessary, by reverse phase HPLC over a μ-Bondapak™ column using gradient elution with 0.1% aqueous trifluoroacetic acid:methanol or with 0.1% aqueous ammonium acetate: methanol, prior to biological testing.

EXAMPLE 1

(±)-α-(2-Naphthylthiomethyl)-3-pyridinepropanol

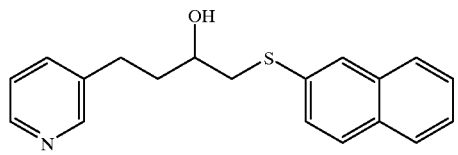

(a) (±)-3-(2-Oxiranylethyl)pyridine

In a three-necked flask equipped with a stirrer was placed sodium hydride (60% dispersion in oil; 0.42 g) under a nitrogen atmosphere. This was washed with dry ether to remove the oil and then suspended in dry dimethyl sulfoxide (10 ml). Trimethylsulfoxonium iodide (2.01 g) was then added and after 15 minutes stirring a clear solution resulted. A solution of 3-(3-pyridyl)-1-propionaldehyde (1.30 g, prepared according to the method of Example 3 of International Patent Application No. WO-A-92/19593) in dimethyl sulfoxide (5 ml) was added to give a clear yellow solution. After one hour the reaction mixture was poured into water and ethyl acetate and the organic phase separated and dried over anhydrous magnesium sulfate. The organic phase was concentrated under reduced pressure and the residue purified by column chromatography over silica to give the sub-title epoxide (0.48 g).

MS (EI) 148 (M–H)$^+$ (b) (±)-α-(2-Naphthylthiomethyl)-3-pyridinepropanol

Sodium hydride (60% dispersion in oil, 0.05 g) was added to a solution of 2-thionaphthol (0.174 g) in dry dimethylformamide (3 ml). A solution of (±)-3-(2-oxiranylethyl) pyridine (0.15 g) in tetrahydrofuran (1 ml) was added and the reaction mixture stirred for three hours at ambient temperature. The solution was poured into water which was extracted with ethyl acetate. The organic extracts were separated, dried over anhydrous magnesium sulfate, filtered and concentrated under reduced pressure. The product was purified by column chromatography on silica eluting with ethyl acetate to give the title compound as a white solid (0.15 g).

m.p. 90–92° C.

MS (FAB) 310 (M+H)+

$^1$H NMR (CDCl$_3$) 8.45(2 H, m); 7.7(4 H, m); 7.5(4 H, m); 7.15(1 H, m); 3.7(1 H, m); 3.2(1 H, m); 3.0(1 H, m); 2.8(1 H, m); 2.7-2.6(2 H, m); 1.8(2 H, m).

EXAMPLE 2

(±)-α-(4-Phenylphenylthiomethyl)-3-pyridinepropanol

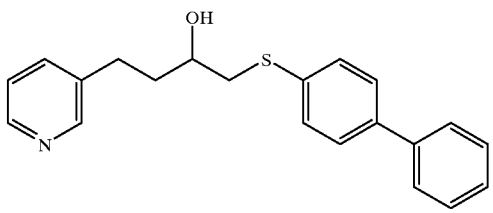

Prepared according to the method described in Example 1 from 4-phenylthiophenol (0.186 g), sodium hydride (0.044 g) and (±)-3-(2-oxiranylethyl)pyridine (0.150 g) in dimethylformamide (3 ml) at room temperature to give the title compound as a solid (0.100 g).

m.p. 128–130° C.

MS (EI) 335 (M)+

$^1$H NMR (CDCl$_3$) 8.5(2 H, m); 7.5-7.2(11 H, m); 3.7(1 H, m); 3.2-2.6(4 H, m); 1.8(2 H, m).

EXAMPLE 3

(±)-α-(1-Naphthylthiomethyl)-3-pyridinepropanol

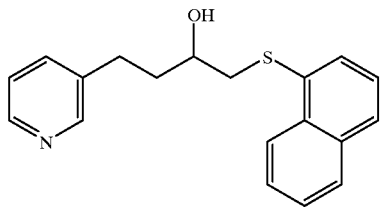

Prepared according to the method described in Example 1 from 1-thionaphthol (0.150 g), sodium hydride (0.044 g) and (±)-3-(2-oxiranylethyl)pyridine (0.150 g) in dimethylformamide (3 ml) at room temperature to give the title compound as an oil (0.100 g).

MS (EI) 310 (M+H)+

$^1$H NMR (CDCl$_3$) 8.5(2 H, m); 7.9-7.1(9 H, m); 3.6(1 H, m); 3.15(1 H, m); 3.0-2.6(3 H, m); 1.8-1.7(2 H, m).

EXAMPLE 4

(±)-α-(4-Phenylmethyl)phenylthiomethyl-3-pyridinepropanol

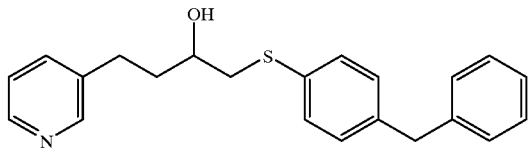

Prepared according to the method described in Example 1 from 4-(phenylmethyl)thiophenol (0.186 g), sodium hydride (0.044 g) and (±)-3-(2-oxiranylethyl)pyridine (0.150 g) in dimethylformamide (3 ml) at room temperature to give the title compound as an oil (0.100 g).

MS (EI) 349 (M)+

$^1$H NMR (CDCl$_3$) 8.45-8.40(2 H, m); 7.47(1 H, d); 7.35-7.0(10 H, m); 3.95(2 H, s); 3.64(1 H, bs); 3.10(1 H, dd); 2.9-2.75(2 H, m); 2.75-2.5(2 H, m); 1.80(2 H, q).

EXAMPLE 5

(±)-α-(2-(5,6,7,8-Tetrahydronaphthyloxy)methyl)-3-pyridinepropanol

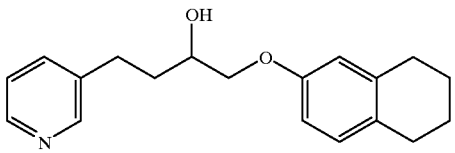

5,6,7,8-Tetrahydro-2-naphthol (0.148 g) was added to a stirred suspension of sodium hydride (0.04 g; 60% dispersion in oil) in dry dimethylformamide (5 ml). After stirring at room temperature for 30 minutes, (±)-3-(2-oxiranylethyl)pyridine (0.15 g; Example 1a) in dry dimethyl sulfoxide-:tetrahydrofuran (2:1, 3 ml) was added. The reaction mixture was heated to 100° C. for 30 minutes, poured into water and extracted with ethyl acetate. The organic phase was washed with water, dried over anhydrous magnesium sulfate and concentrated under reduced pressure. The residue was purified by column chromatography over silica eluting with ethyl acetate to give the title compound as an off-white solid (0.030 g).

m.p. 58–60° C.

MS (EI) 297 (M)+

$^1$H NMR (CDCl$_3$) 8.51(1 H, d); 8.46(1 H, d); 7.55(1 H, d); 7.20(1 H, m); 6.99(1 H, d); 6.67(1 H, m); 6.60(1 H, d); 4.0-3.8(3 H, m); 2.7-3.0(6 H, m); 2.56(1 H, bs); 1.95-1.7(6 H, m).

EXAMPLE 6

(±)-α-(2Naphthyloxymethyl)-3-pyridinepropanol

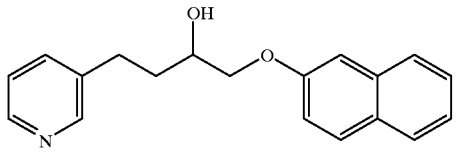

Prepared according to the method described in Example 5 from 2-naphthol (0.150 g), sodium hydride (0.044 g; 60% dispersion in oil) and (±)-3-(2-oxiranylethyl)pyridine (0.150 g) in dimethylformamide at 100° C. for 30 minutes to give the title compound as a solid (0.050 g).

m.p. 93–95° C.

MS (FAB) 294 (M+H)$^+$ $^1$H NMR (CDCl$_3$) 8.5(2 H, m); 7.8-7.1(9 H, m); 4.2-4.0(3 H, m); 3.0-2.7(3 H, m); 1.9(2 H, m).

EXAMPLE 7

(±)-α-(2-(2-Naphthyl)ethyl)-3-pyridinepropanol

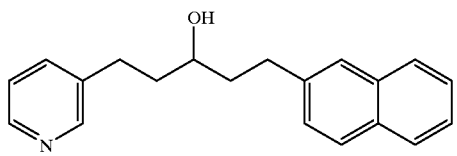

a) (±)-5-(3-Pyridyl)-1-penten-3-ol

Vinyl magnesium bromide (1.0 M in tetrahydrofuran, 40 ml) was added dropwise with stirring under nitrogen to a solution of 3-(3-pyridyl)-1-propionaldehyde (2.70 g; see Example 3 of International Patent Application WO-A-92/19593) in tetrahydrofuran (50 ml) at 0° C. Once addition was complete the reaction was stirred at room temperature for 1 hour before being poured into saturated aqueous ammonium chloride. The mixture was extracted with dichloromethane, the combined extracts dried over anhydrous magnesium sulfate, filtered and concentrated under reduced pressure. The residue was purified by column chromatography over silica eluting with dichloromethane:acetone (4:1) to give the sub-title alcohol as a yellow oil (1.80 g).

MS (EI) 162 (M–H)$^+$ $^1$H NMR (CDCl$_3$) 8.55-8.35(2 H, m); 7.53(1 H, d); 7.25-7.15(1 H, m); 6.0-5.8(1 H, m); 5.35-5.05(2 H, m); 4.2-4.05(1 H, m); 2.85-2.6(2 H, m); 2.0-1.65(3 H, m).

b) 5-(2-Naphthyl)-1-(3-pyridyl)-3-pentanone

Palladium(II) acetate (0.056 g), tri-o-tolylphosphine (0.148 g), 2-bromonaphthalene (0.49 g) and triethylamine (10 ml) were added to a solution of (±)-5-(3-pyridyl)-1-penten-3-ol (0.40 g) in acetonitrile (30 ml) and the mixture heated at 100° C. for 24 hours. The solvents were removed under reduced pressure and water was added to the residue. The mixture was extracted with dichloromethane, the combined extracts dried over anhydrous magnesium sulfate, filtered and concentrated under reduced pressure. The residue was purified by column chromatography over silica eluting with dichloromethane:ethyl acetate (2:1) to give the sub-title ketone as a brown oil (0.327 g).

MS (EI) 289 (M)$^+$ $^1$H NMR (CDCl$_3$) 8.43(2 H, s); 7.9-7.0(9 H, m); 3.05(2 H, t); 2.87(2 H, t); 2.81(2 H, t); 2.73(2 H, m).

c) (±)-5-(2-Naphthyl)-1-(3-pyridyl)-3-pentanol 5-(2-Naphthyl)-1-(3-pyridyl)-3-pentanone (0.327 g) and sodium borohydride were dissolved in ethanol (30 ml) and stirred overnight at room temperature. Water was added to the solution and the mixture extracted with ethyl acetate. The combined extracts were dried over anhydrous magnesium sulfate, filtered and concentrated under reduced pressure. The residue was purified by column chromatography over silica eluting with ethyl acetate:dichloromethane (2:1) to yield the title compound as a white solid (0.117 g).

m.p. 86–7° C.

MS (EI) 291 (M)$^+$ $^1$H NMR (CDCl$_3$) 8.5-8.4(2 H, m); 7.85-7.7(3 H, m); 7.62(1 H, s); 7.55-7.1(5 H, m); 3.75-3.6(1 H, m); 3.05-2.6(4 H, m); 2.0-1.7(4 H, m); 1.65-1.5(1 H, m).

EXAMPLE 8

(±)-5-(2-{6-Hydroxynaphthyl})-1-(3-pyridyl)-3-pentanol hydrochloride salt

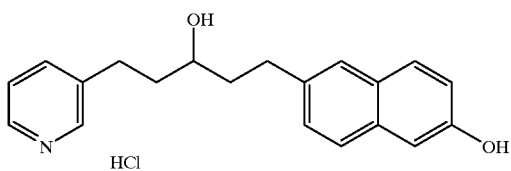

a) 5-(2-{6-Hydroxynaphthyl})-1-(3-pyridyl)-3-pentanone

Prepared according to the method described in Example 7(b) from palladium(II) acetate (0.045 g), tri-o-tolylphosphine (0.122 g), 2-bromo-6-naphthol (0.446 g) and (±)-5-(3-pyridyl)-1-penten-3-ol (0.326 g) in triethylamine (10 ml) and acetonitrile (30 ml) to give the sub-title ketone as a yellow oil (0.180 g).

MS (ESI) 306 (M+H)$^+$ $^1$H NMR (CDCl$_3$) 8.43(1 H, bs); 7.55(1 H, d); 7.47(1 H, d); 7.45(2 H, m); 7.20(2 H, m); 7.15(3 H, m); 3.0(2 H, t); 2.86(2 H, t); 2.84(2 H, t); 2.80(2 H, t).

b) (±)-5-(2-{6-Hydroxynaphthyl})-1-(3-pyridyl)-3-pentanol hydrochloride salt

Prepared according to the method described in Example 7(c) from 5-(2-{6-hydroxynaphthyl})-1-(3-pyridyl)-3-pentanone (0.180 g) and sodium borohydride (0.027 g) in ethanol (20 ml) to give 0.100 g of the title alcohol. This was converted to its hydrochloride salt by adding a solution of the alcohol (0.093 g) in ethanol (1 ml) to ethereal hydrogen chloride (1.0 M, 0.4 ml). Trituration with ether followed by filtration and recrystallisation from isopropyl alcohol gave a white solid (0.075 g).

m.p. 142–144° C.

MS (ESI) 308 ((M–HCl)+H)$^{30}$ $^1$H NMR (DMSO-d$_6$) 9.65(1 H, bs); 8.83(1 H, s); 8.74(1 H, d); 8.45(1 H, d); 7.94(1 H, t); 7.65(1 H, d); 7.58(1 H, d); 7.52(1 H, s); 7.24(1 H, d); 7.05(2 H, dd); 3.44(1 H, bs); 3.0-2.6(4 H, m); 1.9-1.6(4 H, m).

EXAMPLE 9

(±)-α-(2-Naphthylthioethyl)-3-pyridinepropanol

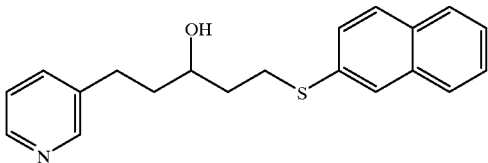

a) 1-(3-Pyridyl)-4-penten-3-one

Aqueous chromic acid (0.66 M, 5 ml) was added to a solution of (±)-5-(3-pyridyl)-1-penten-3-ol (0.500 g; prepared according to the method described in Example 7a) in acetone (30 ml). The mixture was stirred vigorously at room temperature for 6 hours. The solution was then basified by slow addition of saturated aqueous sodium bicarbonate solution. The mixture was extracted with dichloromethane (40 ml), dried over anhydrous magnesium sulfate, filtered and concentrated under reduced pressure to give the crude sub-title α,β-unsaturated ketone (0.200 g) which was used in the following step without further purification.

MS (GCMS; 61% pure) 161 $(M)^+$ b) 1-(3-Pyridyl)-5-(2-naphthylthio)-3-pentanone

2-Thionaphthol was added to a solution of 1-(3-pyridyl)-4-penten-3-one (0.200 g) in ethanol (30 ml) followed by stirring overnight at room temperature. The ethanol was removed under reduced pressure and the residue purified by column chromatography over silica eluting with dichloromethane:ethyl acetate (2:1) to give the sub-title compound as a white solid (0.142 g).

MS (FAB) 322 $(M+H)^+$ $^1$H NMR (CDCl$_3$) 8.42(2 H, s); 7.85-7.65(4 H, m); 7.55-7.35(4 H, m); 7.17(1 H, q); 3.24(2 H, t); 2.88(2 H, t); 2.8-2.7(4 H, m).

c) (±)-α-(Naphthylthioethyl)-3-pyridinepropanol 1-(3-Pyridyl)-5-(2-naphthylthio)-3-pentanone (0.142 g) and sodium borohydride (0.025 g) were dissolved in ethanol (20 ml) and stirred for 15 hours at room temperature. Water was added to the reaction mixture, which was extracted with dichloromethane, the extracts dried over anhydrous magnesium sulfate, filtered and concentrated under reduced pressure. The residue was purified by column chromatography over silica eluting with dichloromethane:ethyl acetate (1:3) to give the title compound as a white solid (0.040 g).

m.p. 58–59° C.

MS (EI) 323 $(M)^+$ $^1$H NMR (CDCl$_3$) 8.45(2 H, m); 7.85-7.7(4 H, m); 7.55-7.40(4 H, m); 7.25-7.15(1 H, m); 3.84(1 H, bs); 3.25-3.05(2 H, m); 2.9-2.6(2 H, m); 1.9-1.7(4 H, m).

EXAMPLE 10

(±)-α-(4-Cyclohexylphenylthiomethyl)-3-pyridinepropanol

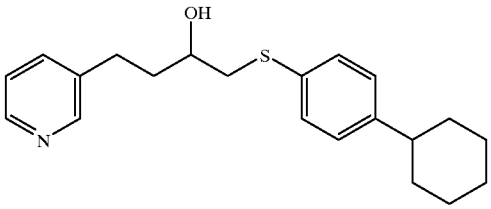

A stirred solution of 1-cyclohexyl-4-(methylthio)benzene (0.48 g; CA 83:96625v) and 1,4-diazabicyclo[2.2.2]octane (0.267 g) in tetrahydrofuran (40 ml) under nitrogen was cooled to −78° C. under nitrogen. n-Butyllithium (1.6 M in hexanes, 2.1 ml) was added dropwise to this with stirring. After stirring for 1 hour at −10° C. and 1 hour at room temperature the mixture was recooled to −78° C. A solution of 3-(3-pyridyl)-1-propionaldehyde (0.645 g) in tetrahydrofuran (10 ml) was then added. Once addition was complete the reaction was stirred for 15 hours at room temperature before being poured into saturated aqueous ammonium chloride. The mixture was extracted with ether (2×50 ml) and ethyl acetate (1×50 ml), the combined extracts dried over anhydrous magnesium sulfate, filtered and concentrated under reduced pressure. The residue was purified by column chromatography over silica eluting with ethyl acetate:dichloromethane (3:1) to give the title compound as a white solid (0.179 g).

m.p.49° C.

MS (ESI) 342 $(M+H)^+$ $^1$H NMR (CDCl$_3$) 8.5-8.4(2 H, m); 7.5(1 H, d); 7.35-7.25(2 H, m); 7.25-7.05(3 H, m); 3.7-3.6(1 H, bs); 3.1(1 H, dd); 2.9-2.75(2 H, m); 2.75-2.6(2 H, m); 2.55-2.4(1 H, m); 1.9-1.7(7 H, m); 1.5-1.2(5 H, m).

EXAMPLE 11

(±)-α-(2-(5,6,7,8-tetrahydronaphthyl)thiomethyl)-3-pyridinepropanol

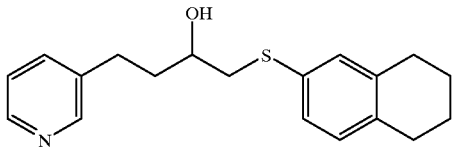

Prepared according to the method described in Example 10 from 2-methylthio-5,6,7,8-tetrahydronaphthalene (0.5 g, CA 89:23960q), 1,4-diazabicyclo[2.2.2]octane (0.291 g), n-butyllithium (1.6 M in hexanes; 1.63 ml) and 3-(3-pyridyl)-1-propionaldehyde (0.350 g) in tetrahydrofuran (100 ml) to give the title compound as a colourless oil (0.155 g).

MS (ESI) 313 $(M)^+$ $^1$H NMR (CDCl$_3$) 8.5-8.4(2 H, m); 7.5-7.4(1 H, m); 7.2-7.15(1 H, m); 7.15-7.05(2 H, m); 6.98(1 H, d); 3.7-3.6(1 H, m); 3.08(1 H, dd); 2.9-2.6(8 H, m); 1.9-1.7(6 H, m).

EXAMPLE 12

(±)-1-(2-Naphthyl)-5-(3-pyridyl)-1-pentyn-3-ol

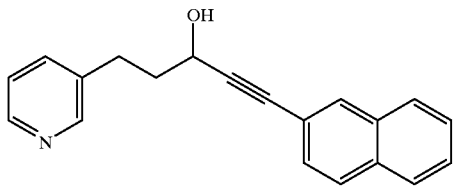

n-Butyllithium (1.6 M in hexanes, 3.0 ml) was added to a solution of 2-ethynylnaphthalene (0.72 g) in tetrahydrofuran (40 ml) at −60° C. After stirring for 15 minutes a solution of 3-(3-pyridyl)-1-propionaldehyde (0.65 g) in tetrahydrofuran (10 ml) was added at −60° C. The solution was allowed to warm to room temperature with stirring over 1 hour. Saturated aqueous ammonium chloride (100 ml) was added and the mixture extracted with ethyl acetate (2×75 ml). The combined organic extracts were dried over anhydrous magnesium sulfate, filtered and concentrated under reduced pressure. The residue was purified by column chromatography over silica eluting with acetone:hexane (1:9) then acetone:hexane (3:7) to give the title compound as an oil (0.71 g).

MS (ESI+Loop) 288 (M+H)$^+$ $^1$H NMR (CDCl$_3$) 8.55(1 H, s); 8.5-8.45(1 H, m); 7.94(1 H, s); 7.85-7.7(3 H, m); 7.62-7.55(1 H, m); 7.55-7.43(3 H, m); 7.3-7.2(1 H, m); 4.65(1 H, t); 2.91(2 H, t); 2.25-2.1(2 H, m).

EXAMPLE 13

(±)-α-(5-(2,3-Dihydro-1H-indenyloxy)methyl)-3-pyridinepropanol

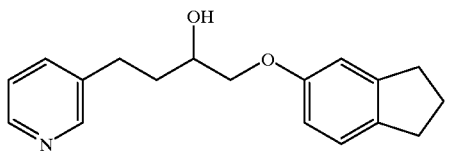

Prepared according to the method described in Example 5 from 2,3-dihydro-1H-inden-2-ol (0.15 g), sodium hydride (0.044 g) and (±)-3-(2-oxiranylethyl)pyridine (0.15 g) in dimethylformamide (3 ml) at 100° C. for 30 minutes to give the title compound as a white solid (0.11 g).

m.p. 73–75° C.

MS (ESI+loop) 284 (M+H)$^+$ $^1$H NMR (CDCl$_3$) 8.55-8.4(2 H, m); 7.55(1 H, d); 7.3-7.15(1 H, m); 7.10(1 H, m); 6.78(1 H, s); 6.67(1 H, dd); 4.05-3.9(2 H, m); 3.4-3.35(1 H, m); 3.0-2.7(6 H, m); 2.5-2.4(1 H, m); 2.15-2.0(2 H, m); 2.0-1.75(2 H, m).

EXAMPLE 14

(±)-α-(2-(6-(2-Propenyloxy)naphthyloxy)methyl)-3-pyridinepropanol

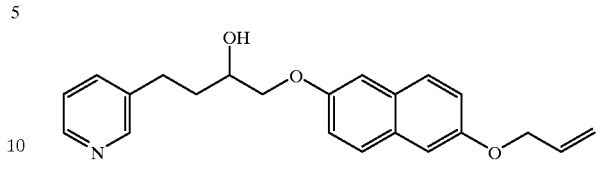

Prepared according to the method described in Example 5 from 6-(2-propenyloxy)naphthalen-2-ol (0.22 g, European Patent Application EP-A-0 221 677), sodium hydride (0.044 g) and (±)-3-(2-oxiranylethyl)pyridine (0.15 g) in dimethylformamide (5 ml) at 100° C. for 30 minutes to give the title compound as a white solid (0.04 g).

m.p. 102–103° C.

MS (ESI+loop) 350 (M+H)$^+$ $^1$H NMR(CDCl$_3$) 8.6-8.4(2 H, m); 7.7-7.55(3 H, m); 7.3-7.0(5 H, m); 6.2-6.05(1 H, m); 5.46(1 H, dd); 5.32(1 H, dd); 4.62(2 H, d); 4.15-3.9(3 H, m); 3.0-2.7(2 H, m); 2.55(1 H, bs); 2.05-1.85(2 H, m).

EXAMPLE 15

(±)-α-(4-(4-Hydroxyphenylmethyl)phenoxymethyl)-3-pyridinepropanol

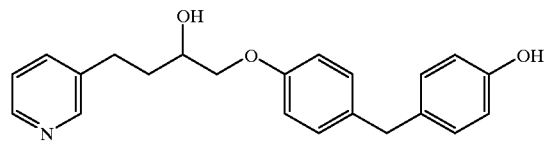

Prepared according to the method described in Example 5 from bis(4-hydroxyphenyl)methane (1.6 g), (±)-3-(2-oxiranylethyl)pyridine (1.24 g) and sodium hydride (60% dispersion in oil; 0.319 g) in dimethylformamide (25 ml) at 100° C. for 2 hours to give the title compound as a white solid (0.587 g).

m.p. 98–99° C.

MS (FAB) 350 (M+H)$^+$ $^1$H NMR (CDCl$_3$) 8.50(1 H, s); 8.45(1 H, d); 7.57(1 H, d); 7.3-7.2(1 H, m); 7.07(2 H, d); 7.01(2 H, d); 6.85-6.7(4 H, m); 6.00(1 H, bs); 4.05-3.9(2 H, m); 3.84(2 H, s); 3.85-3.8(1 H, m); 2.95-2.85(1 H, m); 2.82-2.7(1 H, m); 2.45(1 H, bs); 2.0-1.8(2 H, m).

EXAMPLE 16

(±)-α-(4-(4-Hydroxyphenoxy)phenoxymethyl)-3-pyridinepropanol

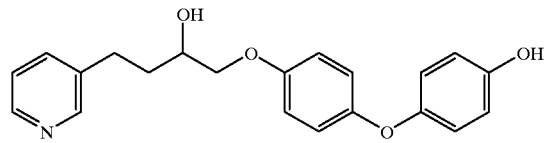

Prepared according to the method described in Example 5 from 4,4'-dihydroxydiphenyl ether (1.68 g), (±)-3-(2- oxiranylethyl)pyridine (1.24 g) and sodium hydride (60% dispersion in oil; 0.319 g) in dimethylformamide (20 ml) at 100° C. for 2 hours to give the title compound as a white solid (0.41 g).

m.p. 89–91° C.

MS (FAB) 351 (M+H)+

$^1$H NMR (CDCl$_3$) 8.50(1 H, d); 8.45(1 H, d); 7.59(1 H, d); 7.3-7.2(1 H, m); 6.95-6.75(8 H, m); 6.30(1 H, bs); 4.05-3.95(2 H, m); 3.85-3.8(1 H, m); 3.0-2.85(1 H, m); 2.85-2.75(1 H, m); 2.46(1 H, bs); 2.0-1.8(2 H, m).

EXAMPLE 17

(±)-5-(6-Methoxy-2-naphthyl)-1-(3-pyridyl)pentan-3-ol

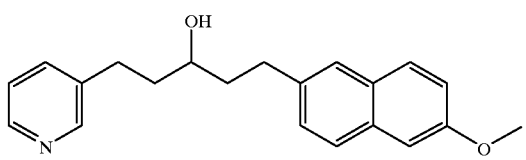

a) 5-(6-Methoxy-2-naphthyl)ethyl-1-(3-pyridyl)-1-penten-3-one

Aqueous sodium hydroxide (1 M, 1 ml) was added to a solution of 4-(6-methoxy-2-naphthyl)butan-2-one (nabumetone; 0.228 g) and pyridine-3-carboxaldehyde (0.107 g) in ethanol (10 ml) and the mixture stirred at room temperature for 2 hours. The solution was acidified with dilute hydrochloric acid then basified with a solution of sodium bicarbonate. The aqueous mixture was extracted with dichloromethane, the combined extracts dried over anhydrous magnesium sulfate, filtered and concentrated under reduced pressure. The residue was purified by column chromatography over silica eluting with ethyl acetate-:dichloromethane (1:5) to give the sub-title compound as a solid (0.10 g).

m.p. 127–129° C.

MS ESI+loop) 364 (M+acetate)+

$^1$H NMR (CDCl$_3$) 8.73(1 H, d); 8.60(1 H, dd); 7.83(1 H, dt); 7.7-7.5(4 H, m); 7.35-7.3(2 H, m); 7.1-7.15(2 H, m); 6.80(1 H, d); 3.91(3 H, s); 3.0–3.2(4 H, m).

b) (±)-5-(6-Methoxy-2-naphthyl)ethyl-1-(3-pyridyl)-3-pentanol

A mixture of ammonium formate (2.0 g), palladium on charcoal (10%; 0.5 g) and 5-(6-methoxy-2-naphthyl)ethyl-1-(3-pyridyl)-1-penten-3-one (0.7 g) in ethanol (50 ml) was heated at reflux for 5 minutes. The reaction mixture was then filtered through Celite and concentrated under reduced pressure. The residue was purified by column chromatography over silica eluting with ethyl acetate:dichloromethane (1:5) to give 5-(6methoxy-2-naphthyl)ethyl-1-(3-pyridyl)-3-pentanone (0.3 g). The latter (0.2 g) was dissolved in ethanol (20 ml) and solid sodium borohydride (0.1 g) was added over 10 minutes. The solution was concentrated under reduced pressure and the residue was purified by column chromatography over silica eluting with ethyl acetate to give the title compound as a solid (0.1 g).

m.p. 83–84° C.

MS (EI) 321(M)+

$^1$H NMR (CDCl$_3$) 8.46(1 H, s); 8.43(1 H, d); 7.67(2 H, dd); 7.55(1 H, s); 7.48(1 H, dt); 7.31-7.25(1 H, m); 7.2-7.1(3 H, m); 5.30(1 H, s); 3.92(3 H, s); 3.75-3.65(1 H, m); 2.98-2.75(3 H, m); 2.73-2.62(1 H, m); 1.95-1.75(4 H, m).

EXAMPLE 18

(±)-α-(2-(7-Hydroxy)naphthyloxymethyl)-3-pyridinepropanol

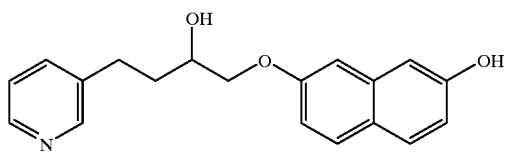

Prepared according to the method described in Example 5 from 2,7-naphthalenediol (1.0 g), sodium hydride (60% dispersion in oil; 0.270 g) and (±)-3-(2-oxiranylethyl)pyridine (1.0 g) in dimethylformamide at room temperature to yield the title compound as a solid (0.390 g).

m.p. 144–147° C.

MS (EI) 309 (M)+

$^1$H NMR (DMSO-d$_6$) 9.64(1 H, s); 8.47(1 H, d); 8.42-8.38(1 H, m); 7.70-7.60(3 H, m), 7.35-7.28(1 H, m); 7.07(1 H, d); 7.00(1 H, d); 6.95-6.85(2 H, m); 5.09(1 H, d); 4.02(2 H, d); 3.90-3.78(1 H, m); 2.90-2.75(1 H, m); 2.75-2.65(1 H, m); 1.95-1.83(1 H, m); 1.82-1.70(1 H, m)

EXAMPLE 19

(±)-α-(2-(7-(2-Propenyloxy)naphthyloxymethyl)-3-pyridinepropanol

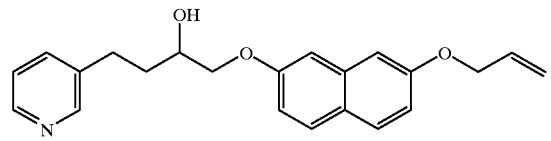

Prepared according to the method described in Example 5 from 2-(2-propenyloxy)-7-hydroxynaphthalene (1.27 g; *J. Org. Chem.*, (1981) 46, 4988), sodium hydride (60% dispersion in oil; 0.25 g) and (±)-3-(2-oxiranylethyl)pyridine (1.0 g) in dimethylformamide (20 ml) at room temperature to yield the title compound as an oil (0.410 g).

MS (EI) 349 (M)+

$^1$H NMR (CDCl$_3$) 8.53(1 H, s); 8.47(1 H, d); 7.70-7.60(2 H, m); 7.58(1 H, d); 7.25-7.20(2 H, m); 7.10-6.95(4 H, m); 6.20-6.05(1 H, m); 5.46(1 H, dd); 5.32(1 H, dd); 4.70-4.60(2 H, m); 4.15-4.02(2 H, m); 4.02-3.95(1 H, m); 3.0-2.9(1 H, m); 2.85-2.75(1 H, m); 2.0-1.85(2 H, m).

EXAMPLE 20

(±)-α-(2-(6-(2-Propynyloxy))naphthyloxymethyl)-3-pyridinepropanol

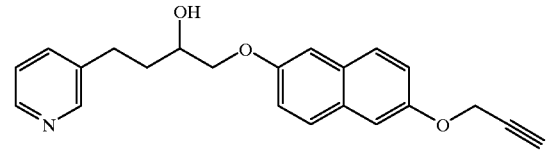

a) 6-(3-Propynyloxy)naphthol

Solid 2,6-dihydroxynaphthalene (3.95 g) followed by propargyl bromide (80 wt % solution in toluene; 1.4 ml) was added to a suspension of potassium carbonate (1.7 g) in acetone (50 ml). The mixture was heated at reflux for 3 hours, cooled and left to stand overnight. The reaction was partitioned between ether (250 ml) and 5% aqueous hydrochloric acid (50 ml). The separated ethereal layer was washed with brine, dried over anhydrous magnesium sulfate and concentrated under reduced pressure. The residue was purified by column chromatography over silica eluting with petroleum ether (b.p. 40–60° C.):ethyl acetate (3:1) to give the sub-title compound as an oil (1.21 g).

MS (EI) 198 (M)$^+$
$^1$H NMR (CDCl$_3$) 7.65(1 H, d); 7.59(1 H, d); 7.05-7.25(4 H, m); 5.33(1 H, s); 4.82(2 H, s); 2.50(1 H, s).

b) (±)-1-(2-(6-(2-Propynyloxy))naphthyloxy)-4-(3-pyridyl)butan-2-ol

A solution of (±)-3-(2-oxiranylethyl)pyridine (0.452 g; from Example 1a) above) in dimethylformamide (2 ml) was added to a solution of 6-(3-propynyloxy)naphthol (1.20 g) and 1,4-diazabicyclo[2.2.2]octane (1 spatula end) in dimethylformamide (10 ml). The mixture was heated at 120° C. for 4 hours. After cooling the reaction was added to water (100 ml) and extracted with diethyl ether (3×100 ml). The combined organic extracts were washed with brine, dried over anhydrous magnesium sulfate, filtered and concentrated under reduced pressure. The residue was purified by column chromatography over silica eluting with dichloromethane:ethanol (98:2) then (97:3) then (95:5) to give a white solid (0.442 g).

m.p. 79–82° C.
MS (EI) 347 (M)$^+$
$^1$H NMR (DMSO-d$_6$) 8.47(1 H, d); 8.40(1 H, dd); 7.75-7.65(3 H, m); 7.35-7.25(3 H, m); 7.18-7.10(2 H, m); 5.10(1 H, d); 4.86(2 H, d); 3.96(2 H, d); 3.95-3.75(1 H, m); 3.59(1 H, t); 2.9-2.75(1 H, m); 2.75-2.65(1 H, m); 1.95-1.85(1 H, m); 1.8-1.7(1 H, m).

EXAMPLE 21A (2R)-α-(2-(6-(2-Propynyloxy))naphthyloxymethyl)-3-pyridinepropanol

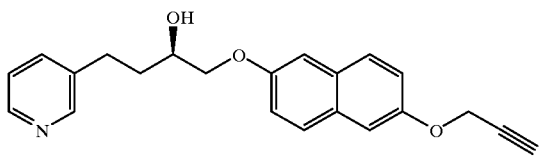

a) (2S)-5-Oxo-1-(2-oxo-2-phenylacetyl)pyrrolidine-2-carboxylic acid tert-butyl ester Benzoylformic acid (7.09 g) was dissolved in dichloromethyl methyl ether (30 ml) and the solution was heated at 55° C. for 2 hours 30 minutes. The excess ether was removed under reduced pressure and the residue dissolved in toluene (50 ml). Solid (−)-pyroglutamic acid tert-butyl ester (7.84 g; J. Med. Chem., (1985) 28, 1596) was added to a suspension of sodium hydride (60% dispersion in oil; 2.00 g) in toluene and the mixture stirred at room temperature for 30 minutes. The acid chloride solution generated above was then slowly added and stirring was continued for 4 hours. Wet tetrahydofuran (300 ml) was then added to the reaction. The organic solution was washed with saturated aqueous sodium bicarbonate (3×100 ml) and then brine (100 ml). The solution was dried over anhydrous magnesium sulfate, filtered and concentrated under reduced pressure. The residue was purified by column chromatography over silica eluting with hexane:acetone (3:1) and was recrystallised from toluene:hexane (1:5) to give a white solid (9.37 g).

m.p. 102° C.
MS (EI) 261 (M−56)$^+$
$^1$H NMR (CDCl$_3$) 8.0(2 H, bs); 7.65(1 H, bs); 7.50(2 H, bs); 4.8-4.7(1 H, m); 2.75-2.4(3 H, m); 2.3-2.2(1 H, m); 1.5-1.6(9 H, m).

b) (2S)-5-Oxo-1-(2-oxo-2-phenylacetyl)pyrrolidine-2-carboxylic acid

Trifluoroacetic acid (40 ml) was added to a solution of 5-oxo-1-(2-oxo-2-phenylacetyl)pyrrolidine-2-carboxylic acid tert-butyl ester (5.00 g) in dichloromethane (40 ml) and the solution was stirred for 2 hours. All volatiles were removed under reduced pressure and the residue triturated with ether:hexane (1:1). The white solid was collected by filtration and washed with hexane to give the sub-title compound (4.09 g).

m.p. 151–152° C.
MS (EI) 261 (M−Bu+H)$^+$
$^1$H NMR (CDCl$_3$) 7.95(2 H, dd); 7.7-7.6(1 H, m); 7.6-7.5(2 H, m); 4.95-4.9(1 H, m); 4.9(1 H, bs); 2.8-2.55(3 H, m); 2.45-2.35(1 H, m).

c) 5-Oxo-1-(2-oxo-2-phenylacetyl)pyrrolidine-2-carboxylic acid 1-(2-(6-(2-propynyloxy))naphthyloxymethyl)-3-(3-pyridyl)propyl ester A solution of (±)-α-(2-(6-(3-propynyloxy))naphthyloxymethyl)-3-pyridinepropanol (1.37 g), (2S)-5-oxo-1-(2-oxo-2-phenylacetyl)pyrrolidine-2-carboxylic acid (2.06 g), 4-dimethylaminopyridine (0.90 g) and 1-[3-(dimethylamino)propyl]-3-ethylcarbodiimide hydrochloride (1.5 g) in dichloromethane (40 ml) was stirred for 72 hours. The reaction mixture was concentrated under reduced pressure and the residue purified twice by column chromatography over silica eluting with ethyl acetate/hexane (3:1). Two products were obtained, a less polar product (0.81 g), more polar product (1.25 g) both as oils.

Less polar product:
MS (APCI) 591 (M+H)$^+$
$^1$H NMR (DMSO-d$_6$) 8.48(1 H, s); 8.42(1 H, d); 7.91(1 H, d); 7.8-7.65(4 H, m); 7.60(2 H, t); 7.35-7.28(3 H, m); 7.15(2 H, qd); 5.42-5.32(1 H, m); 5.04(1 H, dd); 4.87(2 H, d); 4.4-4.3(1 H, m); 4.3-4.2(1 H, m); 3.59(1 H, t); 2.9-2.5(5 H, m); 2.2-2.05(3 H, m).

More polar product:
MS (APCI) 591 (M+H)$^+$
$^1$H NMR (DMSO-d$_6$) 8.46(1 H, s); 8.41(1 H, d); 7.8-7.55(6 H, m); 7.35-7.28(3 H, m); 7.15(2 H, td); 5.39(1 H, bs); 5.05-5.0(1 H, m); 4.87(2 H, s); 4.4-4.3(1 H, m); 4.3-4.2(1 H, m); 3.59(1 H, s); 2.85-2.55(5 H, m); 2.25-2.05(3 H, m).

d) (R)-α-(2-(6-(2-propynyloxy))naphthyloxymethyl)-3-pyridinepropanol

A solution of 5-oxo-1-(2-oxo-2-phenylacetyl)pyrrolidine-2-carboxylic acid 1-(2-(6-(3-propynyloxy))naphthyloxymethyl)-3-(3-pyridyl)propyl ester (0.80 g; more polar product from step (c) above) and potassium carbonate (0.56 g) in 70% aqueous methanol (15 ml) was stirred at room temperature for 2 hours. A white precipitate formed and was removed by filtration. This was dried overnight under vacuum to give a white solid (0.36 g).

m.p. 120° C.
MS (APCI) 348 (M+H)$^+$
$^1$H NMR (DMSO-d$_6$) 8.48(1 H, s); 8.39(1 H, d); 7.75-7.65(3 H, m); 7.35-7.25(3 H, m); 7.2-7.1(2 H, m); 5.10(1 H, d); 4.87(2 H, d); 3.97(2 H, d); 3.9-3.75(1 H, m); 3.59(1 H, d); 2.90-2.75(1 H, m); 2.75-2.65(1 H, m); 2.0-1.83(1 H, m); 1.83-1.7(1 H, m).

EXAMPLE 21B (S)-α-(2-(6-(2-Propynyloxy))naphthyloxymethyl)-3-pyridinepropanol

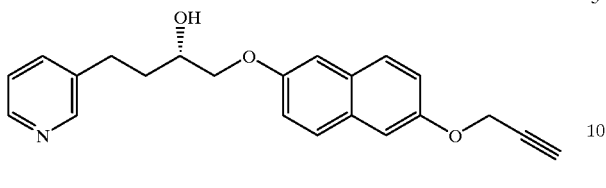

Prepared according to the method described in Example 21A d) by hydrolysis of 5-oxo-1-(2-oxo-2-phenylacetyl) pyrrolidine-2-carboxylic acid 1-(2-(6-(2-propynyloxy)) naphthyloxymethyl)-3-(3-pyridyl)propyl ester (0.86 g, the less polar product of Example 21A(c)) to give a white solid (0.42 g).

m.p. 118° C.

MS (APCI) 348 (M+H)$^+$ $^1$H NMR (DMSO-d$_6$) 8.48(1 H, s); 8.39(1 H, d); 7.75-7.65(3 H, m); 7.35-7.25(3 H, m); 7.2-7.1(2 H, m); 5.10(1 H, d); 4.87(2 H, d); 3.97(2 H, d); 3.9-3.75(1 H, m); 3.59(1 H, d); 2.90-2.75(1 H, m); 2.75-2.65(1 H, m); 2.0-1.83(1 H, m); 1.83-1.7(1 H, m).

EXAMPLE 22

(±)-α-(2-(6-Propoxy)naphthyloxymethyl)-3-pyridinepropanol

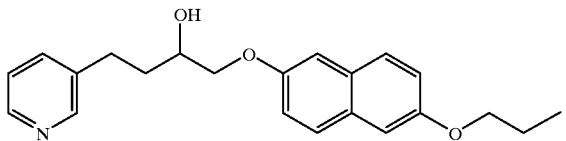

(±)-α-(2-(6-(2-Propenyloxy)naphthyloxy)methyl)-3-pyridinepropanol (0.17 g; Example 14) was dissolved in dry ethanol (10 ml) and hydrogenated for 2 hours at 1.5 atmospheres pressure using palladium on carbon (10%, 1 spatula end) as catalyst. The reaction was filtered through Celite and the residue washed with ethanol. The combined filtrate and washings were concentrated under reduced pressure and the residue obtained purified by column chromatography over silica eluting with dichloromethane:ethanol (95:5) to give a white solid (0.071 g).

m.p. 94–96° C.

MS (EI) 351 (M)$^+$ $^1$H NMR (DMSO-d$_6$) 8.47(1 H, s); 8.40(1 H, d); 7.75-7.6(3 H, m); 7.35-7.29(1 H, m); 7.25(2 H, s); 7.15-7.08(2 H, m); 5.09(1 H, d); 4.05-3.9(4 H, m); 3.9-3.8(1 H, m); 2.9-2.75(1 H, m); 2.75-2.65(1 H, m); 1.95-1.7(4 H, m); 1.03(3 H, m).

EXAMPLE 23

(±)-1-(4'-Hydroxybiphenyl-4-yl)-5-(3-pyridyl)-3-pentanol

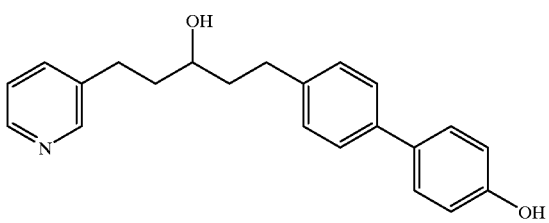

a) 1-(4'-Hydroxybiphenyl-4-yl)-5-(3-pyridyl)-3-pentanone

Prepared according to the method described in Example 7b) from palladium(II) acetate (0.18 g), tri-o-tolylphosphine (0.49 g), 4'-bromobiphenyl-4-ol (2 g) and (±)-5-(3-pyridyl)-1-penten-3-ol (1.3 g; from Example 7a) above) in triethylamine (20 ml) and acetonitrile (60 ml) to give the sub-title ketone as a yellow oil (0.524 g).

MS (EI) 331 (M)$^+$ $^1$H NMR (DMSO-d$_6$) 9.5(1 H, s); 8.43(1 H, d); 8.39(1 H, d); 7.61(1 H, dt); 7.48-7.43(4 H, m); 7.27(1 H, q); 7.21(2 H, d); 6.83(2 H, d); 2.85-2.75(8 H, m)

b) (±)-1-(4'-Hydroxybiphenyl-4-yl)-5-(3-pyridyl)-3-pentanol

Prepared according to the method described in Example 7c) from 1-(4'-hydroxybiphenyl-4-yl)-5-(3-pyridyl)-3-pentanone (0.52 g) and sodium borohydride (0.062 g) in ethanol (10 ml) to give a yellow gum, which was purified by column chromatography over silica eluting with ethanol-:ethyl acetate (1:9) to give the title compound as a yellow gum that solidified on standing (0.39 g).

m.p. 140–143° C.

MS (ESI) 334 (M+H)$^+$ $^1$H NMR (DMSO-d$_6$) 9.53(1 H, s); 8.45(1 H, d); 8.36(1 H, d); 7.60(1 H, d); 7.5-7.4(4 H, m); 7.29(1 H, q); 7.21(2 H, d); 6.82(2 H, d); 4.65(1 H, d); 3.5-3.38(1 H, m); 2.8-2.55(4 H, m); 1.78-1.55(4 H, m).

EXAMPLE 24

(±)-1-(4'-(2-Propenyl)biphenyl-4-yloxy)-4-(3-pyridyl)-2-butanol

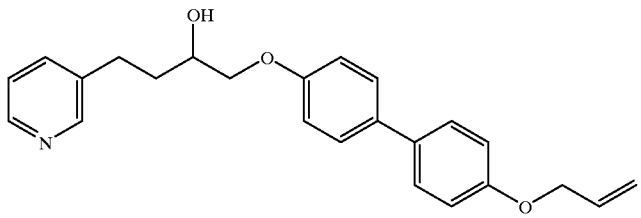

a) (±)-α-(Chloromethyl)-3-pyridinepropanol

A solution of 3-picoline (19.4 ml) in dry tetrahydrofuran was added to a solution of lithium diisopropylamide in tetrahydrofuran at −10° C. under a nitrogen atmosphere (prepared by adding n-butyllithium (2.5 M in hexanes, 80 ml) to a solution of diisopropylamine (28 ml) in dry tetrahydrofuran (80 ml)). The resulting bright yellow suspension was stirred at −10° C. for 1 hour, and was then transferred via a double ended needle to a solution of (±)-epichlorohydrin (15.6 ml) in tetrahydrofuran (80 ml) at −10° C. under nitrogen. After addition the mixture was stirred and allowed to warm up to room temperature over 1 hour. The reaction was quenched by addition of a solution of saturated aqueous ammonium chloride (200 ml) and was then made acidic by addition of hydrochloric acid (2 M) whilst keeping the temperature below 20° C. The mixture was stirred at ambient temperature for 1 hour, and then re-basified by the addition of solid sodium bicarbonate. The product was extracted with ethyl acetate, the combined extracts washed with brine, dried over anhydrous magnesium sulfate, filtered and concentrated under reduced pressure. The residue was purified by column chromatography over silica eluting with dichloromethane:ethanol (95:5) to give the sub-title compound as a yellow oil (9.66 g).

MS (EI) 185 (M)+

$^1$H NMR (DMSO-$d_6$) 8.43(1 H, d); 8.4(1 H, dd); 7.63(1 H, dd); 7.35-7.27(1 H, m); 5.22(1 H, d); 3.65-3.5(3 H, m); 2.8-2.55(2 H, m); 1.85-1.6(2 H, m).

b) (±)-1-(4'-(2-Propenyl)biphenyl-4-yloxy)-4-(3-pyridyl)-2-butanol

A solution of 4'-(2-propenyl)biphenyl4-ol (1.22 g; Biochemistry 1987, 26(18), 5908) in ethanol (10 ml) at room temperature was treated with a solution of sodium hydroxide (0.215 g) in water (5 ml) and was then heated at reflux. A solution of (±)-α-(chloromethyl)-3-pyridinepropanol (1.0 g) in ethanol (5 ml) was added to the latter and the resulting mixture heated at reflux for 2 hours. The reaction mixture was cooled and then concentrated under reduced pressure. The residue was purified by column chromatography over silica eluting with dichloromethane:ethanol (95:5) to give a solid. Trituration with diethyl ether:methanol (9:1) gave the title compound as a colourless solid (0.256 g).

m.p. 139–141° C.

MS (EI) 375 (M)+

$^1$H NMR (DMSO-$d_6$) 8.45(1 H, d); 8.40(1 H, dd); 7.66(1 H, d); 7.6-7.5(4 H, m); 7.35-7.28(1 H, m); 7.05-6.95(4 H, m); 6.13-6.0(1 H, m); 5.41(1 H, dd); 5.28(1 H, dd); 5.07(1 H, d); 4.59(2 H, d); 3.90(2 H, d); 3.85-3.75(1 H, m); 2.85-2.63(2 H, m); 1.92-1.65(2 H, m).

EXAMPLE 25

(±)-1-(Biphenyl-4-yloxy)-4-(3-pyridyl)-2-butanol

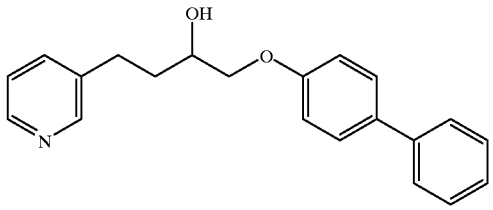

Prepared according to the method described in Example 24b) from 4-phenylphenol (0.916 g), ethanol (10 ml), sodium hydroxide (0.215 g), water (5 ml) and (±)-α-(chloromethyl)-3-pyridinepropanol (1.0 g; from Example 24a) above) to give a yellow oil. This was purified by column chromatography over silica eluting with dichloromethane:ethanol (95:5) to give the title compound as a pale yellow gum which solidified on standing (0.307 g).

m.p. 83–86° C.

MS (EI) 319 (M)+

$^1$H NMR (CDCl$_3$) 8.53(1 H, d); 8.4(1 H, d); 7.58-7.50(5 H, m); 7.43(2 H, t); 7.32(1 H, t); 7.24(1 H, dd); 6.96(2 H, d); 4.13-4.02(1 H, m); 4.05(1 H, dd); 3.91(1 H, dd); 2.96-2.89(1 H, m); 2.96-2.75(1 H, bm); 2.84-2.76(1 H, m); 1.99-1.86(2 H, m).

EXAMPLE 26

(2S)-1-(Biphenyl-4-yloxy)-4-(3-pyridyl)-2-butanol

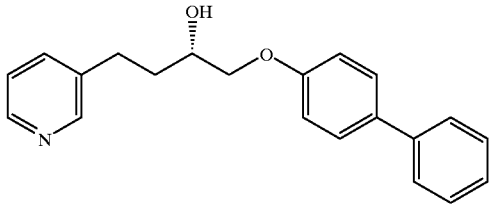

a) (2S, 3E/Z)-4-(3-Pyridyl)-1,2-O-isopropylidenebut-3-ene-1,2-diol

A solution of n-butyllithium (2.5 M in hexanes; 12 ml) was added dropwise to a stirred suspension of 3-pyridylmethyltriphenylphosphonium chloride hydrochloride (6.39 g, J. Med. Chem. 1986, 29, 1461) in tetrahydrofuran (50 ml) at −40° C. The resulting mixture was stirred at room temperature for 30 minutes and was then cooled to −70° C. A solution of 2,3-O-(R)-isopropylidene-D-glyceraldehyde (1.82 g) (ex Oxford Asymmetry; see *Organic Synthesis* (1995) 72, 6) in tetrahydrofuran (10 ml) was added. The resulting mixture was stirred and allowed to reach room temperature over 3 hours. The mixture was poured into brine (200 ml) and extracted into ethyl acetate. The combined extracts were dried over anhydrous magnesium sulfate, filtered and concentrated under reduced pressure. The residue was purified by column chromatography over silica eluting with diethyl ether to give the sub-title compound as an oil (2.24 g).

MS (EI) 205 (M)+

$^1$H NMR (CDCl$_3$) major Z-diastereomer 8.53(2 H, d); 7.61(1 H, dt); 7.29(1 H, dd); 6.67(1 H, d); 5.85(1 H, dd); 4.83(1 H, q); 4.16(1 H, t); 3.71(1 H, t); 1.49(3 H, s); 1.39(3 H, s).

b) (2S)-4-(3-Pyridyl)-1,2-O-isopropylidenebutane-1,2-diol

The compound from part a) (2.2 g) was dissolved in ethyl acetate (30 ml) and hydrogenated for 2 hours at 3 atmospheres pressure using palladium on carbon (10%, 1 spatula end) as catalyst. The reaction was filtered through Celite and the residue washed with ethyl acetate. The combined filtrate and washings were concentrated under reduced pressure and the residue obtained purified by column chromatography over silica eluting with diethyl ether to give the sub-title compound as an oil (2.14 g).

MS (ESI) 208 (M+H)+

$^1$H NMR (CDCl$_3$) 8.48-8.45(2 H, m); 7.52(1 H, dt); 7.23(1 H, dd); 4.10(1 H, quintet); 4.04(1 H, t); 3.55(1 H, t); 2.84-2.64(2 H, m); 1.94-1.80(2 H, m); 1.44(3 H, s); 1.36(3 H, s).

c) (2S)-4-(3-Pyridyl)-1,2-butanediol

The compound from part b) (19.6 g) was dissolved in 2 N hydrochloric acid (100 ml) and was stirred for 40 minutes. The mixture was neutralised with saturated aqueous sodium hydrogencarbonate solution and was concentrated under reduced pressure. The residue obtained was triturated with ethyl acetate and filtered. The residue was washed with ethyl acetate and the combined organic extracts were dried over anhydrous magnesium sulfate, filtered and concentrated under reduced pressure. The residue obtained was purified by column chromatography over silica eluting with ethyl acetate:methanol (9:1) to give the sub-title compound as an oil (13.21 g).

MS (APCI) 168 (M+H)+

$^1$H NMR (CDCl$_3$) 8.44-8.40(2 H, m); 7.54(1 H, d); 7.22(1 H, dd); 3.73-3.67(1 H, m); 3.65(1 H, dd); 3.48(1 H, dd); 2.90-2.70(2 H, bm); 2.87-2.68(2 H, m); 1.84-1.67(2 H, m).

d) (2S)-2-(tert-Butyldimethylsilyloxy)-4-(3-pyridyl)-1-butyl para-toluenesulfonate The compound from part c) (5.00 g) was dissolved in pyridine (30 ml) and solid para-toluenesulfonyl chloride (8.60 g) added. The resulting mixture was stirred at room temperature for 20 hours and then concentrated under reduced pressure. The residue was partitioned between ethyl acetate and a solution of saturated aqueous sodium hydrogencarbonate. The organic extract was dried over anhydrous magnesium sulfate, filtered and concentrated under reduced pressure. The resulting oil was dissolved in dimethylformamide (20 ml) and imidazole (3.4 g) followed by tert-butyldimethylsilyl chloride (5.25 g) were added. The mixture was stirred for 20 hours and was then poured into water (200 ml). The mixture was extracted with ethyl acetate and the combined organic extracts dried over anhydrous magnesium sulfate, filtered and concentrated under reduced pressure. The residue obtained was purified by column chromatography over silica eluting with diethyl ether to give the sub-title compound as an oil (8.22 g).

MS (APCI) 436 (M+H)+

$^1$H NMR (CDCl$_3$) 8.40(1 H, d); 8.35(1 H, s); 7.73(2 H, d); 7.40(1 H, d); 7.29(2 H, d); 7.16(1 H, dd); 3.90-3.83(1 H, m); 3.86(2 H, s); 2.64-2.48(2 H, m); 2.40(3 H, s); 1.82-1.65 (2 H, m); 0.82(9 H, s); 0.01(3 H, s); −0.19(3 H, s).

e) (2S)-4-(3-Pyridyl)-1-[(4-phenyl)phenoxy]-butan-2-ol

Solid 4-phenylphenol (0.43 g) was added to a stirred suspension of sodium hydride (60%, 0.096 g) in dimethylformamide (5 ml) and the resulting solution stirred for 30 minutes. (2S)-2-(tert-Butyldimethylsilyloxy)-4-(3-pyridyl)-1-butyl para-toluenesulfonate (0.84 g) was added and the mixture stirred at 60° C. for 2 hours. After cooling the mixture was poured into water (50 ml) and extracted with ethyl acetate. The combined organic extracts were dried over anhydrous magnesium sulfate, filtered and concentrated under reduced pressure. The residue obtained was dissolved in acetonitrile (10 ml) and hydrofluoric acid (40%; 1 ml) was added. The mixture was stirred for 1 hour and then poured into a solution of saturated aqueous sodium hydrogencarbonate. The mixture was extracted with ethyl acetate and the combined organic extracts were dried over anhydrous magnesium sulfate, filtered and concentrated under reduced pressure to give the title compound (0.434 g) as a solid that was recrystallised from ethyl acetate:hexane.

m.p. 104–106° C.

MS (APCI) 320 (M+H)+

$^1$H NMR (CDCl$_3$) 8.53(1 H, d); 8.4(1 H, d); 7.58-7.50(5 H, m); 7.43(2 H, t); 7.32(1 H, t); 7.24(1 H, dd); 6.96(2 H, d); 4.13-4.02(1 H, m); 4.05(1 H, dd); 3.91(1 H, dd); 2.96-2.89 (1 H, m); 2.96-2.75(1 H, bm); 2.84-2.76(1 H, m); 1.99-1.86(2 H, m).

EXAMPLE 27

(2R)-1-(Biphenyl-4-yloxy)-4-(3-pyridyl)-2-butanol

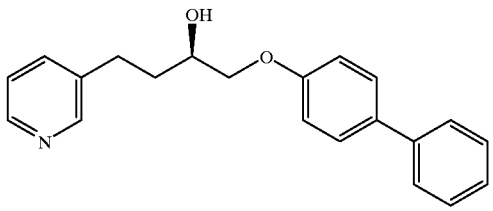

Diethyl azodicarboxylate (0.123 ml) was added to a stirring solution of (2S)-4-(3-pyridyl)-1-[(4-phenyl)phenoxy]-butan-2-ol (0.25 g), triphenylphosphine (0.262 g) and benzoic acid (0.122 g) in tetrahydrofuran (10 ml) at 0° C. and the resulting solution was stirred for 1 hour. The mixture was concentrated under reduced pressure and the residue was redissolved in methanol (20 ml) and water (5 ml). Solid potassium hydroxide (0.112 g) was added and the reaction stirred for 2 hours before being poured into a solution of saturated aqueous sodium hydrogencarbonate. The mixture was extracted with ethyl acetate and the combined organic extracts were dried over anhydrous magnesium sulfate, filtered and concentrated under reduced pressure to give the title compound (0.22 g) as a solid that was recrystallised from ethyl acetate:hexane.

m.p. 104–106° C.

MS (APCI) 320 (M+H)+

$^1$H NMR (CDCl$_3$) 8.53(1 H, d); 8.4(1 H, d); 7.58-7.50(5 H, m); 7.43(2 H, t); 7.32(1 H, t); 7.24(1 H, dd); 6.96(2 H, d);

4.13-4.02(1 H, m); 4.05(1 H, dd); 3.91(1 H, dd); 2.96-2.89(1 H, m); 2.84-2.76(1 H, m); 2.52-2.42(1 H, bm) 1.99-1.86(2 H, m).

EXAMPLE 28

(±)-α-(2-(4-(Cyclohexyl)phenoxy)methyl)-3-pyridinepropanol

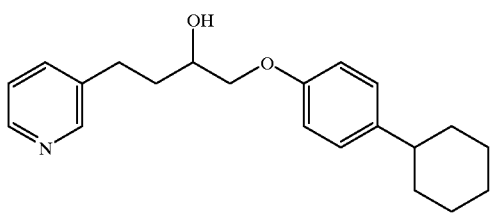

Prepared according to the method described in Example 24b) from 4-cyclohexylphenol (1.76 g), (±)-α-(chloromethyl)-3-pyridinepropanol (0.93 g; from Example 24a) above) and sodium hydroxide (0.40 g) in ethanol (20 ml) and water (5 ml) with heating at reflux for 2 hours to give the title compound as a solid (0.80 g).
m.p. 60–61° C.

MS (EI) 325 (M)$^+$ $^1$H NMR (CDCl$_3$) 8.50(1 H, s); 8.46(1 H, d); 7.55(1 H, d); 7.24-7.20(1 H, m); 7.13-7.11(2 H, d); 6.83(2 H, d); 3.97-3.94(2 H, m); 3.83(1 H, t); 2.90-2.86(1 H, m); 2.81-2.73(1 H, m); 2.50-2.40(2 H, m); 1.92-1.63(7 H, m); 1.39-1.24(5 H, m).

EXAMPLE 29

(±)-α-(6-(Benzyloxy)-2-naphthyloxymethyl)-3-pyridinepropanol

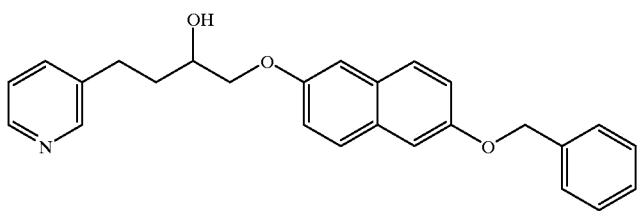

Prepared according to the method described in Example 24b) from 6-(benzyloxy)-2-naphthol (2.2 g; Chem. Ber., (1965) 98, 1233), (±)-α-(chloromethyl)-3-pyridinepropanol (1.89 g; from Example 24a) above) and sodium hydroxide (0.8 g) in ethanol (30 ml) and water (10 ml) with heating at reflux for 6 hours to give the title compound as a solid (0.9 g).

m.p. 101–103° C.

MS (FAB) 400 (M+H)$^+$ $^1$H NMR (CDCl$_3$) 8.53(1 H, s); 8.47(1 H, d); 7.63(2 H, d); 7.58(1 H, d); 7.48(2 H, d); 7.38-7.26(3 H, m); 7.26-7.15(3 H, m); 7.15-7.09(2 H, m); 5.16(2 H, s); 4.09-4.07(2 H, m); 3.96(1 H, dd); 2.94-2.77(2 H, m); 2.45(1 H, s); 1.98-1.92(2 H, m)

EXAMPLE 30

α-(6-Hydroxy-2-naphthyloxymethyl)-3-pyridinepropanol

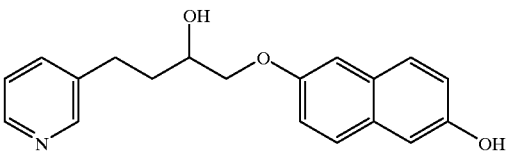

Solid α-(6-(benzyloxy)-2-naphthyloxymethyl)-3-pyridinepropanol (0.90 g; from Example 29 above) was dissolved in dry ethanol (20 ml) and hydrogenated for 2 hours at 5 atmospheres pressure using palladium on carbon (10%, 1 spatula end) as catalyst. The reaction was filtered through Celite and the residue washed with ethanol. The combined filtrate and washings were concentrated under reduced pressure and the residue obtained purified by column chromatography over silica eluting with dichloromethane:methanol (95:5) to give a white solid (0.55 g).

m.p. 165–166° C.

MS (EI) 309 (M)$^+$ $^1$H NMR (DMSO-d$_6$) 9.43(1 H, s); 8.48(1 H, br); 8.41(1 H, br); 7.66(1 H, d); 7.63(1 H, d); 7.58(1 H, d); 7.32(1 H, t); 7.18(1 H, s); 7.08-7.01(3 H, m); 5.07(1 H, d); 3.94(2 H, d); 3.82(1 H, m); 2.86-2.66(2 H, m); 1.89-1.86(1 H, m); 1.76-1.73(1 H, m).

EXAMPLE 31 trans-1-{6-(Methoxymethoxy)-2-naphthyl}-5-(3-pyridyl)-1-penten-3-ol

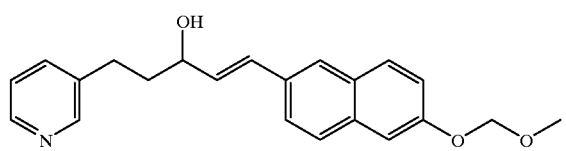

a) 2-Bromo-6-(2-methoxymethoxy)naphthalene

Chloromethyl methyl ether (4.3 ml) was added to a solution of 6-bromo-2-naphthol (5.57 g) and N,N-diisopropylethylamine (13 ml) in dry dichloromethane (100 ml) at 25° C. and the resulting solution stirred for 2 hours. The mixture was washed with hydrochloric acid (0.5 M), dried over anhydrous magnesium sulfate and concentrated

37 under reduced pressure. The residue was purified by column chromatography over silica eluting with hexane:ether (9:1) to give a pink solid (6.07 g).

m.p. 118–120° C.

MS (EI) 266/268 (M)+

$^1$H NMR (CDCl$_3$) 7.92(1 H, s); 7.66(1 H, d); 7.61(1 H, d); 7.51(1 H, d), 7.26(1 H, s); 7.22(1 H, s); 5.29(2 H, s); 3.52(3 H, s).

b) trans-1-{6-(Methoxymethoxy)-2-naphthyl}-5-(3-pyridyl)-1-penten-3-ol

Prepared according to the method described in Example 7b) from 2-bromo-6-(2-methoxymethoxy)naphthalene (2.67 g), palladium(II) acetate (0.224 g), tri-o-tolylphosphine (0.608 g), 5-(3-pyridyl)-1-penten-3-ol (1.63 g) in acetonitrile (20 ml) and triethylamine (4 ml) at 80° C. for 5 hours. The residue obtained after usual work-up was purified by column chromatography over silica eluting with dichloromethane:methanol (95:5) to give 1-{6-(methoxymethoxy)-2-naphthyl}-5-(3-pyridyl)-3-pentanone (see Example 32) and the title compound as an oil (0.51 g).

MS (EI) 349 (M)+

$^1$H NMR (CDCl$_3$) 8.50(1 H, s); 8.44(1 H, d); 7.73-7.66(3 H, m); 7.55(2 H, d); 7.36(1 H, s); 7.20(2 H, t); 6.70(1 H, d); 6.31(1 H, dd); 5.29(2 H, s); 4.32(1 H, q); 3.52(3 H, s); 2.86-2.63(2 H, m); 2.16(1 H, br); 2.11-1.90(2 H, m).

EXAMPLE 32

1-{6-(Methoxymethoxy)-2-naphthyl}-5-(3-pyridyl)-3-pentanol

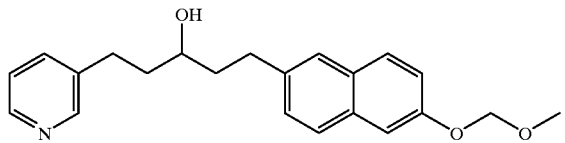

1-{6-(Methoxymethoxy)-2-naphthyl}-5-(3-pyridyl)-3-pentanone (1.9 g; from Example 31 above) was immediately dissolved in methanol (100 ml) and cooled to 0° C. Solid sodium borohydride (0.284 g) was added and the reaction mixture stirred at 25° C. for 2 hours. The mixture was concentrated under reduced pressure and water was added to the residue. The aqueous mixture was extracted with ethyl acetate. The combined extracts were dried over anhydrous magnesium sulfate, filtered and concentrated under reduced pressure. The residue was purified by column chromatography over silica eluting with dichloromethane:methanol (95:5) to give an oil (0.94 g).

MS (FAB) 352 (M+H)+

$^1$H NMR (CDCl$_3$) 8.46(1 H, s); 8.43(1 H, d); 7.69(2 H, t); 7.55(1 H, s); 7.47(1 H, d); 7.36(1 H, s); 7.30(1 H, d); 7.16(2 H, t); 5.29(2 H, s); 3.70-3.66(1 H, m); 3.52(3 H, s); 2.96-2.63(4 H, m); 1.92-1.77(4 H, m), 1.62(1 H, br).

38

EXAMPLE 33

(±)-1-(3'-Chlorobiphenyl-4-yloxy)-4-(3-pyridyl)-2-butanol

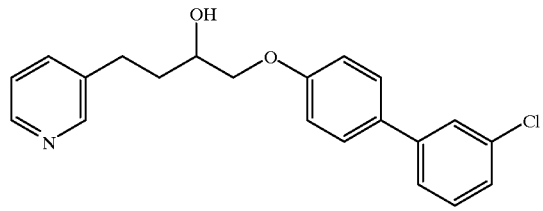

a) 3'-Chloro-4-methoxybiphenyl

A mixture of toluene (18 ml), aqueous sodium carbonate (2 M, 8.6 ml), 4-methoxybenzeneboronic acid (1.43 g), ethanol (4 ml), 1-chloro-3-iodobenzene (1.1 ml) and tetrakis (triphenylphosphine)palladium(0) (0.30 g) was heated at 120° C. for 4 hours. After cooling the reaction mixture was partitioned between water and ether (×3). The combined extracts were dried over anhydrous magnesium sulfate, filtered and concentrated under reduced pressure. The residue was purified by column chromatography over silica eluting with dichloromethane to give the sub-title compound as an oil (2.02 g).

MS (EI) 218/220 (M+H)+

$^1$H NMR (CDCl$_3$) 7.55-7.45(3 H, m); 7.45-7.4(1 H, m); 7.35-7.25(3 H, m); 6.97(1 H, d); 3.85(3 H, s).

b) 3'-Chlorobiphenyl-4-ol

A mixture of 3'-chloro-4-methoxybiphenyl (2.00 g), acetic acid (25 ml) and concentrated hydrobromic acid (25 ml) was heated at reflux for 6 hours. After cooling the reaction was added to water (200 ml) and the solution extracted with ether (300 ml). The ethereal solution was washed with saturated aqueous sodium hydrogencarbonate solution (2×150 ml), dried over anhydrous magnesium sulfate, filtered and concentrated under reduced pressure. The residue was purified by column chromatography over silica eluting with dichloromethane:hexane (1:1) then dichloromethane to give the sub-title compound as a white solid (1.44 g).

m.p. 98–101° C.

MS (EI) 204/206 (M)+

$^1$H NMR (CDCl$_3$) 7.52(1 H, d); 7.45(2 H, d); 7.40(1 H, d); 7.33(1 H, t); 7.28(1 H, d); 6.90(2 H, dd); 4.83(1 H, s).

c) (±)-1-(3'-Chlorobiphenyl-4-yloxy)-4-(3-pyridyl)-2-butanol

Prepared according to the method described in Example 24b) from (±)-α-(chloromethyl)-3-pyridinepropanol (1.0 g), 3'-chlorobiphenyl-4-ol (1.4 g), ethanol (30 ml) and aqueous sodium hydroxide (1.5 M, 5 ml) to give the title compound after purification as a white solid (0.34 g).

m.p. 62–64° C.

MS (APCI) 354/356 (M+H)+

$^1$H NMR (CDCl$_3$) 8.52(1 H, d); 8.46(1 H, dd); 7.6-7.2(8 H, m); 6.96(2 H, dd); 4.1-4.0(2 H, m), 3.95-3.85(1 H, m); 3.0-3.85(1 H, m); 3.85-3.75(1 H, m); 2.46(1 H, d); 2.0-1.9(2 H, m).

EXAMPLE 34

(2R)-1-(3'-Chlorobiphenyl-4-yloxy)-4-(3-pyridyl)-2-butanol oxalic acid salt

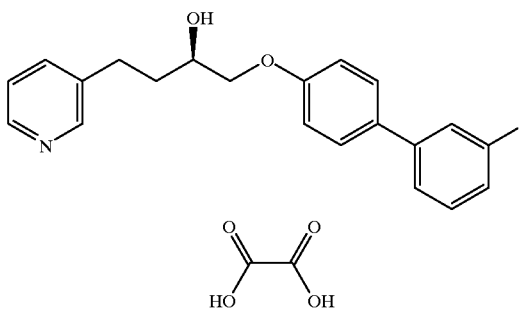

a) (2R,3E/Z)-4-(3-Pyridyl)-1,2-O-isopropylidenebut-3-ene-1,2-diol

Prepared according to the method described in Example 26a) from 3-pyridylmethyltriphenylphosphonium chloride hydrochloride (53.9 g), 2,3-O-(S)-isopropylidene-L-glyceraldehyde (15.2 g) [ex Oxford Asymmetry] and n-butyllithium (2.5 M in hexanes, 100.8 ml) in tetrahydrofuran (550 ml) to give the sub-title compound (21.2 g).

MS (EI) 205 (M)+

$^1$H NMR (CDCl$_3$) major Z-diastereomer 8.53(2 H, d); 7.61(1 H, dt); 7.29(1 H, dd); 6.67(1 H, d); 5.85(1 H, dd); 4.83(1 H, q); 4.16(1 H, t); 3.71(1 H, t); 1.49(3 H, s); 1.39(3 H, s).

b) (2R)-4-(3-Pyridyl)-1,2-O-isopropylidenebutane-1,2-diol

Prepared according to the method described in Example 26b) from (2R,3E/Z)-4-(3-pyridyl)-1,2-O-isopropylidenebut-3-ene-1,2-diol (21.2 g) and palladium on carbon (10%, 0.5 g) in ethyl acetate (200 ml) to give the sub-title compound as an oil (20.5 g).

MS (APCI) 208 (M+H)+

$^1$H NMR (CDCl$_3$) 8.48-8.45(2 H, m); 7.52(1 H, dt); 7.23(1 H, dd); 4.10(1 H, quintet); 4.04(1 H, t); 3.55(1 H, t); 2.84-2.64(2 H, m); 1.94-1.80(2 H, m); 1.44(3 H, s); 1.36(3 H, s).

c) (2R)-4-(3-Pyridyl)-1,2-butanediol

Prepared according to the method described in Example 26c) from (2R)-4-(3-pyridyl)-1,2-O-isopropylidenebutane-1,2-diol (20.5 g) in 2 M hydrochloric acid (100 ml) to give the sub-title compound as an oil (16.4 g).

MS (APCI) 168 (M+H)+

$^1$H NMR (CDCl$_3$) 8.44-8.40(2 H, m); 7.54(1 H, d); 7.22(1 H, dd); 3.73-3.67(1 H, m); 3.65(1 H, dd); 3.48(1 H, dd); 2.90-2.70(2 H, br); 2.87-2.68(2 H, m); 1.84-1.67(2 H, m).

d) (2R)-2-(tert-Butyldimethylsilyloxy)-4-(3-pyridyl)-1-butyl para-toluenesulfonate Prepared according to the method described in Example 26d) from (2R)-4-(3-pyridyl)-1,2-butanediol (5 g) and para-toluenesulfonyl chloride (8.60 g) in pyridine (30 ml) and dichloromethane (30 ml). The resulting adduct was treated with imidazole (3.4 g) and tert-butyldimethylsilyl chloride (5.25 g) in dimethylformamide (20 ml) to give the sub-title compound as an oil (8.7 g).

MS (APCI) 436 (M+H)+

$^1$H NMR (CDCl$_3$) 8.40(1 H, d); 8.35(1 H, s); 7.73(2 H, d); 7.40(1 H, d); 7.29(2 H, d); 7.16(1 H, dd); 3.90-3.83(1 H, m); 3.86(2 H, s); 2.64-2.48(2 H, m); 2.40(3 H, s); 1.82-1.65(2 H, m); 0.82(9 H, s); 0.01(3 H, s); −0.19(3 H, s).

e) (2R)-1-(3'-Chlorobiphenyl-4-yloxy)-4-(3-pyridyl)-2-butanol oxalic acid salt

Prepared according to the method described in Example 26e) from (2R)-2-(tert-butyldimethylsilyloxy)-4-(3-pyridyl)-1-butyl para-toluenesulfonate (2.175 g), sodium hydride (60%, 0.24 g) and 3'-chlorobiphenyl-4-ol (1.22 g) in dimethylformamide (20 ml). The adduct was dissolved in acetonitrile (20 ml) and hydrofluoric acid (40%, 5 ml) was added. The crude product was purified by column chromatography over silica eluting with ethyl acetate. Conversion to the oxalate salt upon treatment with excess ethereal oxalic acid followed by recrystallisation from acetonitrile gave the title compound as a solid (0.92 g).

m.p. 136–139° C.

MS (APCI) 354/356 ((M−oxalic acid)+H)+

$^1$H NMR (DMSO-d$_6$) 8.48(1 H, d); 8.43(1 H, d); 7.71-7.57(6 H); 7.45(1 H, t); 7.43-7.33(1 H, m); 7.04(2 H, d); 3.93(2 H, d); 3.82-3.77(1 H, m); 2.82-2.78(1 H, m); 2.75-2.69(1 H, m); 1.87-1.84(1 H, m); 1.76-1.71(1 H, m).

EXAMPLE 35

(2S)-1-(3'-Chlorobiphenyl-4-yloxy)-4-(3-pyridyl)-2-butanol oxalic acid salt

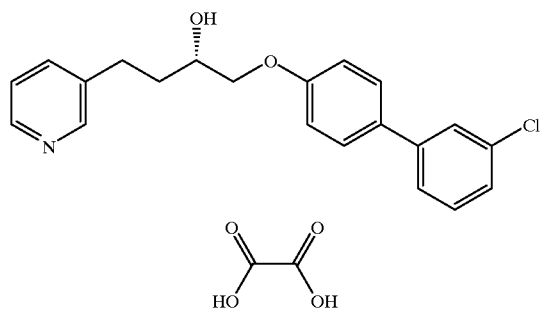

Prepared according to the method described in Example 26e) from (2S)-2-(tert-butyldimethylsilyloxy)-4-(3-pyridyl)-1-butyl para-toluenesulfonate (0.435 g, Example 26d)), sodium hydride (60%, 0.048 g) and 4-(3-chlorophenyl)phenol (0.204 g) in dimethylformamide (5 ml). The adduct was dissolved in acetonitrile (10 ml) and hydrofluoric acid (40%, 2 ml) was added. The crude product was purified by column chromatography over silica eluting with ethyl acetate. Conversion to the oxalate salt upon treatment with excess saturated ethereal oxalic acid followed by recrystallisation from propan-2-ol/ether gave the title compound as a solid (0.22 g).

m.p. 135–138° C.

MS (APCI) 354/356 ((M−oxalic acid)+H)+

$^1$H NMR (DMSO-d$_6$) 8.48(1 H, d); 8.43(1 H, d); 7.71-7.57(6 H); 7.45(1 H, t); 7.43-7.33(1 H, m); 7.04(2 H, d); 3.93(2 H, d); 3.82-3.77(1 H, m); 2.82-2.78(1 H, m); 2.75-2.69(1 H, m); 1.87-1.84(1 H, m); 1.76-1.71(1 H, m).

EXAMPLE 36

(±)-1-(3'-Cyanobiphenyl-4-yloxy)-4-(3-pyridyl)-2-butanol oxalic acid salt

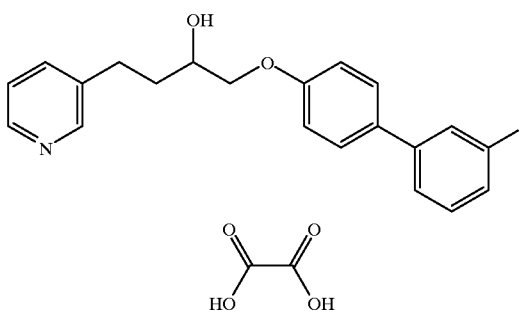

a) 3'-Cyano-4-methoxybiphenyl

Prepared according to the method described in Example 33a) from toluene (75 ml), aqueous sodium carbonate (2 M, 38 ml), 4-methoxybenzeneboronic acid (5.41 g), ethanol (16 ml), 3-bromobenzonitrile (6.41 g) and tetrakis(triphenylphosphine)palladium(0) (0.91 g) with heating at 120° C. for 4 hours. After work up the residue was purified by column chromatography over silica eluting with ethyl acetate:hexane 1:9 to give the sub-title compound as an oil (7.16 g).

GCMS (EI) 209 (M)+

$^1$H NMR (CDCl$_3$) 7.82(1 H, s); 7.76(1 H, dt); 7.57(1 H, dt); 7.55-7.45(1 H, m); 7.50(2 H, d); 7.00(2 H, dt); 3.87(3 H, s).

b) 3'-Cyanobiphenyl-4-ol

A solution of boron tribromide (1.0 M in dichloromethane, 38 ml) was added to a solution of 3'-cyano-4-methoxybiphenyl (4.0 g) in dichloromethane (150 ml) at −78 ° C. After the addition was complete the solution was allowed to warm to room temperature and was stirred for 18 hours. The solution was cooled to 0° C. and then ice (100 g) was added. The organic layer was separated and the aqueous phase extracted with ethyl acetate (3×100 ml). The combined extracts were dried over anhydrous magnesium sulfate, filtered and concentrated under reduced pressure to give the sub-title compound as a cream solid (3.18 g).

m.p. 169–170° C.

GCMS (EI) 195 (M)+

H NMR (CDCl$_3$) 7.81(1 H, s); 7.76(1 H, dt); 7.62-7.42(4 H, m); 6.94(2 H, dt); 5.13(1 H, bs)

c) (±)-1-(3'-Cyanobiphenyl-4-yloxy)-4(3-pyridyl)-2-butanol

A solution of 3'-cyanobiphenyl-4-ol (2.32 g) in ethanol (40 ml) at room temperature was treated with a solution of sodium hydroxide (0.476 g) in water (10 ml) and was then stirred at room temperature for 30 minutes. A solution of (±)-α-(chloromethyl)-3-pyridinepropanol (2.0 g) in ethanol (40 ml) was added to the latter and the resulting mixture heated at reflux for 3 hours. The reaction mixture was cooled and then concentrated under reduced pressure. The residue was purified by column chromatography over silica eluting with ethyl acetate to give a colourless oil (0.90 g). Conversion to the oxalate salt upon treatment with excess saturated ethereal oxalic acid gave the title compound as a white solid (0.40 g).

m.p. 165–166° C.

MS (APCI) 345 ((M−oxalic acid)+H)+

$^1$H NMR (DMSO-d$_6$) 8.50(1 H, d); 8.45-8.40(1 H, m); 8.10(1 H, s); 8.00-7.95(1 H, m); 7.80-7.60(5 H, m); 7.40-7.35(1 H, m); 7.05(2 H, d); 3.9-3.90(2 H, d); 3.80-3.75(1 H, m); 2.8-2.65(2 H, m); 1.90-1.60(2 H, m).

EXAMPLE 37

(2R)-1-(3'-Cyanobiphenyl-4-yloxy)-4-(3-pyridyl)-2-butanol

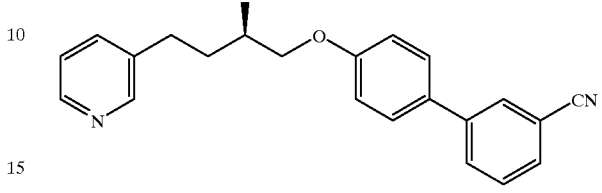

a) (2S)-2-Hydroxy-4-(3-pyridyl)-1-butyl para-toluenesulfonate para-Toluenesulfonyl chloride (2.88 g) was added to a solution of (2S)-4-(3-pyridyl)-1,2-butanediol (1.67 g, Example 26c)) in pyridine (20 ml) and dichloromethane (10 ml). The resulting mixture was stirred at 0° C. for 6 hours. The mixture was concentrated and the residue partitioned between ethyl acetate and saturated aqueous sodium hydrogencarbonate solution. The mixture was extracted with ethyl acetate and the combined organic extract dried over anhydrous magnesium sulfate, filtered and concentrated under reduced pressure. The residue obtained was purified by column chromatography over silica eluting with ethyl acetate to give the sub-title compound as an oil (1.52 g).

MS (APCI) 322 (M+H)+

$^1$H NMR (CDCl$_3$) 8.45(1 H, d); 8.43(1 H, d); 7.77(2 H, d); 7.48(1 H, dt); 7.35(2 H, d); 7.24-7.19(1 H, m); 4.02(1 H, dd); 3.95(1 H, dd); 3.8-3.80(1 H, m); 3.00(1 H, br); 2.80-2.68(2 H, m); 2.45(3 H, s); 1.78-1.68(2 H, m).

b) (2R)-2-Benzoyloxy-4-(3-pyridyl)-1-butyl para-toluenesulfonate

Diethyl azodicarboxylate (0.61 ml) was added to a solution of (2S)-2-hydroxy-4-(3-pyridyl)-1-butyl para-toluenesulfonate (1.4 g), triphenylphosphine (1.31 g) and benzoic acid (0.61 g) in tetrahydrofuran (30 ml) at 0° C. and the resulting solution stirred for 1 hour. The mixture was concentrated under reduced pressure and the residue obtained purified by column chromatography over silica eluting with diethyl ether to give the sub-title compound as a white solid (1.2 g).

m.p. 77–78° C.

MS (APCI) 426 (M+H)+

$^1$H NMR (CDCl$_3$) 8.44(1 H, d); 8.41(1 H, d); 7.93(2 H, d); 7.73(2 H, d); 7.57(1 H, t); 7.49-7.42(3 H, m); 7.23-7.18(3 H, m); 5.25-5.21(1 H, m); 4.29-4.18(2 H, m); 2.73-2.66(2 H, m); 2.36(3 H, s); 2.20-2.00(2 H, m).

c) (2R)-4-(3-Pyridyl)-2-benzoyloxy-1-(3'-cyanobiphenyl-4-yloxy)butane

Solid 3'-cyanobiphenyl-4-ol (0.20 g, Example 36b)) was added to a suspension of sodium hydride (60%, 0.049 g) in dimethylformamide (5 ml) and the resulting solution stirred for 30 minutes. Solid (2R)-2-benzoyloxy-4-(3-pyridyl)-1-butyl para-toluenesulfonate (0.43 g) was then added and the mixture stirred at 60° C. for 2 hours. The mixture was cooled, poured into water (50 ml) and extracted with ethyl acetate. The combined organic extracts were dried over anhydrous magnesium sulfate, filtered and concentrated under reduced pressure. The residue obtained was purified by column chromatography over silica eluting with diethyl ether to give the sub-title compound as an oil (0.34 g).

MS (APCI) 449 (M+H)+

¹H NMR (CDCl₃) 8.50(1 H, d); 8.45(1 H, d); 8.07-8.02(3 H, m); 7.80(1 H, t); 7.76(1 H, dt); 7.60-7.43(7 H, m); 7.26-7.19(1 H, m); 7.01(2 H, d); 5.53-5.48(1 H, m); 4.25-4.18(2 H, m); 2.84-2.78(2 H, m); 2.29-2.24(2 H, m).

d) (2R)-1-(3'-Cyanobiphenyl-4-yloxy)-4-(3-pyridyl)-2-butanol

Potassium carbonate (0.21 g) was added to a solution of (2R)-4-(3-pyridyl)-2-benzoyloxy-1-(3'-cyanobiphenyl-4-yloxy)butane (0.34 g) in methanol (15 ml) and water (5 ml) and the reaction stirred for 2 hours. The mixture was then poured into saturated aqueous sodium hydrogencarbonate solution and the mixture extracted with ethyl acetate. The combined organic extracts were dried over anhydrous magnesium sulfate, filtered and concentrated under reduced pressure. The residue obtained was purified by column chromatography over silica eluting with ethyl acetate to give the title compound as an oil (0.21 g).

MS (APCI) 345 (M+H)+

¹H NMR (CDCl₃) 8.52(1 H, d); 8.47(1 H, dd); 7.82(1 H, dd); 7.76(1 H, dt); 7.61-7.50(5 H, m); 7.26-7.22(1 H, m); 7.01(2 H, d); 4.05-3.92(3 H, m); 2.94-2.80(2 H, m); 2.39(1 H, d); 1.98-1.87(2 H, m).

EXAMPLE 38

(2S)-1-(3'-Cyanobiphenyl-4-yloxy)-4-(3-pyridyl)-2-butanol

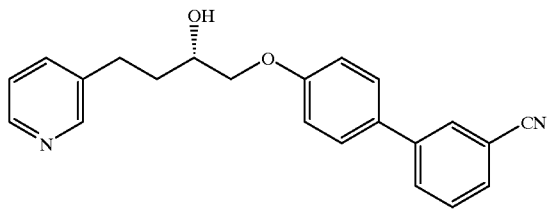

Prepared according to the method described in Example 26e) from (2S)-2-(tert-butyldimethylsilyloxy)-4-(3-pyridyl)-1-butyl para-toluenesulfonate (0.46 g, Example 26d)), sodium hydride (60%, 0.056 g) and 4-(3-cyanophenyl)phenol (0.273 g) in dimethylformamide (5 ml). The adduct was dissolved in tetrahydrofuran (10 ml) and tetrabutylammonium fluoride (0.522 g) was added. The reaction was stirred at ambient temperature for 1 hour and was then poured into brine and extracted with ethyl acetate. The combined organic extracts were dried over anhydrous magnesium sulfate, filtered, concentrated under reduced pressure. The residue obtained was purified by column chromatography over silica eluting with ethyl acetate to give the title compound as a solid (0.22 g).

m.p. 74–75° C.

MS (APCI) 345 (M+H)+

¹H NMR (CDCl₃) 8.52(1 H, d); 8.47(1 H, dd); 7.82(1 H, dd); 7.76(1 H, dt); 7.61-7.50(5 H, m); 7.26-7.22(1 H, m); 7.01(2 H, d); 4.0-3.92(3 H, m); 2.94-2.80(2 H, m); 2.68(1 H, bs); 1.98-1.87(2 H, m).

EXAMPLE 39

(±)-1-(3'-Nitrobiphenyl-4-yloxy)-4-(3-pyridyl)-2-butanol

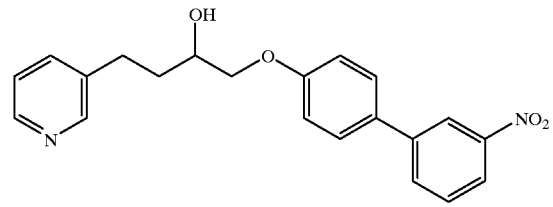

a) 4-Methoxy-3'-nitrobiphenyl

A mixture of toluene (40 ml), aqueous sodium carbonate (2 M, 18 ml), 4-methoxybenzeneboronic acid (2.79 g), ethanol (8 ml), 1-bromo-3-nitrobenzene (3.50 g) and tetrakis(triphenylphosphine)palladium(0) (0.50 g) was heated at 120° C. for 6 hours. After cooling the reaction mixture was partitioned between water and ether. The combined organic extracts were dried over anhydrous magnesium sulfate, the solution filtered and concentrated under reduced pressure. The residue was purified by column chromatography over silica eluting with hexane:toluene (1:1) to give the sub-title compound as a yellow solid (3.62 g).

m.p. 81–83° C.

MS (EI) 229 (M)+

¹H NMR (CDCl₃) 8.41(1 H, s); 8.14(1 H, dd); 7.86(1 H, d); 7.6-7.55(3 H, m); 7.02(2 H, d); 3.88(3 H, s).

b) 3'-Nitrobiphenyl-4-ol

Solid 4-methoxy-3'-nitrobiphenyl (1.63 g) was dissolved in acetic acid (25 ml) and then concentrated hydrobromic acid (48%, 25 ml) was added (CAUTION). The mixture was heated at reflux for 2 hours and was then cooled. The reaction mixture was partitioned between ether and water. The organic layer was dried over anhydrous magnesium sulfate, the solution filtered and concentrated under reduced pressure. The residue was purified by column chromatography over silica eluting with hexane:ether (9:1) to give the sub-title compound as a yellow oil (1.44 g).

MS (EI) 215 (M)+

¹H NMR (CDCl₃) 8.40(1 H, s); 8.15(1 H, dd); 7.86(1 H, d); 7.65-7.5(3 H, m); 6.95(2 H, d); 5.12(1 H, bs).

c) (±)-1-(3'-Nitrobiphenyl-4-yloxy)-4-(3-pyridyl)-2-butanol

A solution of (±)-α-(chloromethyl)-3-pyridinepropanol (0.80 g) in ethanol (10 ml) was added to a refluxing solution of 3'-nitrobiphenyl-4-ol (1.40 g) in ethanol (20 ml) and aqueous sodium hydroxide (1.4 M, 5 ml) over 30 minutes. The solution was heated at reflux for a further hour and then was cooled to room temperature. The reaction mixture was concentrated under reduced pressure and the residue purified by column chromatography over silica eluting with chloroform:ethanol (49:1 to 24:1) to give a yellow solid after trituration with ether (0.332 g).

m.p. 112–114° C.

MS (FAB) 365 (M+H)+

¹H NMR (DMSO-d₆) 8.47(1 H, s); 8.45-8.35(2 H, m); 8.17-8.10(2 H, m); 7.74-7.65(4 H, m); 7.32(1 H, dd); 7.08(2 H, d); 5.11(1 H, d); 3.96(2 H, d); 3.85-3.75(1 H, m); 2.82-2.75(1 H, m); 2.75-2.65(1 H, m); 1.9-1.8(1 H, m); 1.8-1.7(1 H, m).

EXAMPLE 40

(2R)-1-(3'-Nitrobiphenyl-4-yloxy)-4-(3-pyridyl)-2-butanol oxalic acid salt

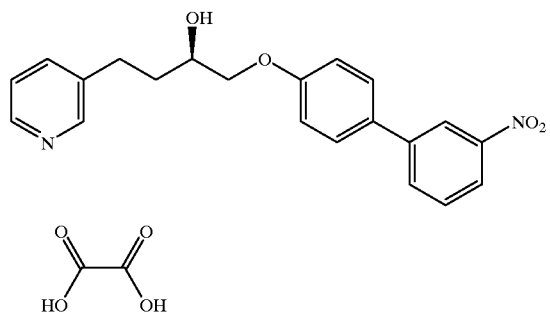

a) (2R)-1-(4-Bromophenoxy)-4-(3-pyridyl)-2-butanol

Prepared according to the method described in Example 26e) from (2R)-2-(tert-butyldimethylsilyloxy)-4-(3-pyridyl)-1-butyl para-toluenesulfonate (4.35 g), sodium hydride (60%, 0.48 g) and 4-bromophenol (2.08 g) in dimethylformamide (30 ml). The adduct was dissolved in acetonitrile (20 ml) and hydrofluoric acid (40%, 5 ml, CAUTION) was added. The reaction was worked up as in Example 34e) and the residue obtained was purified by column chromatography over silica eluting with acetone-:hexane (1:1) to give the sub-title compound as a solid (2.65 g).

m.p. 65–66° C.

MS (APCI) 323 (M+H)$^+$ $^1$H NMR (CDCl$_3$) 8.53(1 H, d); 8.4(1 H, d); 7.58(1 H, dt); 7.38(2 H, d); 7.24(1 H, dd); 6.80(2 H, d); 4.2-3.94(1 H, m); 3.92(1 H, dd); 3.82(1 H, dd); 2.9-2.84(1 H, m); 2.82-2.72(1 H, m); 2.46(1 H, br); 1.96-1.80(2 H, m).

b) (2R)-1-(3'-Nitrobiphenyl-4-yloxy)-4-(3-pyridyl)-2-butanol oxalic acid salt

Prepared according to the method described in Example 33a) from toluene (5 ml), aqueous sodium carbonate (2 M, 1 ml), (2R)-1-(4-bromophenoxy)-4-(3-pyridyl)-2-butanol (0.31 g) ethanol (1 ml), 3-nitrobenzeneboronic acid (0.24 g) and tetrakis(triphenylphosphine)palladium(0) (30 mg) with heating at 110° C. for 4 hours. The residue obtained after work up was purified by column chromatography over silica eluting with ethyl acetate to give (2R)-1-(3'-nitrobiphenyl-4-yloxy)-4-(3-pyridyl)-2-butanol as a yellow oil (0.210 g). Conversion to the oxalate salt upon treatment with excess saturated ethereal oxalic acid gave the title compound as a hygroscopic gum (0.150 g).

MS (APCI) 365 ((M–oxalic acid)+H)$^+$ $^1$H NMR (DMSO-d$_6$) 8.50(1 H, d); 8.48-8.4(1 H, m); 8.40-8.35(1 H, m); 8.15-8.05(2 H, m); 7.75-7.70(4 H, m); 7.4-7.35(1 H, m); 7.1-7.05(2 H, d); 3.95(2 H, d); 3.80-3.75(1 H, m); 2.80-2.70(2 H, m); 1.90-1.70(2 H, m).

EXAMPLE 41

(2S)-1-(3'-Nitrobiphenyl-4-yloxy)-4-(3-pyridyl)-2-butanol oxalic acid salt

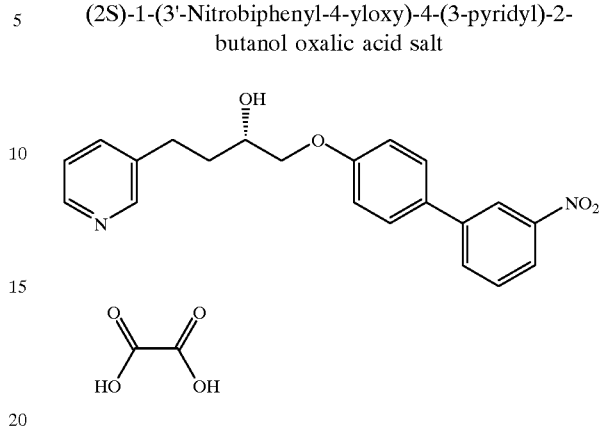

a) (2S)-1-(4-Bromophenoxy)-4-(3-pyridyl)-2-butanol

Prepared according to the method described in Example 26e) from (2S)-2-(tert-butyldimethylsilyloxy)-4-(3-pyridyl)-1-butyl para-toluenesulfonate (4.35 g), sodium hydride (60%, 0.48 g) and 4-bromophenol (2.08 g) in dimethylformamide (30 ml). The adduct was dissolved in acetonitrile (20 ml) and hydrofluoric acid (40%, 5 ml, CAUTION) was added. After work up the residue was purified by column chromatography over silica eluting with ethyl acetate to give the title compound as a colourless solid (1.08 g).

m.p. 63–65° C.

MS (APCI) 322/324 (M+H)$^+$ $^1$H NMR (CDCl$_3$) 8.53(1 H, d); 8.4(1 H, d); 7.58(1 H, dt); 7.38(2 H, d); 7.24(1 H, dd); 6.80(2 H, d); 4.2-3.94(1 H, m); 3.92(1 H, dd); 3.82(1 H, dd); 2.98-2.84(1 H, m); 2.82-2.72(1 H, m); 2.46(1 H, br); 1.96-1.80(2 H, m).

b) (2S)-4-(3-Pyridyl)-1-[4-(3-nitrophenyl)phenoxy]-2-butanol oxalic acid salt

Prepared according to the method described in Example 33a) from (2S)-1-(4-bromophenoxy)-4-(3-pyridyl)-2-butanol (0.25 g), 3-nitrobenzeneboronic acid (0.194 g), sodium carbonate decahydrate (0.444 g) and tetrakis(triphenylphosphine)palladium(0) (0.022 g) in ethanol (1 ml), water (1 ml) and toluene (5 ml). Conversion to the oxalate salt upon treatment with excess saturated ethereal oxalic gave the title compound as a hygroscopic glass (0.21 g).

MS (APCI) 365 ((M–oxalic acid)+H)$^+$ $^1$H NMR (DMSO-d$_6$) 8.50(1 H, d); 8.48-8.4(1 H, m); 8.40-8.35(1 H, m); 8.15-8.05(2 H, m); 7.75-7.70(4 H, m); 7.4-7.35(1 H, m); 7.1-7.05(2 H, d); 3.95(2 H, d); 3.80-3.75(1 H, m); 2.8-2.70(2 H, m); 1.90-1.70(2 H, m).

EXAMPLE 42

(±)-1-(3'-Methoxybiphenyl-4-yloxy)-4-(3-pyridyl)-2-butanol

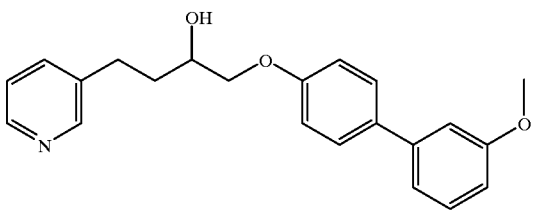

a) 4-Bromophenyl tert-butyl ether

Gaseous isobutylene was passed through a solution of 4-bromophenol (27 g) in dichloromethane (200 ml) containing concentrated sulfuric acid (0.25 ml). When the gas no longer dissolved the mixture was left to stir overnight. A solution of saturated aqueous sodium hydrogen carbonate (100 ml) was added and the layers separated. The organic solution was dried over anhydrous sodium sulfate, filtered and concentrated under reduced pressure. The residue was purified by column chromatography over silica eluting with hexane:ether 19:1 to give the sub-title compound as an oil (23 g).

MS (EI) 228/230 (M)$^+$ $^1$H NMR (CDCl$_3$) 7.36(2 H, dt); 6.86(2 H, dt); 1.33(9 H, s).

b) 4-tert-butoxybenzeneboronic acid

A solution of tert-butyllithium (1.7 M in pentane, 12 ml, CAUTION-PYROPHORIC) was added dropwise to a stirring solution of 4-bromophenyl tert-butyl ether (2.33 g) in tetrahydrofuran (20 ml) at −70° C. After a further 5 minutes the resulting solution of anion was added dropwise to a solution of triisopropyl borate (6 ml) in tetrahydrofuran (10 ml) at −70 ° C. After the addition was complete the reaction mixture was allowed to warm to room temperature. After 20 minutes a solution of saturated aqueous ammonium chloride (25 ml) and ether (25 ml) was added. The layers were separated and the aqueous phase washed with ether (50 ml). The combined organic extracts were washed with dilute hydrochloric acid (5%, 25 ml) and were then dried over anhydrous magnesium sulfate. The solution was filtered and concentrated under reduced pressure to give a white solid. This was purified by column chromatography over silica eluting with ether then methanol to give the sub-title compound as a white solid (0.69 g).

m.p. 204–208° C.

$^1$H NMR (CDCl$_3$) 8.14(2 H, d); 7.10(2 H, d); 1.43(9 H, s).

c) 3'-Methoxybiphenyl-4-ol

A solution of 4-tert-butoxybenzeneboronic acid (0.50 g), 3-bromoanisole (0.44 g), and tetrakis(triphenylphosphine)palladium(0) (0.09 g) in toluene (5 ml), ethanol(1.2 ml) and aqueous sodium carbonate (2 M, 2.4 ml) was heated at 100° C. for 19 hours. After cooling the reaction mixture was added to brine (50 ml) and ethyl acetate (50 ml). The organic layer was separated and dried over anhydrous magnesium sulfate. The solution was then filtered and concentrated under reduced pressure. The residue was purified by column chromatography over silica eluting with hexane:toluene 9:1 to give 4-tert-butoxy-3'-methoxybiphenyl (0.61 g). (MS (EI) 256 (M)$^+$). Trifluoroacetic acid (5 ml) was added to a solution of 4-tert-butoxy-3'-methoxybiphenyl (0.60 g) in dichloromethane (20 ml) and the resulting solution stirred for 1 hour. The solution was then concentrated under reduced pressure. The residue was partitioned between a solution of saturated aqueous sodium hydrogen carbonate (25 ml) and ether (3×25 ml). The combined extracts were dried over anhydrous magnesium sulfate, filtered and concentrated under reduced pressure. The residue was purified by column chromatography over silica eluting with dichloromethane to give the sub-title compound as a solid (0.25 g).

m.p. 93–95° C.

MS (EI) 200 (M)$^+$ $^1$H NMR (CDCl$_3$) 7.47(2 H, dt); 7.33(1 H, t); 7.12(1 H, d); 7.07(1 H, t); 6.92-6.83(3 H, m); 4.97(1 H, bs); 3.86(3 H, s).

d) (±)-1-(3'-Methoxybiphenyl-4-yloxy)-4-(3-pyridyl)-2-butanol

Prepared according to the method described in Example 24b) from (±)-α-(chloromethyl)-3-pyridinepropanol (1.90 g), 3'-methoxybiphenyl-4-ol (2.05 g), ethanol (40 ml) and aqueous sodium hydroxide (2.1 M, 5 ml). After the reaction was complete it was concentrated under reduced pressure and the residue partitioned between ethyl acetate and water. The combined organic extracts were dried over anhydrous magnesium sulfate, filtered and concentrated under reduced pressure. The residue was twice purified by column chromatography over silica eluting with dichloromethane:ethyl acetate as an oil (1.35 g). A white solid was obtained after trituration with ether:hexane.

m.p. 62–64° C.

MS (APCI) 350 (M+H)$^+$ $^1$H NMR (DMSO-d$_6$) 8.46(1 H, d); 8.40(1 H, dd); 7.66(1 H, d); 7.59(2 H, d); 7.32(2 H, q); 7.17(1 H, d); 7.13(1 H, d); 7.00(2 H, d); 6.87(1 H, dd); 5.09(1 H, d); 3.92(2 H, d); 3.85-3.75(1 H, m); 3.81(3 H, s); 2.85-2.75(1 H, m); 2.75-2.6(1 H, m); 1.95-1.8(1 H, m); 1.8-1.65(1 H, m).

EXAMPLE 43

(±)-1-(3'-Fluorobiphenyl-4-yloxy)-4-(3-pyridyl)-2-butanol

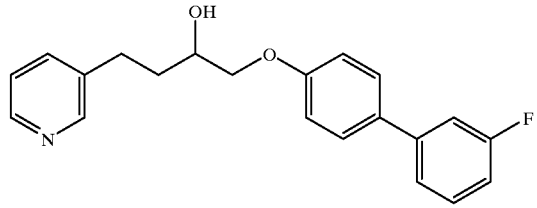

a) (±)-1-(4-Bromophenoxy)-4-(3-pyridyl)-2-butanol

Prepared according to the method described in Example 24b) from (±)-α-(chloromethyl)-3-pyridinepropanol (2.41 g), 4-bromophenol (4.68 g), ethanol (80 ml) and aqueous sodium hydroxide (1.3 M, 20 ml) to give the sub-title compound as an oil (2.25 g).

MS (EI) 322/4 (M)$^+$ $^1$H NMR (CDCl$_3$) 8.50(1 H, d); 8.45(1 H, dd); 7.56(1 H, d); 7.38(2 H, d); 7.24(1 H, dd); 6.77(2 H, d); 4.05-3.9(2 H, m); 3.9-3.8(1 H, m); 3.0-2.85(1 H, m); 2.85-2.7(1 H, m); 2.0-1.8(2 H, m).

b) (±)-1-(4-Bromophenoxy)-4-(3-pyridyl)-2-(tert-butyldimethylsilyloxy)butane

Imidazole (0.73 g) and dimethylaminopyridine (10 mg) was added to a solution of (±)-1-(4-bromophenoxy)-4-(3-pyridyl)-2-butanol (2.20 g) in dimethylformamide (15 ml). When the mixture was homogeneous solid tert-butyldimethylsilyl chloride was added and the solution stirred for 26 hours. A saturated aqueous solution of sodium chloride (200 ml) was added and the mixture extracted with ether (3×100 ml). The combined organic extracts were dried over anhydrous magnesium sulfate, filtered and concentrated under reduced pressure to give the sub-title compound as an oil (2.75 g).

MS (EI) 380 (M−Bu$^t$+H)$^+$ $^1$H NMR (CDCl$_3$) 8.35(1 H, s); 8.32(1 H, d); 7.38(1 H, d); 7.22(2 H, d); 7.08(1 H, dd); 6.65(2 H, d); 4.0-3.95(1 H, m); 3.76-3.65(2 H, m); 2.72-2.62(1 H, m); 2.60-2.50(1 H, m); 1.85-1.65(2 H, m); 0.80(9 H, s); 0.00(3 H, s), −0.03(3 H, s).

c) (±)-1-(3'-Fluorobiphenyl-4-yloxy)-4-(3-pyridyl)-2-(tert-butyldimethylsilyloxy)butane Prepared according to the method described in Example 33a) from toluene (5 ml), aqueous sodium carbonate (2 M, 2.2 ml), (±)-3-(4(4-bromophenoxy)-3-(tert-butyldimethylsilyloxy)butyl)pyridine (0.79 g), ethanol (1.3 ml), 3-fluorobenzeneboronic acid (0.25 g) and tetrakis(triphenylphosphine)palladium(0) (72 mg) with heating at 120° C. for 6 hours. The residue obtained after work up was purified by column chromatography over silica to give the sub-title compound as an oil (0.49 g).

MS (FAB) 452 (M+H)$^+$ $^1$H NMR (CDCl$_3$) 8.4-8.25(2 H, m); 7.45-7.3(3 H, m); 7.3-7.15(1 H, m); 7.15-7.0(3 H, m); 6.9-6.75(3 H, m); 4.05-3.95(1 H, m); 3.9-3.7(2 H, m); 2.75-2.5(2 H, m); 1.9-1.7(2 H, m); 0.81(9 H, s); 0.02(3 H, s); 0.00(3 H, s).

d) (±)-1-(3'-Fluorobiphenyl-4-yloxy)-4-(3-pyridyl)-2-butanol

Hydrofluoric acid (40%, 4 ml) was added to a solution of (±)-3-(4-(3'-fluorobiphenyl-4-yloxy)-3-(tert-butyldimethylsilyloxy)butyl)pyridine in acetonitrile (30 ml) and the mixture stirred for 2 days. The solution was neutralised by careful addition to a saturated aqueous solution of sodium bicarbonate (200 ml). The mixture was extracted with ethyl acetate, the organic extract dried over anhydrous magnesium sulfate, filtered and concentrated under reduced pressure. The residue was purified twice by column chromatography over silica eluting with dichloromethane then ethyl acetate to give the title compound as a white powder (0.33 g).

m.p. 96–98° C.

MS (FAB) 338 (M+H)$^+$ $^1$H NMR (DMSO-d$_6$) 8.47(1 H, s); 8.40(1 H, d); 7.7-7.6(3 H, m); 7.5-7.4(3 H, m); 7.35-7.3(1 H, m); 7.16-7.10(1 H, m); 7.02(2 H, d); 5.09(1 H, d); 3.93(2 H, d); 3.82-3.77(1 H, m); 2.84-2.75(1 H, m); 2.75-2.66(1 H, m); 1.9-1.8(1 H, m); 1.8-1.7(1 H, m).

EXAMPLE 44

(2R)-1-(3'-Fluorobiphenyl-4-yloxy)-4-(3-pyridyl)-2-butanol

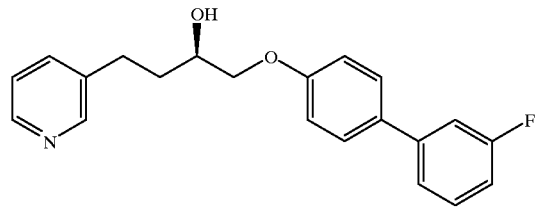

Prepared according to the method described in Example 33a) from toluene (5 ml), ethanol (3 ml), aqueous sodium carbonate (2 M, 1 ml), (2R)-1-(4-bromophenoxy)-4-(3-pyridyl)-2-butanol (0.25 g), ethanol (1 ml), 3-fluorobenzeneboronic acid (0.16 g) and tetrakis(triphenylphosphine)palladium(0) (60 mg) with heating at 110° C. for 4 hours. The residue obtained after work up was purified by column chromatography over silica eluting with ethyl acetate to give the title compound after trituration with diethyl ether:hexane (1:1) as a white solid (0.13 g).

m.p. 61–62° C.

MS (APCI) 338 (M+H)$^+$ $^1$H NMR (CDCl$_3$) 8.50(1 H, s); 8.45(1 H, d); 7.70-7.65(1 H, m); 7.50-7.40(3 H, m); 7.35-7.25(2 H, m); 7.25-7.20(1 H, m); 6.95-6.80(3 H, m); 4.00-3.95(2 H, m); 3.90-3.85(1 H, m); 2.95-2.90(1 H, m); 2.85-2.75(1 H, m); 2.55(1 H, s); 2.00-1.85(2 H, m).

EXAMPLE 45

(±)-4'-(2-Hydroxy-4-(3-pyridyl)butoxy)biphenyl-3-carboxamide

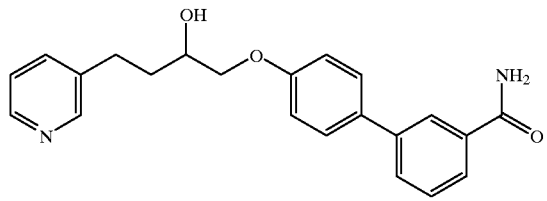

a) (±)-4-[4-(3-pyridyl)-2-(tert-butyldimethylsilyloxy)butoxy]benzeneboronic acid A solution of tert-butyllithium (1.7 M in pentane, 4 ml, CAUTION-PYROPHORIC) was added dropwise to a stirring solution of (±)-1-(4-bromophenoxy)-4-(3-pyridyl)-2-(tert-butyldimethylsilyloxy)butane (1.50 g, Example 43b) in tetrahydrofuran (6 ml) at −70° C. After a further 5 minutes the resulting solution of anion was added dropwise to a solution of triisopropyl borate (1 ml) in tetrahydrofuran (1 ml) at −70° C. After the addition was complete the reaction mixture was allowed to warm to room temperature. After 10 minutes water (25 ml) and ethyl acetate (25 ml) were added. The organic phase was separated, dried over anhydrous magnesium sulfate, filtered and concentrated under reduced pressure to give an oil. This was partly purified by column chromatography over silica eluting with dichloromethane then ethyl acetate then methanol to give the sub-title compound as an oil which was used immediately.

b) (±)-4'-(2-Hydroxy-4-(3-pyridyl)butoxy)biphenyl-3-carboxamide

Prepared according to the method described in Example 33a) from toluene (3 ml), aqueous sodium carbonate (2 M, 1.4 ml), ethanol (0.8 ml), 3-bromobenzamide (0.5 g), (±)-4-[4-(3-pyridyl)-2-(tert-butyldimethylsilyloxy)butoxy]benzeneboronic acid (1.0 g) and tetrakis(triphenylphosphine)palladium(0) (70 mg) with heating at 120° C. for 3 hours. The residue obtained after work up was purified by column chromatography over silica eluting with 5% ethanol in dichloromethane to give a yellow gum which was deprotected as in Example 34e) using hydrofluoric acid (40%, 5 ml, CAUTION) in acetonitrile (20 ml). The residue obtained after work up was triturated with diethyl ether to give the title compound as a pale yellow solid (0.224 g)

m.p. 110–113° C.

MS (EI) 362 (M)$^+$ $^1$H NMR (DMSO-d$_6$) 8.47(1 H, s); 8.40(1 H, d); 8.11(2 H, s); 7.83-7.73(2 H, m); 7.70-7.62(3 H, m); 7.50(1 H, t); 7.42(1 H, s); 7.32(1 H; q); 7.05(2 H, dd); 5.09(1 H, d); 3.94(2 H, d); 3.85-3.75(1 H, m); 2.85-2.64(2 H, m); 1.93-1.68(2 H, m).

EXAMPLE 46

(±)-1-(3',5'-Dichlorobiphenyl-4-yloxy)-4-(3-pyridyl)-2-butanol

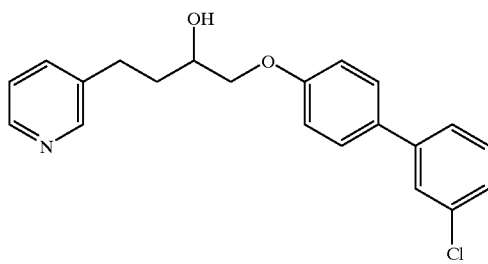

Prepared according to the method described in Example 33a) from toluene (3 ml), aqueous sodium carbonate (2 M, 1.4 ml), (±)-3-(4-(4-bromophenoxy)-3-(tert-butyldimethylsilyloxy)butyl)pyridine (0.67 g), ethanol (0.8 ml), 3,5-dichlorobenzeneboronic acid (0.30 g) and tetrakis(triphenylphosphine)palladium(0) (73 mg) with heating at 120° C. for 6 hours. The residue obtained after work up was deprotected as in Example 34e) using hydrofluoric acid (40%, 4 ml) in acetonitrile (30 ml). The residue obtained after work up was purified by column chromatography over silica eluting with dichloromethane then ether then ethyl acetate to give an oil (0.47 g). This was recrystallised from ether to give the title compound as a white solid (0.21 g).

m.p. 101–102° C.

MS (APCI) 388/390 (M)+

$^1$H NMR (DMSO-d$_6$) 8.46(1 H, s); 8.40(1 H, d); 7.7-7.6(5 H, m); 7.52(1 H, s); 7.31(1 H, dd); 7.03(2 H, d); 5.09(1 H, d); 3.94(2 H, d); 3.85-3.75(1 H, m); 2.85-2.75(1 H, m); 2.75-2.65(1 H, m); 1.9-1.8(1 H, m); 1.8-1.7(1 H, m).

EXAMPLE 47

(±)-N-phenyl-4'-(2-Hydroxy-4-(3-pyridyl)butoxy)biphenyl-3-carboxamide

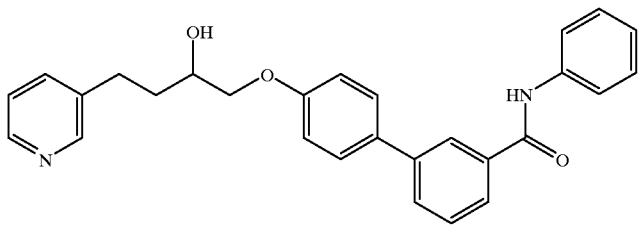

Prepared according to the method described in Example 33a) from toluene (3 ml), aqueous sodium carbonate (2 M, 0.9 ml), ethanol (1.0 ml), 3-bromo-N-phenylbenzamide (0.48 g), (±)-4-[4-(3-pyridyl)-2-(tert-butyldimethylsilyloxy)butoxy]benzeneboronic acid (0.7 g) and tetrakis(triphenylphosphine)palladium(0) (50 mg) with heating at 120° C. for 5 hours. The residue obtained after work up was purified by column chromatography over silica eluting with ethyl acetate:hexane (1:1) to give a colourless oil which was desilylated by treatment with tetrabutylammonium fluoride (0.7 ml; 1 M in tetrahydrofuran) in tetrahydrofuran at 0° C. After stirring at this temperature for 5 minutes a saturated solution of brine (5 ml) was added and the organic phase separated. The aqueous phase was extracted with ethyl acetate (20 ml). The combined organic phases were washed with brine, dried over anhydrous magnesium sulfate, filtered and concentrated under reduced pressure. The residue was purified by column chromatography over silica eluting with ethanol:dichloromethane (1:19) to give the title compound as a colourless solid (0.09 g).

m.p. 90–93° C.

MS (APCI) 439 (M+H)+

$^1$H NMR (DMSO-d$_6$) 10.33(1 H, s); 8.47(1 H, s); 8.40(1 H, d); 8.16(1 H, s); 7.90-7.75(4 H, m); 7.75-7.65(3 H, m); 7.60(1 H, t); 7.40-7.29(3 H, m); 7.15-7.05(3 H, m); 5.10(1 H, d); 3.95(2 H, d); 3.85-3.75(1 H, m); 2.87-2.65(2 H, m); 1.93-1.68(2 H, m).

EXAMPLE 48

(±)-1-(2',4'-Dichlorobiphenyl-4-yloxy)-4-(3-pyridyl)-2-butanol oxalic acid salt

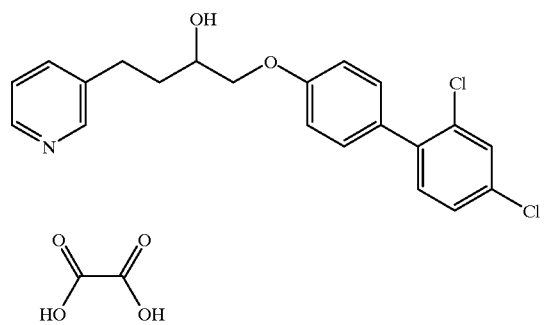

Prepared according to the method described in Example 33a) from toluene (3 ml), aqueous sodium carbonate (2 M, 1.4 ml), (±)-1-(4-bromophenoxy)-4-(3-pyridyl)-2-butanol (0.51 g), ethanol (0.8 ml), 2,4-dichlorobenzeneboronic acid (0.32 g) and tetrakis(triphenylphosphine)palladium(0) (75 mg) with heating at 120° C. for 4 hours. The residue obtained after work up was purified by column chromatography over silica eluting with dichloromethane then ether then ethyl acetate to give (±)-1-(2',4'-dichlorobiphenyl-4-yloxy)-4-(3-pyridyl)-2-butanol (0.48 g). A sample that had been purified by reverse phase HPLC was converted to the oxalate salt by treatment of the parent compound in ether with a saturated ethereal solution of oxalic acid. The precipitated salt was filtered to give the title compound (0.23 g).

m.p. 118–120° C. (dec.)

MS (APCI) 388/390 ((M−oxalic acid)+H)+

$^1$H NMR (DMSO-$_6$) 8.49(1 H, s); 8.42(1 H, d); 7.75-6.95(2 H, m); 7.5-7.3(5 H, m); IS 7.03(2 H, d); 3.94(2 H, d); 3.85-3.75(1 H, m); 2.9-2.65(2 H, m); 1.95-1.65(2 H, m).

EXAMPLE 49

(2R)-1-(4'-Fluorobiphenyl-4-yloxy)-4-(3-pyridyl)-2-butanol

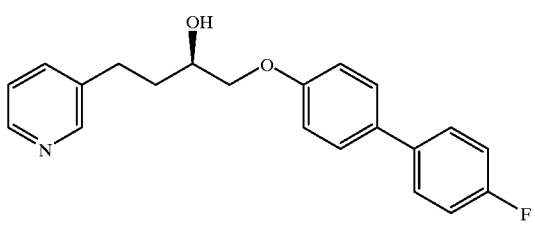

Prepared according to the method described in Example 33a) from toluene (5 ml), aqueous sodium carbonate (2 M, 1 ml), (2R)-1-(4-bromophenoxy)-4-(3-pyridyl)-2-butanol (0.25 g), ethanol (1 ml), 4-fluorobenzeneboronic acid (0.119 g) and tetrakis(triphenylphosphine)palladium(0) (22 mg) with heating at 110° C. for 4 hours. The residue obtained after work up was purified by column chromatography over silica eluting with ethyl acetate to give the title compound as a white solid after recrystallisation from ethyl acetate:hexane (1:1) (0.18 g).

m.p. 124–125° C.

MS (APCI) 338 (M+H)$^+$ $^1$H NMR (CDCl$_3$) 8.55(1 H, d); 8.5-8.45(1 H, dd); 7.6-7.55(1 H, m); 7.50-7.45(4 H, m); 7.25-7.20(1 H, m); 7.15-7.10(2 H, m); 7.0-6.95(2 H, m); 4.05-4.0(2 H, m); 3.95-3.85 (1H, m); 2.95-2.80(2 H, m); 2.45(1 H, d); 1.95-1.85(2 H, m).

EXAMPLE 50

(2R)-1-(3'-Aminobiphenyl-4-yloxy)-4-(3-pyridyl)-2-butanol

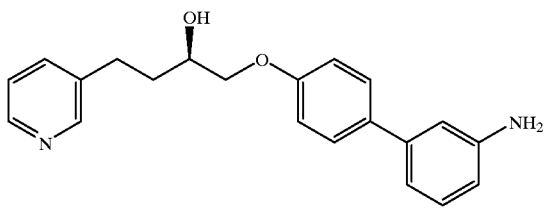

Aqueous sodium carbonate solution (2 M, 1.55 ml) was added to a solution of (2R)-1-(4-bromophenoxy)-4-(3-pyridyl)-2-butanol (0.50 g), 3-aminobenzeneboronic acid monohydrate (0.26 g) and tetrakis(triphenylphosphine) palladium(0) (0.045 g) in ethanol (1.72 ml) and toluene (6.9 ml). The mixture was stirred at reflux under a nitrogen atmosphere for 3 hours and then, cooled to room temperature. The reaction mixture was poured into water and then extracted with ethyl acetate. The combined organic extracts were dried over anhydrous magnesium sulfate, filtered and concentrated under reduced pressure. The residue was purified by column chromatography over silica eluting with dichloromethane:methanol (19:1) to give the title compound (0.43 g) as an which was recrystallised from isohexane:ethyl acetate to give a white solid.

m.p. 103–104° C.

MS (APCI) 335.1 (M+H)$^+$ $^1$H NMR (CDCl$_3$) 8.52(1 H, d); 8.47(1 H, dd); 7.56(1 H, dt), 7.49(2 H, d); 7.27-7.17(2 H, m); 7.0-6.9(1 H, m); 6.94(2 H, d); 6.86(1 H, t), 6.65(1 H, dt); 4.10-3.97(2 H, m); 3.90(1 H, dd); 3.73(2 H, bs); 2.97-2.87(1 H, m); 2.84-2.77(1 H, m); 2.50(1 H, d); 2.0-1.8(2 H, m).

EXAMPLE 51

(2R)-1-(3'-Fluoro-4'-propoxybiphenyl-4-yloxy)-4-(3-pyridyl)-2-butanol

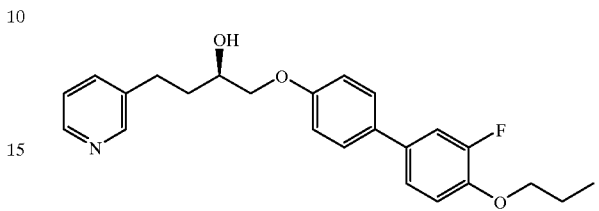

a) 1-Bromo-3-fluoro-4-propoxybenzene

2-Fluoro-4-bromophenol (1.91 g) was added to a suspension of potassium carbonate (1.52 g) in acetone (30 ml) and the mixture stirred at room temperature for 30 minutes. Propyl iodide (1.87 g) was added and the mixture heated at reflux for 16 hours. The mixture was cooled to room temperature and filtered. The solution obtained was concentrated under reduced pressure to give the sub-title compound as a yellow oil (2.3 g).

MS (APCI) 233/235 (M+H)$^+$ $^1$H NMR (CDCl$_3$) 7.22(1 H, dd); 7.19-7.15(1 H, m); 6.83(1 H, t); 3.96(2 H, t); 1.83(2 H, sextet); 1.05(3 H, t).

b) 3-Fluoro-4-propoxybenzeneboronic acid

A solution n-butyllithium (2.5 M in hexanes, 4.4 ml) was added dropwise over 5 minutes to a stirring solution of 1-bromo-3-fluoro-4-propoxybenzene (2.3 g) in tetrahydrofuran (10 ml) at −70° C. The solution was stirred at −70° C. for 15 minutes and then transferred by cannula to a solution of triisopropyl borate (4.14 g) in tetrahydrofuran (10 ml) at −78° C. Once addition was complete the mixture was stirred at room temperature for 30 minutes. A solution of dilute hydrochloric acid (2 M, 30 ml) was added and the mixture extracted with ethyl acetate (3×50 ml). The combined organic extracts were dried over anhydrous magnesium sulfate, filtered and concentrated under reduced pressure to give the sub-title compound as a white solid (1.19 g).

c) (2R)-1-(3'-Fluoro-4'-propoxybiphenyl-4-yloxy)-4-(3-pyridyl)-2-butanol

Prepared according to the method described in Example 33a) from toluene (5 ml), aqueous sodium carbonate (2 M, 1 ml), (2R)-1-(4-bromophenoxy)-4-(3-pyridyl)-2-butanol (0.25 g, Example 40a), ethanol (1 ml), 3-fluoro-4-propoxybenzeneboronic acid (0.23 g) and tetrakis (triphenylphosphine)palladium(0) (22 mg) with heating at reflux for 4 hours. The residue obtained after work-up was purified by column chromatography over silica eluting with ethyl acetate to give the title compound as a white solid (0.19 g)

m.p. 120–121° C.

MS (APCI) 396 (M+H)$^+$ $^1$H NMR (CDCl$_3$) 8.55(1 H, d); 8.45(1 H, d); 7.60-7.55(1 H, m); 7.45-7.40(2 H, m) 7.3-7.20(3 H, m); 7.00-6.90(3 H, m); 4.05-4.00(4 H, m); 3.90-3.85(1 H, m); 3.00-2.80(2 H, m); 2.50(1 H, bs); 2.00-1.85(4 H, m); 1.05(3 H, t).

EXAMPLE 52

(2R)-4-(3-Pyridyl)-1-(3'-trifluoromethylbiphenyl-4-yloxy)-2-butanol oxalic acid salt

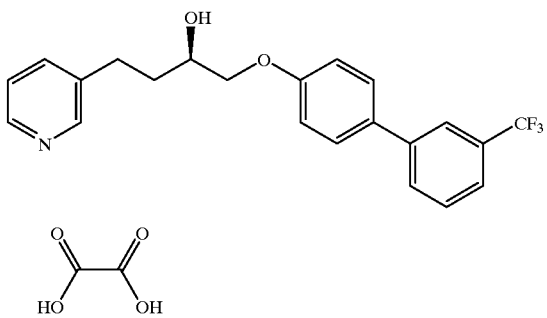

Prepared according to the method described in Example 33a) from toluene (5 ml), aqueous sodium carbonate (2 M, 1 ml), (2R)-1-(4-bromophenoxy)-4-(3-pyridyl)-2-butanol (0.25 g), ethanol (1 ml), 3-trifluoromethylbenzeneboronic acid (0.161 g) and tetrakis(triphenylphosphine)palladium(0) (22 mg) with heating at reflux for 6 hours. The residue obtained after work-up was purified by column chromatography over silica eluting with ethyl acetate to give (2R)-1-(3'-trifluoromethylbiphenyl-4-yloxy)-4-(3-pyridyl)-2-butanol as a colourless oil (0.180 g). Conversion to the oxalate salt upon treatment with excess saturated ethereal oxalic acid gave the title compound as a hygroscopic gum. (0.150 g)

MS (APCI) 388 ((M−oxalic acid)+H)$^+$ $^1$H NMR (DMSO-d$_6$) 8.50(1 H, s); 8.40(1 H, d); 8.0-7.90(2 H, m); 7.70-7.65(5 H, m); 7.40-7.35(1 H, m); 7.05(2 H, d); 3.95(2 H, d); 3.80-3.75(1 H, m); 2.9-2.65(2 H, m); 1.90-1.70(2 H, m).

EXAMPLE 53

(2R)-1-(3'-Acetamidobiphenyl-4-yloxy)-4-(3-pyridyl)-2-butanol

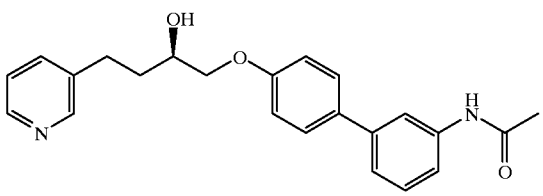

Prepared according to the method described in Example 33a) from (2R)-1-(4-bromophenoxy)-4-(3-pyridyl)-2-butanol (0.50 g), 3-acetamidobenzeneboronic acid (0.38 g) and tetrakis(triphenylphosphine)palladium(0) (0.045 g) in ethanol (1.7 ml), aqueous sodium carbonate solution (2 M, 1.55 ml) and toluene (6.9 ml) with heating at reflux for 1 hour. The residue obtained after work-up was purified by column chromatography over silica eluting with dichloromethane:methanol (92:8) to give the title compound (0.52 g) as an oil which crystallised from ethyl acetate and was recrystallised from isohexane/ethyl acetate.

m.p. 110–113° C.

MS (APCI) 377.2 (M+H)$^+$ $^1$H NMR (CDCl$_3$/DMSO-d$_6$) 9.50(1 H, br); 8.50(1 H, d); 8.42(1 H, dd); 7.84(1 H, t); 7.61(1 H, dt); 7.50(2 H, d); 7.32(1 H, t); 7.27-7.22(2 H, m); 6.97(2 H, d); 4.59(1 H, br); 4.00-3.92(3 H, m); 2.98-2.85(1 H, m); 2.83-2.75(1 H, m); 2.15(3 H, s); 1.98-1.82(2 H, m).

EXAMPLE 54

(R)-α-(6-(Benzyloxy)-2-naphthyloxymethyl)-3-pyridinepropanol

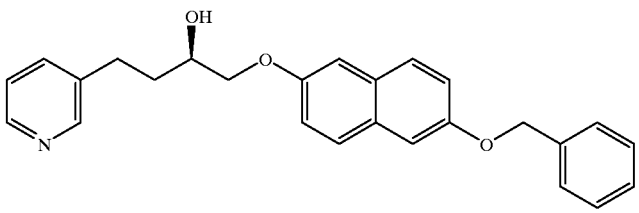

Sodium hydride (60% dispersion in mineral oil, 0.44 g) was washed with isohexane (2×5 ml) under a nitrogen atmosphere. Anhydrous N,N-dimethylformamide (5 ml) was added and then a solution of 2-benzyloxy-6-hydroxynaphthalene (2.76 g, Chem. Mater. 1993, 5, 938–942) in anhydrous N,N-dimethylformamide (40 ml) was added dropwise. After stirring at room temperature for 30 minutes a solution of (2R)-2-(tert-butyldimethylsilyloxy)-4-(3-pyridyl)-1-(4-toluenesulfonyloxy)butane (4.00 g) in anhydrous N,N-dimethylformamide (5 ml) was added. The mixture was stirred at 60° C. for 2 hours, then poured into water and extracted with ether. The combined organic extracts were dried over anhydrous magnesium sulfate, filtered and concentrated under reduced pressure. The residue was dissolved in acetonitrile (60 ml) and hydrofluoric acid (2 ml, 37%) was added. The mixture was stirred at room temperature for 2 hours, poured into saturated aqueous sodium hydrogen carbonate solution and extracted with ether. The combined organic extracts were dried over anhydrous magnesium sulfate, filtered and concentrated under reduced pressure. The residue was purified by column chromatography over silica eluting with isohexane:acetone (3:2) to give the title compound as a solid (3.44 g) which was recrystallised from ethyl acetate:isohexane.

m.p. 100–101° C.

MS (APCI) 400.2 (M+H)+

1H NMR (CDCl3) 8.53(1 H, d); 8.47(1 H, dd); 7.64(2 H, d);7.58(1 H, dt); 7.49(2 H, dd); 7.44-7.33(3 H, m); 7.24-7.18(3 H, m); 7.13(1 H, dd); 7.09( 1 H, d); 5.16(2 H, s); 4.10-4.05(2 H, m); 3.96(1 H, dd); 2.94-2.89(1 H, m); 2.86-2.75(1 H, m); 2.49(1 H, d); 2.05-1.83(2 H, m).

EXAMPLE 55

(±)-1-(3'-Acetylbiphenyl-4-yl)-5-(3-pyridyl)-3-pentanol

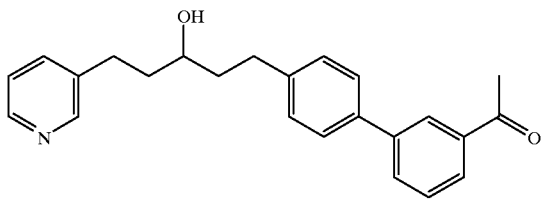

a) 3'-Acetyl-4-methoxybiphenyl

Prepared according to example 33a) from 3-bromoacetophenone (2.6 g), 4-methoxybenzeneboronic acid (2.0 g) and tetrakis(triphenylphosphine)palladium(0) (0.5 g) in toluene (18 ml), ethanol (4.8 ml) and aqueous sodium carbonate solution (2 M, 8.4 ml) with heating at reflux under nitrogen for 4 hours. The residue obtained after work-up was purified by column chromatography over silica eluting with ethyl acetate:isohexane (1:9) to give the sub-title compound as a crystalline solid (2.62 g).

m.p. 56–57° C.

GCMS (ESI) 226 (M)+

1H NMR (DMSO-d6) 8.14(1 H, t); 7.89(2 H, dd); 7.70(2 H, dt); 7.59(1 H, t); 7.07(2 H, dt); 3.81(3 H, s); 2.65(3 H, s).

b) 3'-Acetylbiphenyl-4-ol

A solution of 3'-acetyl-4-methoxybiphenyl (2.07 g) in hydrobromic acid (48%, 25 ml) and glacial acetic acid (25 ml) was heated at reflux under nitrogen for 1 hour. After cooling the mixture was poured into water and extracted with ether. The organic phase was washed with brine, dried over anhydrous magnesium sulfate, filtered and concentrated under reduced pressure to give a crude yellow/brown solid The latter was purified by column chromatography over silica eluting with diethyl ether:hexane (2:3) to give the sub-title compound as a cream/orange solid (1.47 g).

m.p. 146–149° C.

GCMS (ESI) 212 (M)+

1H NMR (DMSO-d6) 9.65(1 H, s); 8.10(1 H, t); 7.88-7.83(2 H, m); 7.58-7.54(3 H, m); 6.88(2 H, dt); 2.64(3 H, s).

c) 3'-Acetyl-4-trifluoromethanesulfonyloxybiphenyl

Solid N-phenyltrifluoromethanesulfonimide (2.0 g) was added to a suspension of 3'-acetylbiphenyl-4-ol (1.2 g) in dichloromethane (25 ml). The mixture was cooled to 4° C. and triethylamine (0.6 g) was added. The resulting yellow solution was allowed to warm to room temperature and then stirred for 2 hours. The reaction mixture was concentrated under reduced pressure and the residue purified by column chromatography over silica eluting with ethyl acetate:hexane (1:4) to give the sub-title compound as a yellow oil (1.82 g).

GCMS (ESI) 344 (M)+

1H NMR (DMSO-d6) 8.23(1 H, t); 8.02-7.92(4 H, m); 7.69-7.61(3 H, m); 2.67(3 H, s).

d) (±)-5-(3-Pyridyl)-1-(trimethylsilyl)pent-1-yn-3-ol

A solution of n-butyllithium (2.5 M in hexanes, 30 ml) was added dropwise to a solution of (trimethylsilyl) acetylene (11 ml) in tetrahydrofuran (100 ml) at –78° C. After addition was complete the solution was stirred for 10 minutes and then a solution of 3-(3-pyridyl)-1-propionaldehyde (10.0 g) in tetrahydrofuran (50 ml) was added. The reaction mixture was allowed to room temperature and a solution of saturated aqueous ammonium chloride was added. The mixture was extracted with ether, the combined extracts dried over anhydrous magnesium sulfate, filtered and concentrated under reduced pressure. The residue was purified by column chromatography over silica eluting with ethyl acetate to give an oil (13.2 g).

MS (EI) 233 (M)+

1H NMR (DMSO-d6) 8.43-8.38(2 H, m); 7.63(1 H, d); 7.31(1 H, dd); 5.51(1 H, d); 4.17(1 H, q); 2.75-2.65(2 H, m); 1.9-1.8(2 H, m); 0.15(9 H, s).

e) (±)-5-(3-Pyridyl)pent-1-yn-3-ol

Solid potassium carbonate (1.5 g) was added to a solution of (±)-5-(3-pyridyl)-1-(trimethylsilyl)pent-1-yn-3-ol (2.9 g) in methanol (50 ml) and the mixture stirred at room temperature for 24 hours. The methanol was removed under reduced pressure and water was added. The mixture was extracted with dichloromethane, the extracts dried over anhydrous magnesium sulfate, filtered and concentrated under reduced pressure. The residue was purified by column chromatography over silica eluting with ethyl acetate to give the sub-title compound as an oil (1.8 g) which was used immediately.

MS (EI) 161 (M)+ f) (±)-1-(3'-Acetylbiphenyl-4-yl)-5-(3-pyridyl)pent-1-yn-3-ol

3'-Acetyl-4-trifluoromethanesulfonyloxybiphenyl (2.0 g), (±)-5-(3-pyridyl)pent-1-yn-3-ol (1.4 g), bis (triphenylphosphine)palladium(II) chloride (0.2 g) in N,N-dimethylformamide (8 ml) and triethylamine (4.5 ml) were heated at 90° C. for 2 hours with stirring under nitrogen. After cooling the reaction was poured into water and extracted with dichloromethane. The organic solution was washed with brine, dried over anhydrous magnesium sulfate, filtered and concentrated under reduced pressure. The residue was purified by column chromatography over silica eluting with ethanol:dichloromethane (3:97) to give the sub-title compound as a pale yellow gum (1.33 g).

MS (APCI) 356 (M+H)+

1 H NMR (DMSO-d6) 8.49(1 H, d); 8.42(1 H, dd); 8.22(1 H, t); 7.96(2 H, dd); 7.78(2 H, d); 7.71-7.61(2 H, m); 7.57-7.35(2 H, m); 7.54-7.31(1 H, m); 5.67(1 H, d); 4.47(1 H, q); 2.83-2.77(2 H, m); 2.67(3 H, s) 2.03-1.95(2 H, m).

g) 1-(3'-Acetylbiphenyl-4-yl)-5-(3-pyridyl)-3-pentanol

A solution of 1-(3'-acetylbiphenyl-4-yl)-5-(3-pyridyl) pent- 1-yn-3-ol (0.7 g) in absolute ethanol (20 ml) was hydrogenated for 24 hours at 1.2 atmospheres using palladium on carbon (10%, 0.1 g) as catalyst. The reaction mixture was filtered through Celite® and the residue washed with ethanol. The combined filtrate and washings were concentrated under reduced pressure. The residue was purified by column chromatography over silica eluting with dichloromethane:methanol (97:3) to give the title compound as a colourless oil (0.25 g).

MS (APCI) 360 (M+H)+

1H NMR (DMSO-d6) 8.44(1 H, d); 8.38(1 H, dd); 8.17(1 H, t); 7.94-7.90(2 H, m); 7.65-7.58(4 H, m); 7.33-7.27(3 H, m); 4.67(1 H, d); 3.49-3.41(1 H, m); 2.78-2.59(7 H, m); 1.74-1.60(4 H, m).

EXAMPLE 56

(±)-1-(Biphenyl-3-yloxy)-4-(3-pyridyl)-2-butanol oxalic acid salt

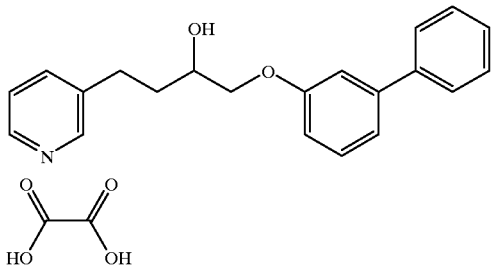

a) (±)-1-(3-Bromophenoxy)-4-(3-pyridyl)-2-butanol

Prepared according to the method described in Example 24b) from (±)-α-(chloromethyl)-3-pyridinepropanol (0.925 g), 3-bromophenol (1.73 g), ethanol (20 ml), sodium hydroxide (0.4 g) and water (5 ml) to give the sub-title compound as an oil (0.825 g).

MS (EI) 322/4 (M)$^+$ $^1$H NMR (CDCl$_3$) 8.50(1 H, d); 8.45(1 H, dd); 7.56-7.54(1 H, m); 7.25-7.20(1 H, m); 7.15-7.05(3 H, m); 6.82(1 H, dt); 4.0-3.95(2 H, m); 3.9-3.8(1 H, m); 3.0-2.7(2 H, m); 2.57(1 H, d); 1.95-1.85(2 H, m).

(b) (±)-1-(Biphenyl-3-yloxy)-4-(3-pyridyl)-2-butanol oxalic acid salt

Prepared according to the method described in Example 33a) from toluene (5 ml), aqueous sodium carbonate (2 M, 1 ml), (±)-1-(3-bromophenoxy)-4-(3-pyridyl)-2-butanol (0.25 g), ethanol (1 ml), benzeneboronic acid (0.14 g) and tetrakis(triphenylphosphine)palladium(0) (30 mg) with heating at reflux for 4 hours. The residue obtained after work up was purified by column chromatography over silica eluting with ethyl acetate to give (±)-1-(biphenyl-3-yloxy)-4-(3-pyridyl)-2-butanol as a colourless oil (0.178 g). Conversion to the oxalate salt upon treatment with excess saturated ethereal oxalic gave the title compound as a hygroscopic gum. (0.10 g)

MS (APCI) 320 ((M−oxalic acid)+H)$^+$ $^1$H NMR (DMSO-d$_6$) 8.50(1 H, s); 8.45(1 H, d); 7.50(1 H, d); 7.65-7.60(2 H, m); 7.50-7.45(2 H, m); 7.40-7.35(3 H, m); 7.25-7.15(2 H, m); 6.94(1 H, dd) 3.95(2 H, d); 3.85-2.90 (1 H, m) 2.85-2.65(2 H, m); 1.90-1.70(2 H, m).

EXAMPLE 57

(2R)-1-(3'-Chlorobiphenyl-4-ylthio)-4-(3-pyridyl)-2-butanol oxalic acid salt

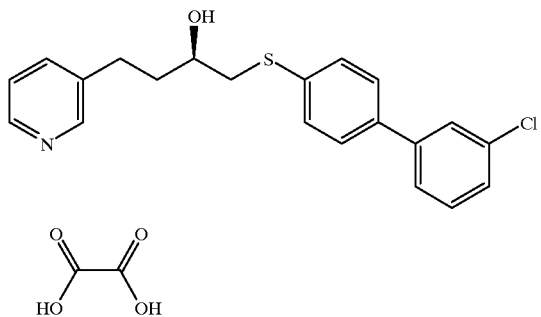

a) 3'-Chlorobiphenyl-4-yl N,N-dimethyl-O-thiocarbamate

Potassium hydroxide (0.56 g) was added to a stirring solution of 3'-chlorobiphenyl-4-ol (2.04 g) in tetrahydrofuran (75 ml) and water (25 ml) followed by N,N-dimethylthiocarbamoyl chloride (1.85 g). The mixture was stirred at room temperature for 5 hours and was then extracted with ethyl acetate (3×30 ml). The combined extracts were dried over anhydrous magnesium sulfate, filtered and concentrated under reduced pressure. The residue was purified by column chromatography over silica eluting with dichloromethane:hexane (1:1) to give the sub-title compound as an oil (2.02 g).

MS (ESI) 291/293 (M)$^+$ $^1$H NMR (CDCl$_3$) 7.60-7.56(3 H, m); 7.46(1 H, dt); 7.37-7.29(2 H, m); 7.15(2 H, d); 3.48(3 H, s); 3.37(3 H, s).

b) 3'-Chlorobiphenyl-4-yl N,N-dimethyl-S-thiocarbamate

A solution of 3'-chlorobiphenyl-4-yl N,N-dimethyl-O-thiocarbamate (1.96 g) in N,N-dimethylaniline (20 ml) was heated at reflux for 30 hours. After cooling, hydrochloric acid (2 M, 10 ml) was added and the mixture extracted with ethyl acetate (3×50 ml). The combined extracts were dried over anhydrous magnesium sulfate, filtered and concentrated under reduced pressure. The residue was purified by column chromatography over silica eluting with hexane:ethyl acetate (3:1) and the product recrystallised from diethyl ether to give the sub-title compound as white crystals (1.39 g).

m.p. 140–141° C.

MS (ESI) 291/293 (M)$^+$ $^1$H NMR (CDCl$_3$) 7.55(5 H, s);7.5-7.4(1 H, m); 7.35-7.25(2 H, m); 3.10-3.05(6 H, d).

c) (2R)-1-(3'-Chlorobiphenyl-4-ylthio)-4-(3-pyridyl)-2-butanol

Aqueous potassium hydroxide (4 M, 2 ml) was added to a solution of 3'-chlorobiphenyl-4-yl N,N-dimethyl-S-thiocarbamate in ethanol (10 ml). The solution was heated at 100° C. under nitrogen for 32 hours. A solution of (2R)-2-(tert-butyldimethylsilyloxy)-4-(3-pyridyl)-1-butyl para-toluenesulfonate (0.98 g) in ethanol (20 ml) was then added and heating was continued for 4 hours. The colourless oil obtained after work-up was dissolved in acetonitrile (20 ml). Hydrofluoric acid (40%, 6 ml) was added and the resulting solution stirred at room temperature for 3 hours. The reaction mixture was poured into aqueous sodium hydroxide solution (4 M, 100 ml) and was then extracted with ethyl acetate. The organic extract was dried over anhydrous magnesium sulfate, filtered and concentrated under reduced pressure. The residue obtained was purified by column chromatography over silica eluting with ethyl acetate to give an oil. Conversion to the oxalate salt upon treatment with excess saturated ethereal oxalic gave the title compound as a white solid (0.63 g).

m.p. 90–91° C.

MS (APCI) 370/372 ((M−oxalic acid)+H)$^+$ $^1$H NMR (DMSO-d$_6$) 8.50(1 H, s); 8.45(1 H, d); 7.70-7.65(1 H, m); 7.65-7.60(4 H, m); 7.50-7.45(1 H, m); 7.40-7.35(3 H, m); 7.35-7.30(1 H, m); 3.65-3.60(1 H, m) 3.05(2 H, d); 2.75-2.60(2 H, m) 1.90-1.85(1 H, m); 1.75-1.70(1 H, m).

EXAMPLE 58

(2R)-1-(3'-Hydroxymethylbiphenyl-4-yloxy)-4-(3-pyridyl)-2-butanol

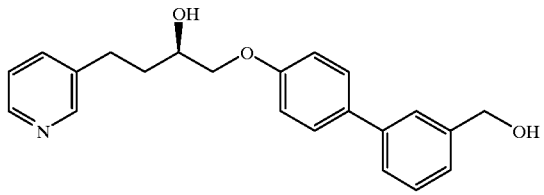

a) 3'-Carboxybiphenyl-4-ol

A solution of 3'-cyanobiphenyl-4-ol (1.65 g, Example 36b)) in aqueous potassium hydroxide solution (4 M, 20 ml) was heated for 8 hours at 140° C. After cooling, the solution was acidified with concentrated hydrochloric acid, the resulting precipitate filtered and washed with water to give the sub-title compound as a white solid (1.6 g).

m.p. >200° C.

MS (APCI) 215 (M+H)$^+$ $^1$H NMR (DMSO-d$_6$) 13.05(1 H, bs); 9.65(1 H, bs); 8.11(1 H; t); 7.90-7.80(2 H, m); 7.55-7.50(3 H, m); 6.90-6.85(2 H, m)

b) 3'-Methoxycarbonylbiphenyl-4-ol

Solid 3'-carboxybiphenyl-4-ol (1.5 g) was suspended in methanol (10 ml) and concentrated sulfuric acid (1 ml). The mixture was heated at reflux for 16 hours. After cooling, the mixture was basified by the addition of solid sodium hydrogen carbonate. The white solid which formed was filtered and washed with copious amounts of water to give the sub-title compound as a white solid (1.5 g).

m.p. 135–136° C.

MS (APCI) 229 (M+H)$^+$ $^1$H NMR (CDCl$_3$) 8.23(1 H, t); 7.96(1 H, dt); 7.73(1 H, dt); 7.55-7.45(3 H, m); 6.93(2 H, dt); 5.07(1 H, s); 3.95(3 H, s).

c) 3'-Hydroxymethylbiphenyl-4-ol

A solution of lithium aluminium hydride (1 M in ether, 2.5 ml) was added to dry tetrahydrofuran (10 ml) and the solution cooled to 0° C. A solution of 3'-methoxycarbonylbiphenyl-4-ol in (0.57 g) in tetrahydrofuran (10 ml) was then added and the resulting solution stirred at room temperature for 30 minutes. The reaction was then quenched by the addition of water (0.1 ml) followed by aqueous sodium hydroxide (50%, 0.1 ml) and then water (0.5 ml). The mixture was acidified with dilute aqueous hydrochloric acid (2 M) and extracted with ethyl acetate. The organic extract was dried over anhydrous magnesium sulfate, filtered and concentrated under reduced pressure to give the sub-title compound as a white solid (0.48 g).

MS (APCI) 201 (M+H)$^+$ $^1$H NMR (DMSO-d$_6$) 7.50-7.40(4 H, m); 7.35(1 H, t); 7.22(1 H, d); 6.84(2 H, dt); 5.21(1 H, t); 4.54(2 H, d).

d) (2R)-1-(3'-Hydroxymethylbiphenyl-4-yloxy)-4-(3-pyridyl)-2-butanol

Prepared according to the method described in Example 26e) from (2R)-2-(tert-butyldimethylsilyloxy)-4-(3-pyridyl)-1-butyl para-toluenesulfonate (0.68 g), sodium hydride (60%, 0.073 g) and 3'-hydroxymethylbiphenyl-4-ol (0.39 g) in N,N-dimethylformamide (10 ml). The adduct was deprotected by dissolving in tetrahydrofuran (10 ml) to which tetrabutylammonium fluoride (0.93 g) was added. The reaction was stirred at ambient temperature for 1 hour, poured into brine and extracted with ethyl acetate. The combined organic extracts were dried over anhydrous magnesium sulfate, filtered and concentrated under reduced pressure. The residue was purified by column chromatography over silica eluting with ethyl acetate to give the title compound (0.2 g) as a white solid.

m.p. 108° C.

MS (APCI) 350 (M+H)$^+$ $^1$H NMR (CDCl$_3$) 8.50(1 H, d); 8.45(1 H, dd); 7.60-7.50(4 H, m); 7.45-7.40(2 H, m); 7.35-7.30(1 H, m); 7.25-7.20(1 H, m); 7.00-6.95(2 H, m); 4.75(2 H, s); 4.05-4.00(2 H, m); 3.95-3.90(1 H, m); 2.95-2.75(2 H, m); 2.40(1 H, s); 1.95-1.85(2 H, m).

EXAMPLE 59

(±)-1-(3'-Chlorobiphenyl-4-yl)-5-(3-pyridyl)-3-pentanol oxalic acid salt

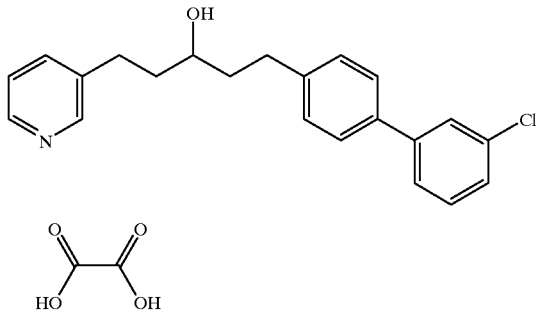

a) 3'-Chloro-4-trifluoromethanesulfonyloxybiphenyl

3'-Chlorobiphenyl-4-ol (Example 33b, 2.04 g) was dissolved in dry pyridine (10 ml) and cooled to 0° C. Trifluromethanesulfonic anhydride (1.94 ml) was then added dropwise and the resulting mixture stirred for 2 hours. The reaction mixture was poured into dilute hydrochloric acid (2 M, 200 ml) and extracted with ethyl acetate. The combined organic extracts were dried over anhydrous magnesium sulfate, filtered and concentrated under reduced pressure. The residue was purified by column chromatography over silica eluting with hexane to give the sub-title compound as an oil (3.22 g).

MS (ESI) 336/338 (M+H)$^+$ $^1$H NMR (CDCl$_3$) 7.63(2 H, d); 7.53(1 H, s); 7.45-7.33(5 H, m).

b) (±)-1-(3'-Chlorobiphenyl-4-yl)-5-(3-pyridyl)-3-pentanol oxalic acid salt

Prepared according to the method described in Example 7b) from (±)-5-(3-pyridyl)-1-penten-3-ol (Example 7a, 0.66 g), 3'-chloro-4-trifluoromethanesulfonyloxybiphenyl (1.34 g), palladium(II) acetate (0.09 g), tri-o-tolylphosphine (5 ml) and triethylamine (1 ml) at 80° C. for 5 hours. Work up and purification by column chromatography over silica eluting with dichloromethane:methanol (19:1) gave (±)-1-(3'-chlorobiphenyl-4-yl)-5-(3-pyridyl)-3-pentanone (0.4 g). The latter was immediately dissolved in methanol (10 ml), cooled to 0° C. and sodium borohydride (0.043 g) added. The reaction mixture was stirred at 25° C. for 2 hours and was then concentrated under reduced pressure. Water was added to the residue and the mixture extracted with ethyl acetate. The combined extracts were dried over anhydrous magnesium sulfate, filtered and concentrated under reduced pressure. The residue was purified by column chromatography over silica eluting with ethyl acetate. Conversion to the oxalate salt upon treatment with excess saturated ethereal oxalic acid gave the title compound as a solid (0.094 g).

m.p. 104–105° C.

MS (APCI) 352/354 ((M−oxalic acid)+H)+

$^1$H NMR (DMSO-$d_6$) 8.45(1 H, s); 8.40(1 H, d); 7.70-54(5 H, m); 7.50(1 H, t); 7.41(1 H, dt); 7.38-7.34(1 H, m); 7.30(2 H, d); 3.45-2.85(1 H, m); 2.83-2.62(2 H, m); 2.64-2.58(2 H, m); 1.75-1.57(4 H, m).

EXAMPLE 60

(2R)-1-[6-Cyclopropylmethoxy)-2-naphthyloxy]-4-(3-pyridyl)-2-butanol

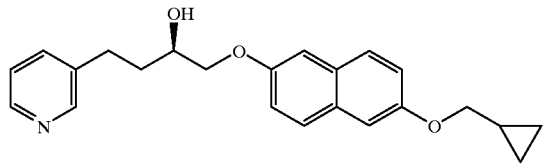

a) 2-Cyclopropylmethoxy-6-hydroxynaphthalene

A mixture of 2,6-dihydroxynaphthalene (4.00 g), anhydrous potassium carbonate (3.45 g) and cyclopropylmethyl bromide (2.63 ml) in anhydrous N,N-dimethylformamide (15 ml) and acetone (60 ml) was stirred at reflux under a nitrogen atmosphere for 16 hours. After cooling to room temperature the reaction was poured into water and extracted with ether. The combined organic extracts were dried over anhydrous magnesium sulfate and concentrated under reduced pressure. The residue was purified by column chromatography over silica eluting with dichloromethane to give the sub-title compound as a solid (1.72 g).

MS (EI) 214 (M)+

$^1$H NMR (CDCl$_3$) 7.62(1 H, d); 7.59(1 H, d); 7.16(1 H, dd); 7.13-7.04(3 H, m); 4.82(1 H, s); 3.89(2 H, d); 1.38-1.27(1 H, m); 0.71-0.64(2 H, m); 0.42-0.36(2 H, m).

b) (2R)-1-[6-(Cyclopropylmethoxy)-2-naphthyloxy]-4-(3-pyridyl)-2-butanol

A solution of 2-cyclopropylmethoxy-6-hydroxynaphthalene (0.270 g) in anhydrous N,N-dimethylformamide (10 ml) was added dropwise to sodium hydride (60% dispersion in mineral oil, 0.457 g) that had been previously washed with isohexane (2 ml) under a nitrogen atmosphere. After stirring at 20° C. for 20 minutes a solution of (2R)-2-(tert-butyldimethylsilyloxy)-4-(3-pyridyl)-1-(4-toluenesulfonyloxy)butane (0.46 g) in anhydrous N,N-dimethylformamide (2 ml) was added and the mixture stirred at 60° C. for 90 minutes. After cooling the reaction was poured into saturated aqueous sodium hydrogen carbonate solution and extracted with ether. The combined organic extracts were dried over anhydrous magnesium sulfate, filtered and concentrated under reduced pressure. The residue was dissolved in tetrahydrofuran (50 ml) and treated with tetrabutylammonium fluoride hydrate (0.48 g). After 1 hour the solution was diluted with water and extracted with ether. The organic extract was dried over anhydrous magnesium sulfate, filtered and concentrated under reduced pressure. The residue was purified by column chromatography over silica eluting with dichloromethane:methanol (24:1) to give the title compound as a solid (0.124 g) which was recrystallised from ethyl acetate/isohexane.

m.p. 107–108° C.

MS (APCI) 364.1 (M+H)+

$^1$H NMR (CDCl$_3$) 8.53(1 H, s); 8.47(1 H, d); 7.62(2 H, d); 7.58(1 H, d); 7.24-7.07(5 H, m); 4.09-4.02(2 H, m); 3.96(1 H, dd); 3.89(2 H, d); 2.99-2.77(2 H, m); 2.47(1 H, br); 2.00-1.83(2 H, m); 1.42-1.22(2 H, m); 0.71-0.64(2 H, m); 0.42-0.36(2 H, m).

EXAMPLE 61

(±)-(E)-1-(4-(2-Phenylethenyl)phenoxy)-4-(3-pyridyl)-2-butanol

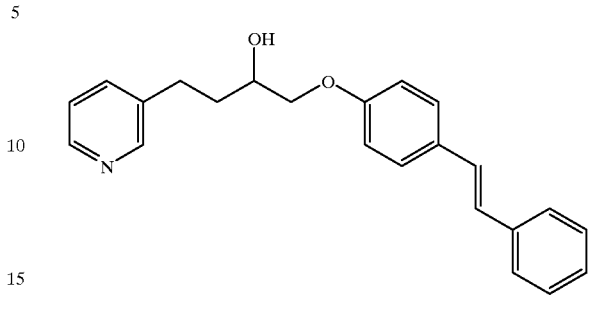

Prepared according to the method described in Example 24b) from trans-4-hydroxystilbene (2.6 g), (±)-α-(chloromethyl)-3-pyridinepropanol (2.5 g) and sodium hydroxide (0.54 g) in ethanol (50 ml) and water (10 ml) at reflux for 2 hours to give the title compound as a solid (1.84 g)

m.p. 110–111° C.

MS (APCI) 346 (M+H)+

$^1$H NMR (DMSO-$d_6$) 8.47(1 H, d); 8.40(1 H, dd); 7.66(1 H, dt); 7.58-7.51(4 H, m); 7.38-7.21(4 H, m); 7.20(1 H, d); 7.09(1 H, d); 6.95(2 H, d); 5.07(1 H, d); 3.91(2 H, d); 3.81-3.76(1 H, m); 2.81-2.76(1 H, m); 2.73-2.67(1 H, m); 1.86-1.83(1 H, m); 1.74-1.70(1 H, m).

EXAMPLE 62

(±)-1-(4-(2-Phenylethyl)phenoxy)-4-(3-pyridyl)-2-butanol

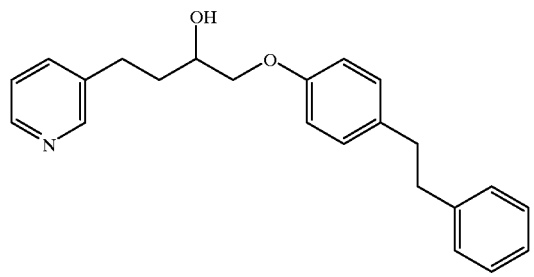

A solution of (±)-(E)-1-(4-(2-phenylethenyl)phenoxy)-4-(3-pyridyl)-2-butanol (0.32 g, Example 61) was dissolved in dry ethanol (50 ml) and hydrogenated for 24 hours at 3 atmospheres using palladium on carbon (10%, 0.1 g) as catalyst. The reaction mixture was filtered through Celite® and the residue washed with ethanol. The filtrate and washings were combined and concentrated under reduced pressure. The residue was purified by column chromatography over silica eluting with dichloromethane:methanol (95:5) to give the title compound as a white solid (0.29 g).

m.p. 95–96° C.

MS (APCI) 348 (M+H)+

$^1$H NMR (DMSO-$d_6$) 8.45(1 H, d); 8.39(1 H, dd); 7.64(1 H, dt); 7.33-7.13(6 H, m); 7.11(2 H, d); 6.81(2 H, d); 5.02(1 H, d); 3.83(2 H, d); 3.76-3.73(1 H, m); 2.83-2.66(6 H, m); 1.84-1.81(1 H, m); 1.70-1.67(1 H, m).

EXAMPLE 63

(2R)-1-(4'-Cyanobiphenyl-4-yloxy)-4-(3-pyridyl)-2-butanol

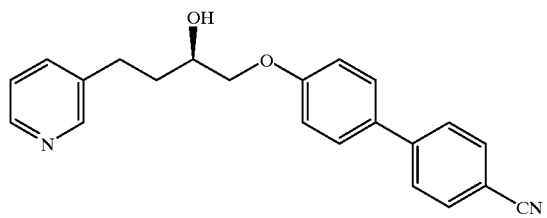

Prepared according to the method described in Example 26e) from (2R)-2-(tert-butyldimethylsilyloxy)-4-(3-pyridyl)-1-butyl para-toluenesulfonate (0.281 g), sodium hydride (60% dispersion in mineral oil, 0.056 g) and 4'-cyanobiphenyl-4-ol (0.269 g) in N,N-dimethylformamide (5 ml). The adduct was dissolved in tetrahydrofuran (10 ml) and tetrabutylammonium fluoride (0.522 g) was added. The reaction was stirred at room temperature for 1 hour and then poured into brine and extracted with ethyl acetate. The combined organic extracts were dried over anhydrous magnesium sulfate, filtered and concentrated under reduced pressure. The residue was purified by column chromatography over silica eluting with ethyl acetate to give the title compound as a solid (0.081 g).

m.p. 135–136° C.

MS (APCI) 345 (M+H)+

$^1$H NMR (CDCl$_3$) 8.52(1 H, d); 8.47(1 H, dd); 7.69(2 H, dd); 7.64-7.51(5 H, m); 7.50-7.22(1 H, m); 7.01(2 H, d); 4.04-3.91(3 H, m); 3.05-2.95(1 H, br); 2.94-2.80(2 H, m); 1.98-1.87(2 H, m).

EXAMPLE 64

(2R)-1-(3'-Acetylbiphenyl-4-yloxy)-4-(3-pyridyl)-2-butanol

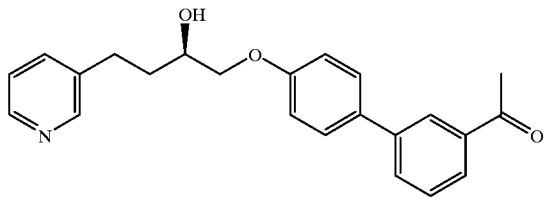

Prepared according to method described in Example 26e) from 3'-acetylbiphenyl-4-ol (Example 55b), 0.59 g), (2R)-4-(tert-butyldimethylsilyloxy)-4-(3-pyridyl)-1-(4-toluenesulfonyloxy)butane (1.0 g) and sodium hydride (60% dispersion in mineral oil, 0.12 g) in dry N,N-dimethylformamide (10 ml). Crude material from this reaction was dissolved in acetonitrile (15 ml) and treated with hydrofluoric acid (40%, 5 ml). The reaction mixture was stirred at room temperature for 18 hours and then poured into water (25 ml). The pH was adjusted to 9 by adding sodium hydroxide solution (2 M). The mixture was then extracted with ethyl acetate (3×100 ml) and the combined extracts dried over anhydrous magnesium sulfate. The solution was filtered and then concentrated under reduced pressure. The residue was purified by column chromatography over silica eluting with ethyl acetate to give the title compound as a white solid (0.25 g).

m.p. 58–60° C.

MS (APCI) 362 (M+H)+

$^1$H NMR (DMSO-d$_6$) 8.47(1 H, s); 8.41-8.39(1 H, d); 8.14(1 H, s); 7.90-7.88(2 H, dd); 7.69-7.66(2 H, d); 7.61-7.56(2 H, t); 7.34-7.30(1 H, m); 7.07-7.04(2 H, d); 5.10-5.08(1 H, d); 3.95-3.94(2 H, d); 3.84-3.75(1 H, m); 2.86-2.65(5 H, m); 1.95-1.63(2 H, m).

EXAMPLE 65

(2R)-1-(3'-Chloro-4'-fluorobiphenyl-4-yloxy)-4-(3-pyridyl)-2-butanol oxalic acid salt

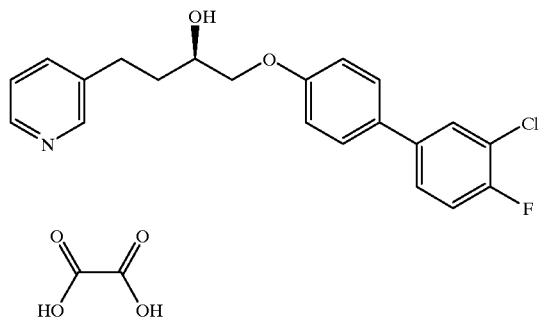

Aqueous sodium carbonate solution (2 M, 1.25 ml) was added to a solution of (2R)-1-(4-bromophenoxy)-4-(3-pyridyl)-2-butanol (0.4 g), 3-chloro-4-fluorobenzeneboronic acid (0.33 g) and tetrakis(triphenylphosphine)palladium(0) (0.05 g) in ethanol (0.8 ml) and toluene (3 ml). The mixture was stirred at reflux under a nitrogen atmosphere for 3 hours. After cooling to room temperature the reaction was diluted with water and extracted with ethyl acetate. The organic extracts were dried over anhydrous magnesium sulfate, filtered and concentrated under reduced pressure. The residue was purified by column chromatography over silica eluting with dichloromethane:acetone (3:1) followed by preparative reverse-phase HPLC on a (microBondapak) column with 0.1% aqueous trifluoroacetic acid/methanol gradient elution. Conversion to the oxalate salt upon treatment with excess saturated ethereal oxalic acid gave a solid which was washed with ether and recrystallised from acetonitrile to give the title compound (0.08 g)

m.p. 135–136° C.

MS (APCI) 372.1/374.0 (M+H)+

$^1$H NMR (DMSO-d$_6$) 8.48(1 H, d); 8.42(1 H, dd); 7.82(1 H, dd); 7.70(1 H, dt); 7.66-7.60(3 H, m); 7.46(1 H, t); 7.34(1 H, dd); 7.02(2 H, d); 3.93(2 H, d); 3.83-3.75( 1 H, m); 2.8-2.77(1 H, m); 2.74-2.64(1 H, m); 1.92-1.80(1 H, m); 1.78-1.66(1 H, m).

EXAMPLE 66

(2R)-1-(4'-Chlorobiphenyl-4-yloxy)-4-(3-pyridyl)-2butanol

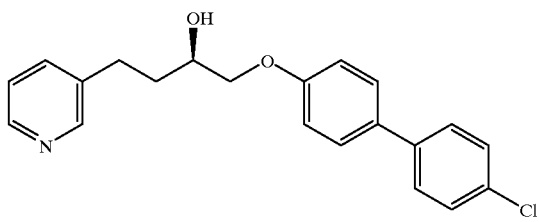

Prepared according to the method described in Example 65 from (2R)-1-(4-bromophenoxy)-4-(3-pyridyl)-2-butanol (0.25 g), 4-chlorobenzeneboronic acid (0.180 g) and tetrakis(triphenylphosphine)palladium(0) (40 mg) in toluene (5 ml), aqueous sodium carbonate (2 M, 1 ml) and ethanol (1 ml) with heating at reflux for 4 hours. The residue obtained after work up was purified by column chromatography over silica eluting with ethyl acetate to give the title compound as a white solid (0.104 g).

m.p. 117–118° C.

MS (APCI) 354/356 $(M+H)^+$ $^1$H NMR (CDCl$_3$) 8.50(1 H, d); 8.45(1 H, dd); 7.57(1 H, dt); 7.51-7.45(4 H, m); 7.40-7.45(2 H, m) 7.25-7.20(1 H, m); 6.97(2 H, dt); 4.05-4.00(2 H, m); 3.90(1 H, dd); 3.0-2.70(2 H, m); 2.45(1 H, d); 2.0-1.8(2 H, m).

EXAMPLE 67

(±)-α-(Phenylthiomethyl)-3-pyridinepropanol

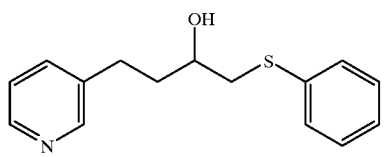

Prepared according to the method described in Example 1a) from thiophenol (0.142 g), sodium hydride (0.062 g) and 3-(2-oxiranylethyl)pyridine (0.150 g) in dimethylformamide at room temperature to give the title compound as an oil (0.200 g).

MS (EI) 259 $(M)^+$ $^1$H NMR (CDCl$_3$) 8.5(2 H, s); 7.5-7.1(7 H, m); 3.7(1 H, m); 3.1(1 H, dd); 3.0-2.6(4 H, m); 1.8(2 H, m).

EXAMPLE 68

(±)-α-(Phenoxymethyl)-3-pyridinepropanol

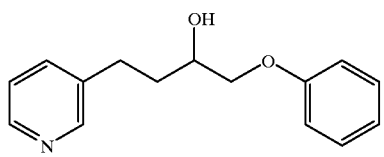

Prepared according to the method described in Example 1a) from phenol (0.15 g), sodium hydride (0.075 g) and 3-(2-oxiranylethyl)pyridine (0.15 g) in dimethylformamide at 100° C. for 30 minutes to give the title compound as an oil (0.04 g).

MS (EI) 243 $(M)^+$ $^1$H NMR (CDCl$_3$) 8.5(2 H, m); 7.5(1 H, m); 7.3-6.9(6 H, m); 4.0(2 H, m); 3.85(1 H, m); 3.0-2.7(2 H, m); 2.6(1 H, m); 1.9(2 H, m).

EXAMPLE 69

(±)-4-(3-Pyridyl)-1-(4-(thiazol-2-yl)phenoxy)-2-butanol

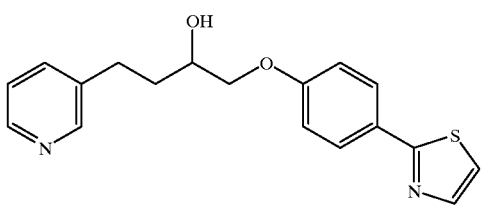

a) 2-(4-Methoxyphenyl)thiazole

Prepared according to the method described in Example 33a) from toluene (28 ml), aqueous sodium carbonate (2 M, 13 ml), 4-methoxybenzeneboronic acid (2 g), ethanol (6 ml), 2-bromothiazole (2.14 g) and tetrakis(triphenylphosphine)palladium(0) (0.36 g) with heating at 120° C. for 5 hours. After work up the residue was purified by column chromatography over silica with ethyl acetate:hexane (1:3) to give the sub-title compound as a pale yellow solid (1.7 g).

$^1$H NMR (CDCl$_3$) 7.9(2 H, d); 7.8(1 H, d); 7.25(1 H, d); 6.95(2 H, d); 3.85(3 H, s).

b) 2-(4-Hydroxyphenyl)thiazole

Prepared according to the method described in Example 36b) from 2-(4-methoxyphenyl)thiazole (1.7 g), dichloromethane (20 ml) and boron tribromide (1.0 M in dichloromethane, 17.8 ml) with stirring at −78° C. After work up the residue was triturated with ether to give the sub-title compound a pale yellow solid (1.2 g).

$^1$H NMR (DMSO-d$_6$) 10.0(1 H, s); 7.85-7.75(3 H, m); 7.63(1 H, d); 6.9-6.83(2 H, dd).

c) (±)-4-(3-Pyridyl)-1-(4-(thiazol-2-yl)phenoxy)-2-butanol

Prepared according to the method as described in Example 24b) from 2-(4-hydroxyphenyl)thiazole (1 g), ethanol (20 ml), sodium hydroxide (0.255 g), water (5 ml) and (±)-α-(chloromethyl)-3-pyridinepropanol (1 g, from Example 24a)) to give the title compound after purification as a white solid (0.42 g).

m.p. 93–96° C.

MS (FAB) 327 $(M+H)^+$ $^1$H NMR (DMSO-d$_6$) 8.45(1 H, d); 8.4(1 H, dd); 7.9-7.85(3 H, m); 7.7-7.63(2 H, m); 7.3(1 H, q); 7.05(2 H, d); 5.12(1 H, d); 4.0-3.9(2 H, m); 3.85-3.75(1 H, m); 2.87-2.63(2 H, m); 1.9-1.65(2 H, m).

EXAMPLE 70

(±)-1-(4-Benzoylphenoxy)-4-(3-pyridyl)-2-butanol

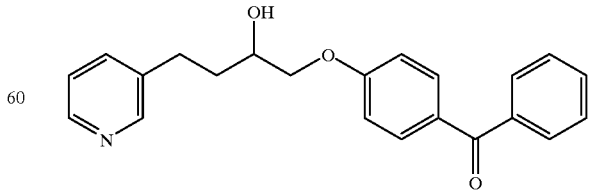

Prepared according to the method described in Example 24b) from (±)-α-(chloromethyl)-3-pyridinepropanol (1.05 g), 4-hydroxybenzophenone (1.35 g), ethanol (30 ml) and aqueous sodium hydroxide (1.4 M, 5 ml). After work up the residue was purified by column chromatography over silica with ether then ethyl acetate to give the title compound as an oil (0.42 g).

MS (EI) 347 (M)+

$^1$H NMR (DMSO-d$_6$) 8.47(1 H, d); 8.40(1 H, dd); 7.74(2 H, d); 7.72-7.63(4 H, m); 7.55(2 H, t); 7.31(1 H, dd); 7.09(2 H, d); 5.14(1 H, d); 4.05-3.95(2 H, m); 3.85-3.75(1 H, m); 2.88-2.75(1 H, m); 2.75-2.65(1 H, m); 1.93-1.68(2 H, m).

EXAMPLE 71

(±)-4-(3-Pyridyl)-1-(4-(3-pyridyl)phenoxy)-2-butanol

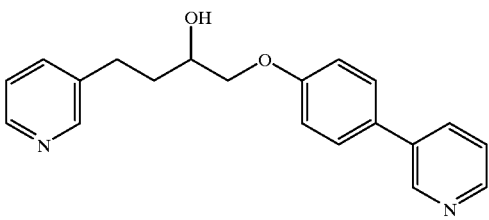

a) 3-(4-methoxyphenyl)pyridine

Prepared according to the method described in Example 33a) from toluene (28 ml), aqueous sodium carbonate (2 M, 13 ml), 4-methoxybenzeneboronic acid (2 g), ethanol (6 ml), 3-bromopyridine (2.06 g) and tetrakis(triphenylphosphine) palladium(0) (0.36 g) with heating at 120° C. for 4 hours. After work up the residue was purified by column chromatography over silica eluting with ethyl acetate:hexane (1:1) to give the sub-title compound as a white crystalline solid (1.9 g).

MS (EI) 185 (M)+

$^1$H NMR (CDCl$_3$) 8.8(1 H, d); 8.55(1 H, dd); 7.83(1 H, dt); 7.55-7.5(2 H, m); 7.35-7.3(1 H, m); 7.05-7.0(2 H, m); 3.86(3 H, s).

b) 3-(4-Hydroxyphenyl)pyridine

Prepared according to the method as described in Example 33b) from 3-(4-methoxyphenyl)pyridine (2.5 g), 48% aqueous hydrobromic acid (25 ml) and acetic acid (25 ml) to give the sub-title compound as a pale orange solid (1.68 g).

MS (EI) 171 (M)+

$^1$H NMR (DMSO-d$_6$) 9.7(1 H, s); 8.8(1 H, d); 8.47(1 H, dd); 7.98(1 H, dt); 7.6-7.53(2 H, m); 7.42(1 H, q); 6.9-6.85(2 H, m).

c) (±)-4-(3-pyridyl)-1-(4-(3-pyridyl)phenoxy)-2-butanol

Prepared according to the method as described in Example 24b) from 3-(4-hydroxyphenyl)pyridine (1.68 g), ethanol (30 ml), sodium hydroxide (0.393 g), water (10 ml) and (±)-α-(chloromethyl)-3-pyridinepropanol (0.91 g, Example 24a)) to give the title compound as a pale yellow solid (0.6 g).

m.p. 87–89° C.

MS (EI) 320 (M)+

$^1$H NMR (DMSO-d$_6$) 8.85(1 H, d); 8.5(1 H, d); 8.47(1 H, s); 8.4(1 H, d); 8.02(1 H, dd); 7.65(3 H, m); 7.47-7.42(1 H, m); 7.35-7.28(1 H, m); 7.05(2 H, d); 5.1(1 H, d); 4.0-3.9(2 H, m); 3.35-3.27(1 H, m); 2.87-2.65(2 H, m); 1.92-1.67(2 H, m).

EXAMPLE 72

(±)-1-(4-Benzoylphenyl)-5-(3-pyridyl)-3-pentanol

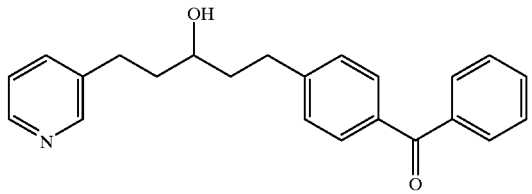

a) (±)-1-(4-Benzoylphenyl)-5-(3-pyridyl)pent-1-yn-3-ol

Prepared according to the method described in Example 55f) from 4-bromobenzophenone (0.93 g), (±)-5-(3-pyridyl)pent-1-yn-3-ol (0.58 g, Example 55e), bis(triphenylphosphine)palladium(II) chloride (0.252 g), copper(I) iodide (0.035 g) and triethylamine (10 ml), stirring at room temperature for 2 hours. After work up the residue was purified by column chromatography over silica with dichloromethane:ethanol (95:5) to give the sub-title compound as a pale yellow oil (0.6 g).

MS (ESI) 342 (M+H)+

$^1$H NMR (DMSO-d$_6$) 8.5(1 H, s); 8.43(1 H, s); 7.78-7.65(6 H, m); 7.63-7.55(4 H, m); 7.33(1 H, q); 5.75(1 H, d); 4.53-4.45(1 H, m); 2.83-2.75(2 H, m); 2.05-1.95(2 H, m).

b) (±)-1-(4-Benzoylphenyl)-5-(3-pyridyl)-3-pentanol

Prepared according to the method as described in Example 55g) from (±)-1-(4-benzoylphenyl)-5-(3-pyridyl)pent-1-yn-3-ol (0.6 g) in ethanol (10 ml), hydrogenated at 1.5 atmospheres for 18 hours using palladium on carbon (10%, 0.05 g). The residue was purified by column chromatography over silica with dichloromethane:ethanol (95:5) to give the title compound as an off white gum (0.387 g).

MS (ESI) 346 (M+H)+

$^1$H NMR (DMSO-d$_6$) 8.43(1 H, s); 8.35(1 H, d); 7.75-7.52(8 H, m); 7.37(2 H, d); 7.28(1 H, q); 4.7(1 H, d); 3.45-3.38(1 H, m); 2.88-2.55(4 H, m); 1.8-1.57(4 H, m).

EXAMPLE 73

(±)-1-(3'-Methoxybiphenyl-4-yloxy)-4-(3-pyridyl)-2-butanol

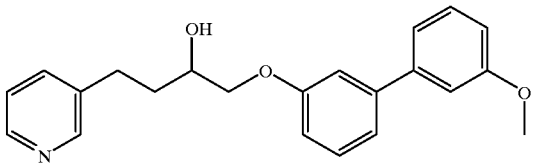

Prepared according to the method as described in Example 33a) from toluene (8 ml), aqueous sodium carbonate (2 M, 2.47 ml), 3-methoxybenzeneboronic acid (0.413 g), ethanol (2 ml), (±)-1-(3-bromophenoxy)-4-(3-pyridyl)-2-butanol (0.79 g, Example 56a) and tetrakis(triphenylphosphine)palladium(0) (0.071 g) with heating at 120° C. for 4 hours. After work up the residue was purified by column chromatography over silica with ethyl acetate to give the title compound as a white solid after trituration with ether:hexane (0.27 g).

m.p. 76–78° C.

MS (APCI) 350 (M+H)+

$^1$H NMR (DMSO-d$_6$) 8.45(1 H, s); 8.4(1 H, d); 7.65(1 H, d); 7.4-7.38(3 H, m); 7.25-7.15(4 H, m); 6.95(2 H, dd);

5.08(1 H, d); 3.95(2 H, d); 3.85-3.75(4 H, m); 2.85-2.63(2 H, m); 1.91-1.68(2 H, m).

EXAMPLE 74

(2R)-1-(3'-Methanesulfonamidobiphenyl-4-yloxy)-4-(3-pyridyl)-2-butanol

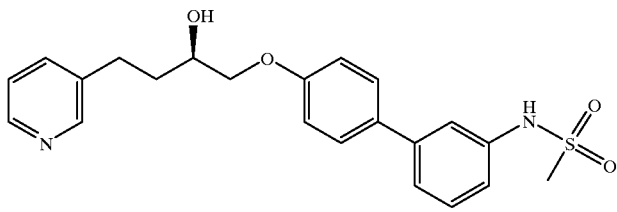

Methanesulfonyl chloride (0.334 ml) was added to a stirred solution of 3-aminoboronic acid monohydrate (0.30 g) in ethanol (2 ml). After 20 minutes, aqueous sodium carbonate solution (2 M, 2.16 ml) and sodium carbonate (0.687 g) were added followed by further methanesulfonyl chloride (0.167 ml). After 10 minutes, (2R)-1-(4-bromophenoxy)-4-(3-pyridyl)-2-butanol (0.50 g), tetrakis (triphenylphosphine)palladium(0) (45 mg), toluene (8 ml) and further ethanol (2 ml) were added. The mixture was heated at reflux under nitrogen for 4 hours. The cooled reaction mixture was diluted with water (50 ml) and extracted with ether (3×50 ml) then with ethyl acetate (6×50 ml). The combined organic extracts were dried over anhydrous magnesium sulfate, filtered and concentrated under reduced pressure. The residue was purified by column chromatography over silica eluting with dichloromethane:methanol (93:7) to give the title compound (0.218 g) as a foam which was further purified by column chromatography over silica eluting with dichloromethane:methanol:saturated aqueous ammonia solution (89:10:1) to give a foam.

MS (APCI) 411.1 (M−H)⁻

¹H NMR (CDCl₃) 8.53(1 H, d); 8.47(1 H, dd); 7.57(1 H, dt); 7.51(2 H, d); 7.44-7.36(3 H, m); 7.24(1 H, dd); 7.16(1 H, dt); 6.97(2 H, d); 6.67(1 H, s); 4.09-3.98(2 H, m); 3.91(1 H, dd); 3.05(3 H, s); 2.99-2.88(1 H, m); 2.85-2.75(1 H, m); 2.48(1 H, br); 2.02-1.80(2 H, m).

EXAMPLE 75

(2R)-4-(3-Pyridyl)-1-(4-(2-thiazolin-2-yl)phenoxy)-2-butanol dioxalic acid salt

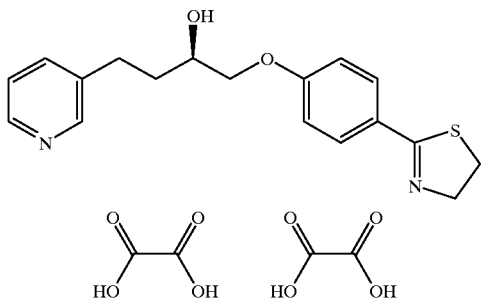

Sodium hydride (60% dispersion in mineral oil, 0.032 g) was washed with isohexane (2 ml) under a nitrogen atmosphere. A solution of 4-(2-thiazolin-2-yl)phenol (0.123 g, ex-Maybridge) in anhydrous dimethylformamide (2 ml) was added dropwise. After stirring at room temperature for 30 minutes a solution of (2R)-2-(tert-butyldimethylsilyloxy)-4-(3-pyridyl)-1-butyl para-toluenesulfonate (0.25 g) in anhydrous dimethylformamide (1 ml) was added. The mixture was stirred at 60° C. for 3 hours, then poured into water and extracted with ethyl acetate. The organic extracts were dried over anhydrous magnesium sulfate, filtered and concentrated under reduced pressure. The residue was dissolved in acetonitrile (5 ml) and hydrofluoric acid (37%, 2 ml) added. The mixture was stirred at room temperature for 48 hours, poured into saturated sodium bicarbonate solution and extracted with ethyl acetate. The organic extracts were dried over anhydrous magnesium sulfate, filtered and concentrated under reduced pressure. The residue was purified by column chromatography over silica eluting with dichloromethane:methanol (19:1) to give an oil (0.136 g) which was redissolved in ether/ethyl acetate (12 ml, 5/1) and treated with a saturated solution of oxalic acid in ether (2 ml). The liquid was decanted from the resulting waxy solid which was triturated with ethyl acetate and collected by filtration to give the title compound as a powdery solid (0.135 g).

m.p. 131–132° C.

MS (APCI) 329.0 ((M−2×oxalic acid)+H)⁺

¹H NMR (DMSO-d₆) 8.49(1 H, s); 8.43(1 H, d); 7.74-7.68(3 H, m); 7.37(1 H, dd); 7.01 (2 H, d); 4.35(2 H, t); 3.94(2 H, dd); 3.81-3.76(1 H, m); 3.41(2 H, t); 2.87-2.64(2 H, m); 1.86-1.66(2 H, m).

EXAMPLE 76

(±)-1-(2,6-Dimethylbiphenyl-4-yloxy)-4-(3-pyridyl)-2-butanol

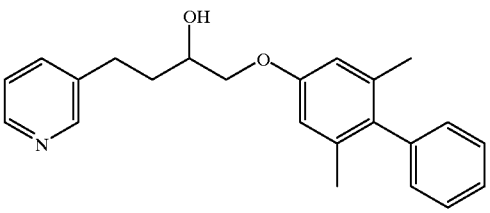

a) 2,6-Dimethylbiphenyl-4-ol

Prepared according to the method described in Example 33a) from 4-bromo-3,5-dimethylphenol (3.0 g), benzeneboronic acid (2.0 g), toluene (30 ml), ethanol (8 ml), aqueous sodium carbonate (2 M, 14 ml) and tetrakis (triphenylphosphine)palladium(0) (0.51 g) with heating at reflux for 6 hours. The residue obtained after work up was purified by column chromatography over silica with dichloromethane to give the sub-title compound as a solid (2.63 g).

m.p. 122–124° C.

MS (EI) 198 (M)+

¹H NMR (DMSO-d₆) 7.48-7.28(3 H, m); 7.12(2 H, dt); 6.59(2 H, s); 4.61(1 H, s); 1.98(6 H, s).

b) (±)-1-(2,6-Dimethylbiphenyl-4-yloxy)-4-(3-pyridyl)-2-butanol

Prepared according to the method described in Example 24b) from (±)-α-(chloromethyl)-3-pyridinepropanol (0.70 g), 2,6-dimethylbiphenyl-4-ol (0.79 g), ethanol (15 ml) and aqueous sodium hydroxide (1.9 M, 2.5 ml). After work up the residue was purified by column chromatography over silica with ethyl acetate to give the title compound as a solid (0.72 g).

m.p. 102–104° C.

MS (APCI) 348.3 (M+H)+

¹H NMR (DMSO) 8.47(1 H, d); 8.41(1 H, dd); 7.66(1 H, dt); 7.43(2 H, t); 7.38-7.30(2 H, m); 7.10(2 H, d); 6.69(2 H, s); 5.05(1 H, d); 3.93-3.85(2 H, m); 3.85-3.73(1 H, m); 2.88-2.63(2 H, m); 1.92(6 H, s); 1.98-1.85(2 H, m).

EXAMPLE 77

(±)-1-(4-Biphenyl)-5-(3-pyridyl)pent-1-yn-3-ol

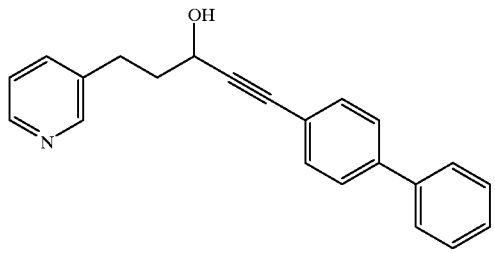

4-Bromobiphenyl (2.33 g), (±)-5-(3-pyridyl)pent-1-yn-3-ol (2.1 g, Example 55d), bis(triphenylphosphine)palladium (II) chloride (0.7 g) and copper(I) iodide (0.096 g) in diethylamine (40 ml) were stirred together for 4 hours at room temperature under nitrogen. The reaction was poured into water and extracted with ethyl acetate (3×100 ml). The organic solution was dried over anhydrous magnesium sulfate, filtered and concentrated under reduced pressure. The residue was purified by column chromatography over silica eluting dichloromethane:methanol (97:3) to give the title compound as a pale yellow solid (0.62 g).

m.p. 110–111° C.

MS (APCI) 314 (M+H)+

¹H NMR (CDCl₃) 8.53(1 H, d); 8.46(1 H, dd); 7.60-7.50(5 H, m); 7.50-7.40(4 H, m); 7.40-7.3(1 H, m); 7.30-7.20(1 H, m); 4.63(1 H, t); 2.90(2 H, t); 2.70(1 H, bs); 2.2-2.1(2 H, m).

EXAMPLE 78

(2S)-1-(3'-Chlorobiphenyl-4-ylthio)-4-(3-pyridyl)-2-butanol oxalic acid salt

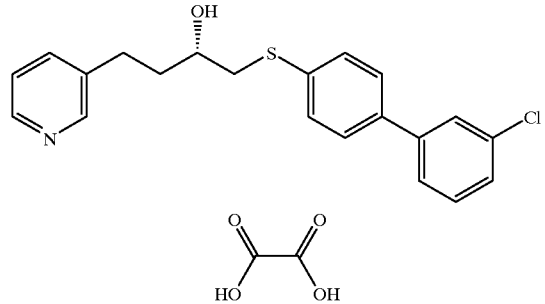

Prepared according to the method used for (2R)-1-(3'-chlorobiphenyl-4-ylthio)-4-(3-pyridyl)-2-butanol (Example 57).

Aqueous potassium hydroxide (4 M, 2 ml) was added to a solution of 3'-chlorobiphenyl-4-yl N,N-dimethyl-S-thiocarbamate (0.564 g) in ethanol (10 ml). The solution was heated at 100° C. under nitrogen for 16 hours. A solution of (2R)-2-(tert-butyldimethylsilyloxy)-4-(3-pyridyl)-1-butyl para-toluenesulfonate (0.767 g) in ethanol (10 ml) was then added and heating was continued for 5 hours. The colourless oil obtained after work-up was dissolved in tetrahydrofuran (20 ml). Tetrabutylammonium fluoride (0.61 g) was added and the resulting solution stirred at room temperature for 4 hours. The reaction mixture was poured into water and was then extracted with ethyl acetate. The organic extract was dried over anhydrous magnesium sulfate, filtered and concentrated under reduced pressure. The residue obtained was purified by column chromatography over silica eluting with ethyl acetate to give an oil. Conversion to the oxalate salt upon treatment with excess saturated ethereal oxalic gave the title compound as a white solid (0.135 g).

m.p. 120–121° C.

MS (APCI) 370/372 ((M–oxalic acid)+H)+

¹H NMR (DMSO-d₆) 8.45(1 H, s); 8.42(1 H, s); 7.70-7.65(1 H, m); 7.65-7.60(4 H, m); 7.48(1 H, t); 7.43-7.35(3 H, m); 7.35-7.30(1 H, m); 3.65-3.60(1 H, m) 3.05(2 H, d); 2.75-2.60(2 H, m) 1.90-1.85(1 H, m); 1.75-1.70(1 H, m).

EXAMPLE 79

N-Methyl 6-((2R)-2-hydroxy-4-(3-pyridyl)-1-butoxy)naphthalen-2-yloxyacetamide

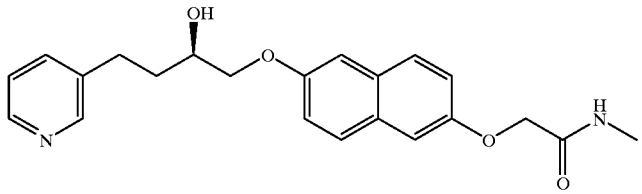

a) 6-Hydroxynaphthalen-2-yloxyacetic acid methyl ester

Prepared according to the method described in Example 20a) from 2,6-dihydroxynaphthalene (3.00 g), methyl bromoacetate (2.66 ml) and potassium carbonate (2.59 g) in acetone (30 ml), with heating at reflux for 18 hours. The crude product was purified by column chromatography over silica eluting with dichloromethane:ether (19:1) to give the sub-title compound as a solid (1.32 g).

m.p. 132–133° C.

MS (EI) 232 (M)+

$^1$H NMR (CDCl$_3$) 7.62(1 H, d); 7.59(1 H, d); 7.19(1 H, dd); 7.10-7.03(3 H, m); 5.01 (1 H, s); 4.73(2 H, s); 3.83(3 H, s).

b) 6-((2R)-2-Hydroxy-4-(3-pyridyl)-1-butoxy)naphthalen-2-yloxyacetic acid methyl ester Prepared according to the method described in example 26e) from (2R)-2-(tert-butyldimethylsilyloxy)-4-(3-pyridyl)-1-butyl para-toluenesulfonate (1.00 g), 6-Hydroxy-2-naphthyloxyacetic acid methyl ester, sodium hydride (60% dispersion in mineral oil, 0.11 g) in dimethylformamide (15 ml) with heating at 75° C. for 1 hour. The adduct was dissolved in tetrahydrofuran (10 ml) and tetrabutylammonium fluoride hydrate (1.5 g) was added. After 4 hours, the mixture was diluted with water and extracted with ether. The organic extracts were dried over anhydrous magnesium sulfate, filtered and concentrated under reduced pressure. The residue was purified by column chromatography over silica eluting with hexane:acetone (3:2 then 1:1) to give the sub-title compound as a solid (0.22 g).

MS (APCI) 382.3 (M+H)+

$^1$H NMR (CDCl$_3$) 8.53(1 H, s); 8.47(1 H, d); 7.66(1 H, d); 7.63(1 H, d); 7.58(1 H, d); 7.25-7.19(2 H, m); 7.14(1 H, dd); 7.07(2 H, dd); 4.73(2 H, s); 4.10-4.05(2 H, m); 3.96 (1 H, dd); 3.83(3 H, s); 3.0-2.75(2 H, m); 1.99-1.88(2 H, m).

c) N-Methyl 6-((2R)-2-hydroxy-4-(3-pyridyl)-1-butoxy)naphthalen-2-yloxyacetamide A solution of 6-((2R)-2-hydroxy-4-(3-pyridyl)-1-butoxy)naphthalen-2-yloxyacetic acid methyl ester (0.215 g) in methanol (10 ml) was saturated with methylamine gas. After 16 hours the crystalline product was collected by filtration and dried under vacuum to give the title compound as a solid (0.10 g).

m.p. 164–165° C.

MS (APCI) 381(M+H)+

$^1$H NMR (DMSO-d$_6$) 8.47(1 H, s); 8.40(1 H, d); 8.08(1 H, br); 7.74(1 H, d); 7.70(1 H, d); 7.67(1 H, d); 7.31(1 H, dd); 7.28-7.06(2 H, m); 7.22(1 H, dd); 7.14(1 H, dd); 5.08(1 H, d); 4.53(2 H, s); 3.97(2 H, d); 3.88-3.78(1 H, m); 2.90-2.63(2 H, m); 2.67(3 H, d); 1.97-1.82(1 H, m); 1.81-1.70(1 H, m).

EXAMPLE 80

(2R)-1-(3'-Carboxybiphenyl-4-yloxy)-4-(3-pyridyl)-2-butanol

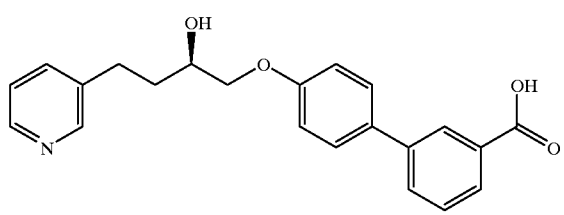

A stirred solution of (2R)-1-(3'-cyanobiphenyl-4-yloxy)-4-(3-pyridyl)-2-butanol (0.60 g) and sodium hydroxide (0.696 g) in ethanol (8 ml) and water (2 ml) was heated at reflux for 10 hours. The mixture was concentrated and the residues dissolved in water and neutralised. The precipitate was filtered off and dried under vacuum to give the title compound as a white solid (0.616 g).

m.p. 165–168° C.

MS (APCI) 364 (M+H)+

$^1$H NMR (DMSO) 8.46(1 H, d); 8.40(1 H, dt); 8.12(1 H, t); 7.88-7.80(2 H, m); 7.68-7.63(3 H, m); 7.54(1 H, t); 7.49-7.29(1 H, m); 7.04(2 H, d); 5.1(1 H, br); 3.94(2 H, d); 3.82-3.78(1 H, m); 3.33(1 H, br); 2.82-2.68(2 H, m); 1.88-1.73(2 H, m).

EXAMPLE 81

(±)-1-(3-Pyridyl)-5-(4-biphenyl)-3-pentanol

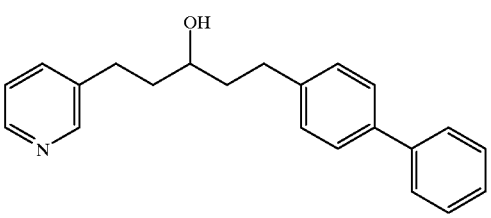

(±)-1-(4-Biphenyl)-ethynyl-3-pyridinepropanol (0.20 g, Example 77) was dissolved in ethanol (20 ml) to this was added a slurry of 10% palladium on charcoal (20 mg) in ethanol (1 ml). The mixture was hydrogenated at 1.5 atmospheres for 16 hours at room temperature. The product was filtered through Kieselguhr, the filtrate was concentrated and the residue triturated with hexane:ether (1:1) to give the title compound as a white solid (0.192 g).

m.p. 108–109° C.

MS (APCI) 318 (M+H)$^+$ $^1$H NMR (CDCl$_3$) 8.50(1 H, d); 8.45(1 H, dd); 7.60-7.50(5 H, m); 7.45-7.35(2 H, m); 7.30-7.25(2 H, m); 7.25-7.15(2 H, m); 3.75-3.65(1 H, m); 2.90-2.65(4 H, m); 1.90-1.75(4 H, m); 1.5(1 H, d).

EXAMPLE 82

(2R)-1-(3'-(Methoxycarbonyl)biphenyl-4-yloxy)-4-(3-pyridyl)-2-butanol oxalic acid salt

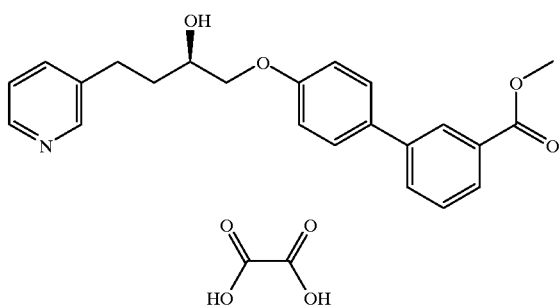

Concentrated sulfuric acid (2.5 ml) was added to a suspension of (2R)-1-(3'-carboxybiphenyl-4-yloxy)-4-(3-pyridyl)-2-butanol (0.5 g) in methanol (50 ml). The mixture was heated at reflux for 10 hours. The mixture was cooled to room temperature and made basic by addition of aqueous sodium hydrogen carbonate. The mixture was extracted with ethyl acetate, dried over anhydrous magnesium sulfate, filtered and concentrated under reduced pressure. The residue was purified by column chromatography over silica eluting with dichloromethane:methanol (19:1) to give an oil which was converted to the oxalate salt upon treatment with oxalic acid (excess) in ether to give the title compound as a solid (0.482 g).

m.p. 102–103° C.

MS (APCI) 378 ((M−oxalic acid)+H)$^+$ $^1$H NMR (DMSO-d$_6$) 8.49(1 H, d); 8.42(1 H, dd); 8.13(1 H, s); 7.90(2 H, d); 7.71(1 H, d); 7.65-7.55(3 H, m); 7.35(1 H, q); 7.05(2 H, d); 3.95(2 H, d); 3.90(3 H, s); 3.85-3.75(1 H, m); 2.90-2.65(2 H, m); 1.95-1.65(2 H, m).

EXAMPLE 83

(2R)-4-(3-Pyridyl)-1-(6-(3,3,3-Trifluoropropoxy)naphthalen-2-yloxy)-2-butanol

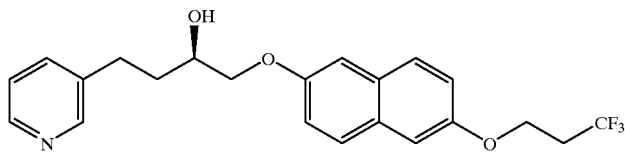

a) 2-Hydroxy-6-(3,3,3-trifluoropropoxy)naphthalene

Potassium hydroxide (1.16 g) was added to a stirred suspension of 2,6-dihydroxynaphthalene (3.00 g) in water (90 ml) under nitrogen. After 30 minutes, 3-bromo-1,1,1-trifluoropropane (3.64 g) was added. After a further 5 hours, 3-iodo-1,1,1-trifluoropropane (1.00 g) was added. The mixture was stirred at 60° C. for 16 hours then cooled to 20° C., acidified by addition of hydrochloric acid (2 M) and extracted with ethyl acetate. The organic extracts were dried over anhydrous magnesium sulfate, filtered and concentrated under reduced pressure. The residue was purified by column chromatography over silica eluting with dichloromethane to give the sub-title compound as a solid (0.333 g).

m.p. 120–121° C.

MS (APCI) 255.3 (M−H)$^-$ $^1$H NMR (CDCl$_3$) 7.64(1 H, d); 7.60(1 H, d); 7.14-7.05(4 H, m); 4.84(1 H, s); 4.29(2 H, t); 2.76-2.60(2 H, d).

b) (2R)-4-(3-Pyridyl)-1-(6-(3,3,3-trifluoropropoxy)naphthalen-2-yloxy)-2-butanol Prepared according to the method described in example 26e) from 2-hydroxy-6-(3,3,3-trifluoropropoxy)naphthalene (0.212 g), (2R)-2-(tert-butyldimethylsilyloxy)-4-(3-pyridyl)-1-butyl para-toluenesulfonate (0.30 g) and sodium hydride (60%, 33 mg) in dimethylformamide (3 ml) with heating at 60° C. for 2 hours. The adduct was dissolved in tetrahydrofuran (10 ml) and tetrabutylammonium fluoride hydrate (0.30 g) was added. After 2 hours, the mixture was diluted with water and extracted with ether. The organic extracts were dried over anhydrous magnesium sulfate, filtered and concentrated under reduced pressure. The residue was purified by column chromatography over silica eluting with hexane:acetone (3:2) to give the title compound (0.18 g) which was recrystallised from ethyl acetate:hexane.

m.p. 120–121° C.

MS (APCI) 406.2 (M+H)$^+$ $^1$H NMR (CDCl$_3$) 8.54(1 H, s); 8.47(1 H. d); 7.67-7.62(2 H, m); 7.58(1 H, d); 7.23(1 H, dd); 7.16-7.10(4 H, m); 4.29(2 H, t); 4.17-4.06(2 H, m); 3.97(1 H, dd); 3.00-2.60(4 H, m); 2.48(1 H, br); 2.03-1.85(2 H, m).

EXAMPLE 84

(2R)-1-(4-(2-(Phenyl)ethynyl)phenoxy)-4-(3-pyridyl)-2-butanol

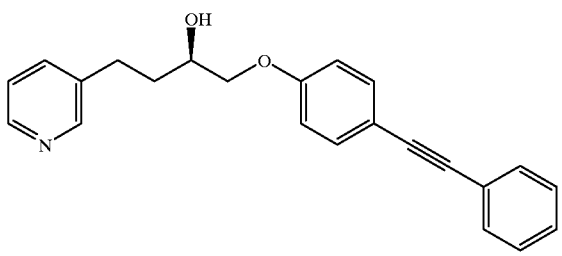

Copper (I) iodide (0.03 g) was added to a mixture of (2R)-1-(4-bromophenoxy)-4-(3-pyridyl)-2-butanol (1.05 g, Example 40a), phenylacetylene (0.33 g) and bis(triphenylphosphine)palladium(II) chloride (0.23 g) in triethylamine (10 ml), and the reaction mixture heated to 90° C. with stirring under nitrogen for 4 hours. The reaction mixture was allowed to cool to room temperature and then poured into water (150 ml). The product was extracted with ethyl acetate which was washed with brine and dried over anhydrous magnesium sulfate. The solution was concentrated under reduced pressure and the residue purified by column chromatography over silica eluting with dichloromethane:methanol (19:1) to give the title compound as a white solid (0.040 g).

m.p. 67–68° C.

MS (APCI) 344 (M+H)+

$^1$H NMR (DMSO-$d_6$) 8.46(1 H, d); 8.40(1 H, dd); 7.65(1 H, d); 7.58-7.35(7 H, m); 7.32-7.28(1 H, m); 6.98(2 H, d); 5.07(1 H, d); 3.93(2 H, d); 3.81-3.72(1 H, m); 2.84-2.63(2 H, m); 1.90-1.70(2 H, m).

EXAMPLE 85

(±)-(1E)-1-(4-Biphenyl)-5-(3-pyridyl)pent-1-en-3-ol

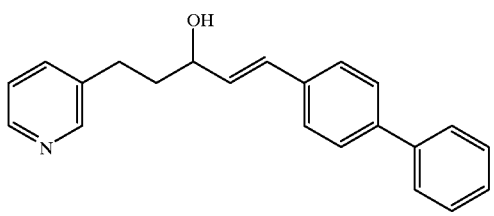

A solution of sodium bis(2-methoxyethoxy)aluminium hydride (65% in toluene, 0.822 ml) was added to dry tetrahydrofuran (5 ml) and cooled to 0° C. under nitrogen. A solution of (±)-1-(4-biphenyl)-5-(3-pyridyl)pent-1-yn-3-ol (0.27 g) in tetrahydrofuran (5 ml) was then added. Once addition was complete the mixture was stirred at room temperature for 4 hours. A solution of hydrochloric acid (2 M, 5 ml) was then added with stirring and the mixture was then made basic by addition of aqueous sodium hydrogen carbonate. The mixture was then extracted with ethyl acetate, dried over anhydrous magnesium sulfate, filtered and concentrated under reduced pressure. The residue was purified by column chromatography over silica eluting with ethyl acetate to give the title compound as a white solid (0.113 g).

m.p. 126–127° C.

MS (APCI) 316 (M+H)+

$^1$H NMR (CDCl$_3$) 8.55(1 H, d); 8.45(1 H, dd); 7.65-7.55(5 H, m); 7.45(4 H, t); 7.4-7.35(1 H, m); 7.25-7.20(1 H, m); 6.65(1 H, d, J=19 Hz); 6.30(1 H, dd, J=19 Hz); 4.40-4.30(1 H, m); 2.85-2.75(2 H, m); 2.05-1.90(2 H, m); 1.95(1 H, d).

EXAMPLE 86

(3S)-1-(3'-Chlorobiphenyl-4-yl)-5-(3-pyridyl)-3-pentanol oxalic acid salt

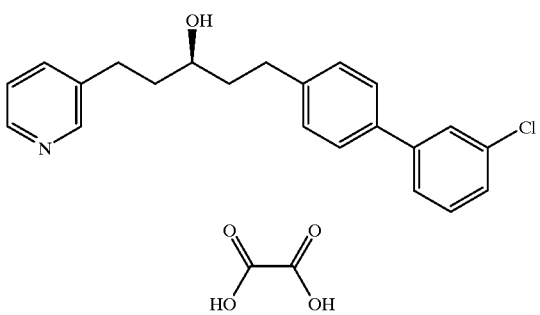

a) (2R)-1-(tert-Butyldimethylsilyloxy)-4-(3-pyridyl)-2-butanol

Solid tert-butyldimethylsilyl chloride (1.39 g) was added to a stirred solution of (2R)-4-(3-pyridyl)butane-1,2-diol (1.40 g, Example 34c), triethylamine (1.5 ml) and 4-dimethylaminopyridine (0.041 g) in dichloromethane (30 ml). The resulting solution was stirred at room temperature for 20 hours and then concentrated under reduced pressure. The residue was purified by column chromatography over silica eluting with ethyl acetate to give the sub-title compound as an oil (1.97 g).

MS (APCI) 382.6 (M+H)+

$^1$H NMR (CDCl$_3$) 8.48(1 H, s); 8.43(1 H, d); 7.53(1 H, dt); 7.20(1 H, dd); 3.66-3.62(2 H, m); 3.46-3.43(1 H, t); 2.87-2.82(1 H, m); 2.73-2.68(1 H, m); 2.49(1 H, d); 1.76-1.69(2 H, m); 0.9(9 H, s); 0.07(6 H, s).

b) (2R)-2-(Benzoyloxy)-4-(3-pyridyl)-1-butanol

Solid 1-(3-dimethylaminopropyl)-3-ethylcarbodiimide hydrochloride (2.01 g) was added to a stirring solution of (2R)-1-(tert-butyldimethylsilyloxy)-4-(3-pyridyl)-2-butanol (1.97 g), benzoic acid (1.28 g) and 4-dimethylaminopyridine (0.85 g) in dichloromethane (50 ml) and the resulting solution stirred at room temperature for 20 hours. The solution was then concentrated under reduced pressure and the residue dissolved in acetonitrile (30 ml). Aqueous hydrofluoric acid (40%, 3 ml) was added and the mixture stirred for 30 minutes before being poured into saturated aqueous sodium bicarbonate solution (200 ml). The mixture was extracted with ethyl acetate, the combined extracts dried over anhydrous magnesium sulfate, filtered and concentrated under reduced pressure. The residue was purified by column chromatography over silica eluting with ethyl acetate to give the sub-title compound as a solid (1.8 g).

MS (APCI) 272.3 (M+H)+

$^1$H NMR (CDCl$_3$) 8.46(1 H, s); 8.44(1 H, d); 8.05(2 H, d); 7.6(1 H, t); 7.53-7.45(3 H, m); 7.21-7.18(1 H, m); 5.22-5.18(1 H, m); 3.86-3.83(2 H, m); 2.79-2.73(2 H, m); 2.16-2.05(3 H, m);

c) (3R,1E/Z)-1-(4-Bromophenyl)-5-(3-pyridyl)pent-1-en-3-yl benzoate

Oxalyl chloride (0.18 ml) was added to a solution of dimethyl sulfoxide (0.21 ml) in dichloromethane (10 ml) at −65° C. and the resulting mixture stirred for 15 minutes. A solution of (2R)-2-(benzoyloxy)-4-(3-pyridyl)-1-butanol (0.5 g) in dichloromethane (2 ml) was then added and the resulting mixture stirred for 30 minutes. Triethylamine (1.4 ml) was added and the reaction allowed to warm, slowly to 0° C. over 1 hour. The reaction was diluted with ether (30 ml) and the mixture filtered and concentrated under reduced pressure. The residue was dissolved in tetrahydrofuran (2 ml) and was then added to a suspension of (4-bromophenyl) triphenylphosphorane [generated in situ from 4-bromobenzyltriphenylphosphonium bromide (1.02 g), diisopropylamine (0.31 ml) and n-butyllithium (2.5 M in hexanes, 0.8 ml)] in tetrahydrofuran (10 ml) at −65° C. The reaction was allowed to slowly warm to room temperature over 4 hours. The mixture was then poured into water (100 ml) and extracted with ether (3×30 ml), the combined extracts dried over anhydrous magnesium sulfate, filtered and concentrated under reduced pressure. The residue was purified by column chromatography over silica eluting with ether:isohexane (1:1) then with ether to give the sub-title compound as a yellow oil as a mixture of isomers (0.41 g).

MS (APCI) 422, 424 (M+H)$^+$ $^1$H NMR (CDCl$_3$, major Z isomer) 8.45(1 H, s); 8.43(1 H, d); 8.04(2 H, d); 7.56-7.54(1 H, m); 7.48-7.39(5 H, m); 7.18-7.14(3 H, m); 6.56(1 H, d); 5.98-5.89(1 H, m); 5.77(1 H, dd); 2.70(2 H, t); 2.27-2.2(1 H, m); 2.06-1.96(1 H, m).

d) (3S)-1-(4-Bromophenyl)-5-(3-pyridyl)-3-pentanol

A suspension of (3R,1E/Z)-1-(4-bromophenyl)-5-(3-pyridyl)pent-1-en-3-yl benzoate (0.78 g) and platinum on carbon (5%, 0.05 g) in ethanol (20 ml) and acetic acid (2 ml) was hydrogenated at 5 atmospheres pressure for 24 hours. The mixture was then filtered and concentrated under reduced pressure. The residue was dissolved in methanol (16 ml) and water (4 ml) and solid sodium hydroxide (0.4 g) were added. The mixture was stirred for 3 hours and then concentrated under reduced pressure. Water was added and the mixture extracted with ethyl acetate. The combined extracts were dried over anhydrous magnesium sulfate, filtered and concentrated under reduced pressure. The residue was purified by column chromatography over silica eluting with ethyl acetate to give the sub-title compound as an oil (0.21 g).

MS (APCI) 320, 322 (M+H)$^+$ $^1$H NMR (CDCl$_3$) 8.46(1 H, s); 8.44(1 H, d); 7.48(1 H, dt); 7.4(2 H, d); 7.22-7.19(1 H, m); 7.05(2 H, d); 3.66-3.6(1 H, m); 2.80-2.65(4 H, m); 1.81-1.75(4 H, m); 1.49(1 H, bs).

e) (3S)-1-(3'-Chlorobiphenyl-4-yl)-5-(3-pyridyl)-3-pentanol oxalic acid salt

Prepared according to the method described in Example 33a) from toluene (5 ml), water (1 ml), (3S)-1-(4-bromophenyl)-5-(3-pyridyl)-3-pentanol (0.09 g), sodium carbonate (0.172 g), 3-chlorobenzeneboronic acid (0.05 g), ethanol (1 ml) and tetrakis(triphenylphosphine)palladium(0) (9 mg) with heating at 100° C. for 45 minutes. After work up the residue was purified by column chromatography over silica eluting with ethyl acetate to give an oil which was converted to the oxalate salt upon treatment with oxalic acid (excess) in ether to give the title compound as a solid (0.057 g).

m.p. 103–104° C.

MS (APCI) 352/354 ((M−oxalic acid)+H)$^+$ $^1$H NMR (DMSO-d$_6$) 8.45(1 H, s); 8.40(1 H, d); 7.70-7.54(5 H, m); 7.50(1 H, t); 7.41(1 H, dt); 7.38-7.34(1 H, m); 7.30(2 H, d); 3.45-2.85(1 H, m); 2.83-2.62(2 H, m); 2.64-2.58(2 H, m); 1.75-1.57(4 H, m).

EXAMPLE 87

(±)-1-(4-(Phenylmethoxy)phenoxy)-4-(3-pyridyl)-2-butanol

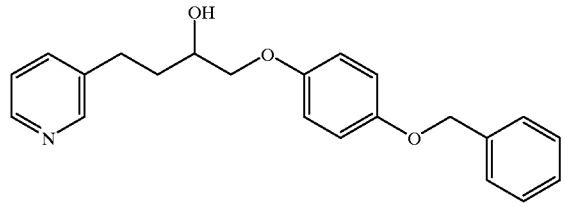

Prepared according to the method described in Example 24b) from 4-(benzyloxy)phenol (1.00 g), (±)-α-(chloromethyl)-3-pyridinepropanol (0.50 g) and sodium hydroxide (0.23 g) in ethanol (20 ml) and water (5 ml) with heating at reflux for 45 minutes. After work up the residue was purified by column chromatography over silica eluting with dichloromethane:ethanol (19:1) and then using a fresh column of silica eluting with ethyl acetate to give the title compound as a solid (0.58 g). Recrystallisation from ethyl acetate:hexane gave colourless crystals.

m.p. 79–82° C.

MS (APCI) 350.1 (M+H)$^+$ $^1$H NMR (DMSO-d$_6$) 8.44(1 H, d); 8.39(1 H, dd); 7.64(1 H, dt); 7.45-7.27(6 H, m); 6.95-6.82(4 H, m); 5.03(2 H, s); 4.99(1 H, d); 3.85-2.67(3 H, m); 2.85-2.60(2 H, m); 2.90-2.75(1 H, m); 2.75-2.60(1 H, m).

EXAMPLE 88

(±)-1-(3,4-Dimethoxyphenoxy)-4-(3-pyridyl)-2-butanol

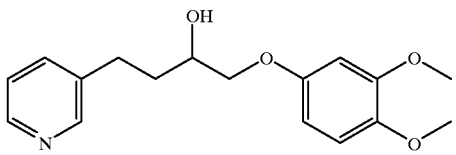

Prepared according to the method described in Example 24b) from 3,4-dimethoxyphenol (0.77 g), (±)-α-(chloromethyl)-3-pyridinepropanol (1.0 g) and sodium hydroxide (0.2 g) in ethanol (45 ml) and water (5 ml) with heating at reflux for 1 hour. After work up the residue was purified by column chromatography over silica eluting with hexane:acetone (2:1) to give the title compound as a colourless oil (0.10 g).

MS (APCI) 304 (M+H)$^+$ $^1$H NMR (DMSO-d$_6$) 8.44(1 H, d); 8.39(1 H, dd); 7.64(1 H, dt); 7.32-7.27(1 H, m); 6.81(1 H, d); 6.54(1 H, d); 6.40(1 H, dd); 4.98(1 H, d); 3.82-3.68(9 H, m); 2.85-2.60(2 H, m); 1.90-1.62(2 H, m).

EXAMPLE 89

(±)-1-(3-Acetylbiphenyl-4-yloxy)-4-(3-pyridyl)-2-butanol

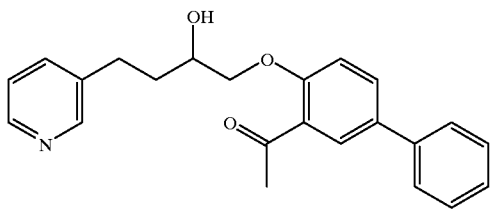

a) (±)-1-(2-Acetyl-4-bromophenoxy)-4-(3-pyridyl)-2-butanol

Prepared according to the method described in Example 24b) from 2-hydroxy-5-bromoacetophenone (1.1 g), ethanol (25 ml), sodium hydroxide (0.2 g), water (5 ml) and (±)-α-(chloromethyl)-3-pyridinepropanol (0.48 g; Example 24a) to give a yellow oil. This was purified by column chromatography over silica eluting with dichloromethane:ethanol (95:5) to give the sub-title compound as a pale oil (0.13 g).

MS (APCI) 366 (M+H)+
$^1$H NMR (CDCl$_3$) 8.47(1 H, d); 8.43(1 H, dd); 7.78(1 H, d), 7.57-7.51(2 H, m); 7.51-7.23(1 H, m); 6.84(1 H, d); 4.10-3.94(4 H, m); 2.95-2.75(2 H, m); 2.57(3 H, s); 1.95-1.80(2 H, m).

b) (±)-1-(3-Acetylbiphenyl-4-yloxy)-4-(3-pyridyl)-2-butanol

Prepared according to the method described in Example 33a) from toluene (7.5 ml), (±)-1-(2-acetyl-4-bromophenoxy)-4-(3-pyridyl)-2-butanol (0.134 g), benzeneboronic acid (0.07 g), aqueous sodium carbonate (2 M, 1 ml), ethanol (2.5 ml) and tetrakis(triphenylphosphine) palladium(0) (0.02 g) with heating at reflux for 3 hours. After work up the residue was purified by column chromatography over silica eluting with ethanol:dichloromethane (5:95) to give the title compound as an oil (0.070 g).

MS (APCI) 362 (M+H)+
$^1$H NMR (CDCl$_3$) 8.50(1 H, d); 8.45(1 H, dd); 7.91(1 H, d); 7.66(1 H, dd); 7.58-7.50(3 H, m); 7.50-7.40(2 H, m); 7.40-7.25(1 H, m); 7.25-7.20(1 H, m); 7.02(1 H, d); 4.20-3.95(3 H, m); 3.55(1 H, bs); 3.0-2.7(2 H, m); 2.64(3 H, s); 2.0-1.8(2 H, m).

EXAMPLE 90

(2R)-1-(2'-Fluorobiphenyl-4-yloxy)-4-(3-pyridyl)-2-butanol

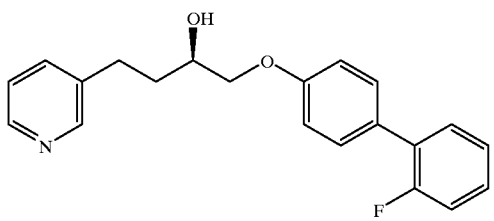

Prepared according to the method described in Example 33a) from toluene (5 ml), (2R)-1-(4-bromophenoxy)-5-(3-pyridyl)-2-butanol (0.250 g), aqueous sodium carbonate (2 M, 1 ml), 2-fluorobenzeneboronic acid (*Journal of Organic Chemistry* 1995, 60, 3020) (0.216 g), ethanol (1 ml) and tetrakis(triphenylphosphine)palladium(0) (0.060 g) with heating at 100° C. for 4 hours. After work up the residue was purified by column chromatography over silica eluting with hexane:acetone (3:2) to give the title compound as a colourless oil (0.100 g).

MS (APCI) 338 (M+H)+
$^1$H NMR (CDCl$_3$) 8.53(1 H, d); 8.47(1 H, dd); 7.60-7.55(1 H, m); 7.49(2 H, t); 7.41(1 H, dt); 7.30-7.25(1 H, m); 7.30-7.10(3 H, m); 6.98(2 H, dd); 4.10-4.00(2 H, m); 3.90(1 H, dd); 3.00-2.90(1 H, m); 2.85-2.75(1 H, m); 2.41(1 H, d); 2.10-1.80(2 H, m).

EXAMPLE 91

(2R)-1-(2',4',6'-Trimethylbiphenyl-4-yloxy)-4-(3-pyridyl)-2-butanol

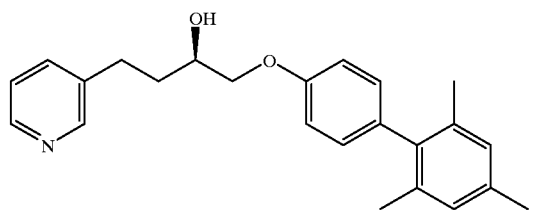

Prepared according to the method described in Example 33a) from toluene (5 ml), (2R)-1-(4-bromophenoxy)-5-(3-pyridyl)-2-butanol (0.25 g), aqueous sodium carbonate (2 M, 1 ml), 2,4,6-benzeneboronic acid (0.267 g), ethanol (1 ml) and tetrakis(triphenylphosphine)palladium(0) (0.060 g) with heating at 100° C. for 8 hours. After work up the residue was purified by column chromatography over silica eluting with hexane:acetone (3:2) to give the title compound as a colourless oil (0.150 g).

MS (APCI) 362 (M+H)+
$^1$H NMR (CDCl$_3$) 8.53(1 H, d); 8.47(1 H, dd); 7.60-7.55(1 H, m); 7.25-7.20(1 H, m); 7.05(2 H, d); 6.96(2 H, d); 6.93(2 H, s); 4.10-4.00(2 H, m); 3.95(1 H, dd); 3.00-2.90(1 H, m); 2.85-2.75(1 H, m); 2.45(1 H, d); 2.32(3 H, s); 2.00(6 H, s); 1.95-1.85(2 H, m).

EXAMPLE 92

(±)-1-(Biphenyl-2-yloxy)-4-(3-pyridyl)-2-butanol

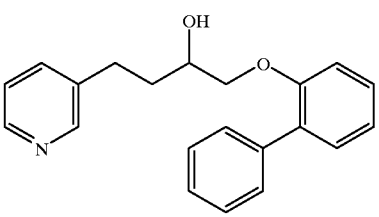

Prepared according to the method described in Example 24b) from (±)-α-(chloromethyl)-3-pyridinepropanol (1.0 g, Example 24a), 2-phenylphenol (0.92 g), ethanol (45 ml) and aqueous sodium hydroxide (1.0 M, 5 ml) with heating at reflux for 1 hour. After work up the residue was purified by column chromatography over silica eluting with hexane:acetone (2:1) to give the title compound as a colourless oil (0.60 g).

MS (APCI) 320 (M+H)+
$^1$H NMR (DMSO-d$_6$) 8.38(2 H, dd); 7.53-7.50(3 H, m); 7.40-7.26(6 H, m); 7.10(1 H, d); 7.00(1 H, t); 4.94(1 H, d);

3.99-3.94(1 H, m); 3.89-3.86(1 H, m); 3.72-3.62(1 H, m); 2.75-2.60(2 H, m); 2.85-2.55(2 H, m).

EXAMPLE 93

(2R)-1-(3'-(Benzyloxy)biphenyl-4-yloxy)-4-(3-pyridyl)-2-butanol

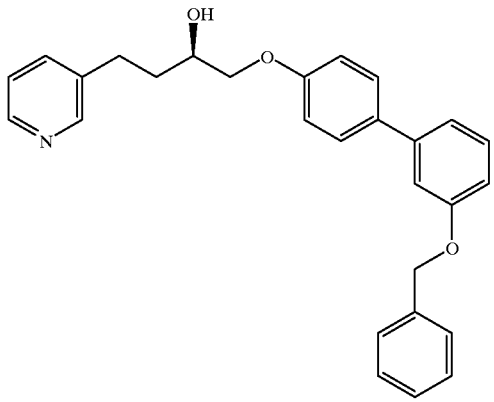

a) 3-(Benzyloxy)bromobenzene

Potassium carbonate (1.4 g) was added to a solution of 3-bromophenol (2 g) in acetone (20 ml) and the mixture was stirred under nitrogen at room temperature. Benzyl bromide was added and stirring continued at room temperature for 18 hours, then at reflux for 1 hour. The reaction mixture was allowed to cool and was then concentrated under reduced pressure. The residue was then partitioned between water and dichloromethane. The organic solution was then washed with brine and dried over anhydrous magnesium sulfate, filtered and concentrated under reduced pressure. The residue was purified by column chromatography over silica eluting with hexane to give the sub-title compound as a white crystalline solid (2.6 g).

m.p. 61–63° C.

GCMS (ESI) 263/264 (M)$^+$ $^1$H NMR (DMSO-d$_6$) 7.46-7.32(5 H, m); 7.28-7.23(2 H, m); 7.13(1 H, dt); 7.03(1 H, dq); 5.13(2 H, s).

b) 3-(Benzyloxy)benzeneboronic acid

Prepared according to the method described in Example 51b) from 3-(benzyloxy)bromobenzene (2.16 g, Example 93a), n-butyllithium (2.5 M in hexanes, 3.6 ml) and triisopropyl borate (3.4 g), in tetrahydrofuran (2×10 ml). After work up the residue was purified by column chromatography over silica eluting with ethyl acetate:hexane:acetic acid (20:79.5:0.5) then methanol to give the sub-title compound as a white solid (1.04 g). This was used without analysis.

c) (2R)-1-(3'-(Benzyloxy)biphenyl-4-yloxy)-4-(3-pyridyl)-2-butanol

Prepared according to the method described in Example 33a) from (2R)-1-(4-bromophenoxy)-4-(3-pyridyl)-2-butanol (0.97 g, Example 40a), 3-(benzyloxy)benzeneboronic acid (1.0 g, Example 93b), tetrakis(triphenylphosphine)palladium(0) (0.09 g), toluene (7.5 ml), ethanol (2 ml) and aqueous sodium carbonate (2 M, 3.5 ml) with heating at 120° C. for 2 hours 30 minutes. After work up the residue was purified by column chromatography over silica eluting with methanol:dichloromethane (5:95) to give the title compound as a white solid (1.07 g).

m.p. 83–84° C.

MS (APCI) 426 (M+H)$^+$ $^1$H NMR (DMSO-d$_6$) 8.46(1 H, d); 8.40(1 H, dd); 7.65(1 H, dt); 7.59(2 H, dd); 7.49-7.47(2 H, m); 7.40(2 H, dd); 7.35-7.30(3 H, m); 7.22(1 H, t); 7.18(1 H, d); 7.01(2 H, d); 6.95(1 H, dd); 5.18(2 H, s); 5.07(1 H, d); 3.93(2 H, d); 3.83-3.72(1 H, m); 2.85-2.62(2 H, m); 1.85-1.68(2 H, m).

EXAMPLE 94

(3R)-1-(3'-Chlorobiphenyl-4-yl)-5-(3-pyridyl)-3-pentanol oxalic acid salt

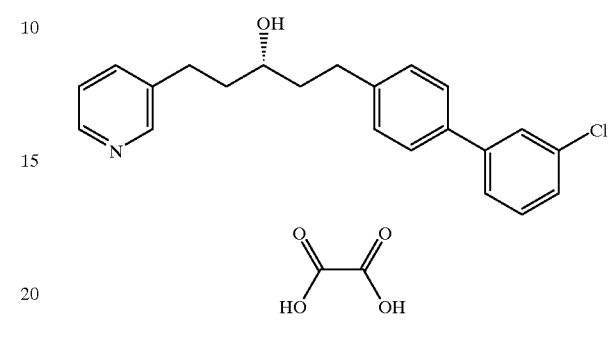

Prepared according to the method described in Example 27 from (3S)-1-(3'-chlorobiphenyl-4-yl)-5-(3-pyridyl)-3-pentanol (0.137 g, Example 86), benzoic acid (0.061 g), triphenylphosphine (0.131 g) and diethyl azodicarboxylate (0.061 ml). The mixture was concentrated under reduced pressure and the residue redissolved in methanol (8 ml) and water (2 ml). Solid sodium hydroxide (0.2 g) was added and the reaction stirred for 2 hours before being poured into a solution of saturated aqueous sodium hydrogen carbonate. The mixture was extracted with ethyl acetate, the combined organic extracts dried over anhydrous magnesium sulfate, filtered and concentrated under reduced pressure to give an oil which was converted to the oxalate salt upon treatment with oxalic acid in ether (excess) to give the title compound as a solid (0.033 g).

m.p. 104–105° C.

MS (APCI) 352/354 ((M−oxalic acid)+H)$^+$ $^1$H NMR (DMSO-d$_6$) 8.45(1 H, s); 8.40(1 H, d); 7.70-54(5 H, m); 7.50(1 H, t); 7.41(1 H, dt); 7.38-7.34(1 H, m); 7.30(2 H, d); 3.45-2.85(1 H, m); 2.83-2.62(2 H, m); 2.64-2.58(2 H, m); 1.75-1.57(4 H, m).

EXAMPLE 95

(±)-1-(3-Cyclopentyloxy-4-methoxyphenoxy)-4-(3-pyridyl)-2-butanol oxalic acid salt

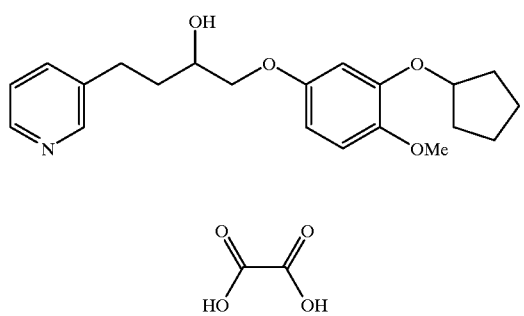

a) 3-Cyclopentlyoxy-4-methoxyphenol

Solid meta-chloroperoxybenzoic acid (50–55% by wt., 4.1 g) was added in one portion to a cooled (ice bath) solution of 3-cyclopentyloxy-4-methoxybenzaldehyde (2.09 g) in dichloromethane (25 ml). The reaction was then stirred at room temperature under nitrogen for 4 hours. Aqueous sodium thiosulfate (10%, 25 ml) was added and the mixture stirred for 20 minutes. Saturated aqueous sodium hydrogen carbonate (25 ml) was carefully added in order to make the solution basic (pH=9). The aqueous layer was extracted with dichloromethane, the combined extracts dried over anhydrous magnesium sulfate, filtered and concentrated under reduced pressure. The residue was purified by column chromatography over silica eluting with petroleum ether (b.p. 40–60° C.):ethyl acetate (4:1) to give the sub-title compound as a white solid (1.70 g).

MS (EI) 208 (M)$^+$ $^1$H NMR (DMSO-d$_6$) 8.49(1 H, s); 6.96(1 H, d); 6.83(1 H, d); 6.71(1 H, dd); 4.79-4.74(1 H, m); 3.74(3 H, s); 1.91-1.73(2 H, m); 1.73-1.56(6 H, m).

b) (±)-1-(3-Cyclopentyloxy-4-methoxyphenoxy)-4-(3-pyridyl)-2-butanol oxalic acid salt Prepared according to the method described in Example 24b) from 3-cyclopentyloxy-4-methoxyphenol (0.835 g), ethanol (10 ml), aqueous sodium hydroxide (2 M, 2.5 ml) and (±)-α-(chloromethyl)-3-pyridinepropanol (0.760 g, Example 24a) to give the title compound as a yellow oil. This was purified by column chromatography over silica eluting with dichloromethane:ethanol and further purified by preparative normal-phase HPLC on a Dynamax™ Silica column with dichloromethane:ethanol (19:1). The purified material was then converted to the oxalate salt by treatment with excess oxalic acid in diethyl ether to give the title compound as a white solid (0.197 g).

m.p. 68–71° C.

MS (APCI) 358 ((M–oxalic acid)+H)$^+$ $^1$H NMR (CDCl$_3$) 8.47(1 H, bs); 8.41(1 H, d); 7.69(1 H, dt); 7.34(1 H, dd); 6.82(1 H, d); 6.49(1 H, d); 6.40(1 H, dd); 4.77-4.73(1 H, m); 3.80-3.71(3 H, m); 3.66(3 H, s); 2.80-2.65(2 H, m); 1.89-1.56(10 H, m)

EXAMPLE 96

(2R)-1-(3-Chlorobiphenyl-4-yloxy)-4-(3-pyridyl)-2-butanol oxalic acid salt

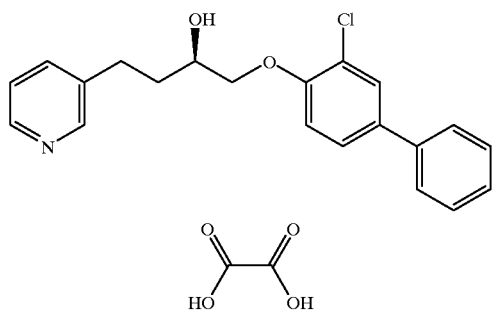

Solid 3-chlorobiphenyl-4-ol (0.206 g, ex SALOR) was added to a solution of sodium hydride (60% dispersion in mineral oil, 0.045 g) in dimethylformamide (3 ml). After stirring at room temperature for 15 minutes a solution of (2S)-2-(tert-butyldimethylsilyloxy)-4-(3-pyridyl)-1-butyl para-toluenesulfonate (0.435 g, Example 26d) in dimethylformamide (2 ml) was added and the reaction stirred at 60° C. for 3 hours. After cooling the is reaction was poured into water and extracted with ethyl acetate. The combined organic extracts were concentrated under reduced pressure and then redissolved in tetrahydrofuran (25 ml). Solid tetrabutylammonium fluoride (0.30 g) was added and the mixture stirred overnight. The reaction mixture was then concentrated under reduced pressure and the residue purified by column chromatography over silica eluting with dichloromethane then ethyl acetate to give a gum (0.13 g). The purified material was then converted to the oxalate salt by treatment with excess oxalic acid in diethyl ether to give the title compound as a white solid (0.060 g).

MS (APCI) 354 ((M–oxalic acid)+H)$^+$ $^1$H NMR (DMSO-d$_6$) 8.49(1 H, s); 8.42(1 H, d); 7.75-7.55(5 H, m); 7.50-7.40(2 H, m); 7.38-7.30(2 H, m); 7.23(1 H, d); 4.10-3.98(2 H, m); 3.85-2.78(1 H, m); 2.90-2.65(2 H, m); 2.0-1.7(2 H, m).

EXAMPLE 97

(±)-1-(Biphenyl-4-yloxy)-5-(3-pyridyl)-3-pentanol

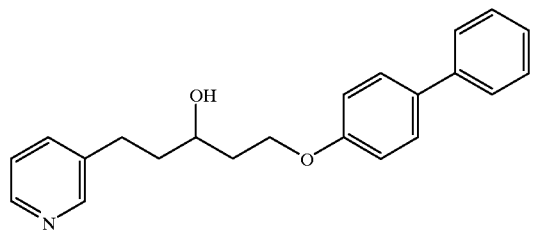

a) (±)-6-(3-Pyridyl)hex-1-en-4-ol

A solution of allyl magnesium bromide (1 M in ether, 17.75 ml) was added to a stirred solution of 3-(3-pyridyl)-1-propionaldehyde (2.00 g) in anhydrous tetrahydrofuran (50 ml) at 0° C. under nitrogen. After 30 minutes, saturated aqueous sodium bicarbonate solution was added and the mixture extracted with ethyl acetate. The combined organic extracts were dried over anhydrous magnesium sulfate, filtered and concentrated under reduced pressure. The residue was purified by column chromatography over silica eluting with dichloromethane:acetone (3:1) to give the sub-title compound as an oil (1.385 g).

MS (APCI) 178.3 (M+H)$^+$ $^1$H NMR (CDCl$_3$) 8.48(1 H, d); 8.44(1 H, dd); 7.53(1 H, d); 7.21(1 H, dd); 5.90-5.74 (1 H, m); 5.18-5.13(2 H, m); 3.72-3.63(1 H, m); 2.89-2.63(2 H, m); 2.39-2.29(1 H, m); 2.25-2.14(1 H, m); 1.82-1.74(2 H, m).

b) (±)-5-(3-Pyridyl)-1,3-pentanediol

A mixture of ozone in air was passed through a solution of (±)-6-(3-pyridyl)-hex-1-en-4-ol (1.38 g) in methanol (70 ml) at 0° C. for 2 hours. The solution was flushed with nitrogen for 1 hour then sodium borohydride (2 g) was added portionwise. The mixture was stirred at room temperature for 20 hours and then concentrated under reduced pressure. The residue was purified by column chromatography over silica eluting with methanol:dichloromethane (1:19) and the required fractions concentrated under reduced pressure. Ethyl acetate (25 ml) and aqueous potassium tartrate solution (1 M, 25 ml) were added to the residue and the mixture stirred rapidly for 2 hours. The phases were separated and the aqueous phase extracted with ethyl acetate (10×25 ml). The combined organic extracts were dried over anhydrous magnesium sulfate, filtered and concentrated under reduced pressure to give the sub-title compound as an oil (1.20 g).

MS (APCI) 182.2 (M+H)$^+$ $^1$H NMR (DMSO-d$_6$) 8.42(1 H, d); 8.38(1 H, dd); 7.61(1 H, d); 7.29(1 H, dd); 4.47(1 H, d); 4.32(1 H, t); 3.60-3.43(3 H, m); 2.78-2.56(2 H, m); 1.70-1.45(4 H, m).

c) (±)-3-Hydroxy-5-(3-pyridyl)-1-pentyl para-toluenesulfonate

Solid para-toluenesulfonyl chloride (1.26 g) was added to a solution of (±)-5-(3-pyridyl)-1,3-pentanediol (1.20 g) and triethylamine (1.11 ml) in anhydrous dichloromethane (20 ml) at −30° C. under nitrogen. The solution was allowed to warm to room temperature over 1 hour and stirring was continued for 24 hours. Methanol (1 ml) was added and the solution concentrated under reduced pressure. The residue was purified by column chromatography over silica eluting with hexane:acetone (3:2) to give the sub-title compound as an oil (1.05 g).

MS (APCI) 336.1 (M+H)$^+$ $^1$H NMR (DMSO-d$_6$) 8.40-8.37(2 H, m); 7.77(2 H, d); 7.58(1 H, d); 7.48(2 H, d); 7.29 (1 H, dd); 4.72(1 H, d); 4.15-4.07(2 H, m); 3.50-3.40(1 H, m); 3.71-3.62(1 H, m); 2.58-2.50(1 H, m); 2.42(3 H, s); 1.78-1.69(1 H, m); 1.63-1.53(3 H, m).

d) (±)-1-(Biphenyl-4-yloxy)-5-(3-pyridyl)-3-pentanol

Sodium hydride (60% dispersion in mineral oil, 0.045 g) was washed with hexane (1 ml) under nitrogen. A solution of 4-hydroxybiphenyl (0.190 g) in anhydrous dimethylformamide (3 ml) was then added and the mixture stirred for 10 minutes. A solution of (±)-3-hydroxy-5-(3-pyridyl)-1-pentyl para-toluenesulfonate (0.250 g) in anhydrous dimethylformamide (2 ml) was added and the mixture stirred at 60° C. for 30 minutes before being added to water (30 ml). Saturated aqueous sodium chloride solution (30 ml) was added and the mixture extracted with ethyl acetate (2×50 ml). The combined organic extracts were dried over anhydrous magnesium sulfate, filtered and concentrated under reduced pressure. The residue was purified by column chromatography over silica eluting with acetone:hexane (2:3) to give the title compound as a solid (0.210 g) which was recrystallised from ethyl acetate:hexane.

m.p. 85.5–87.5° C.

MS (APCI) 334.2 (M+H)$^+$ $^1$H NMR (DMSO-d$_6$) 8.46(1 H, s); 8.39(1 H, d); 7.65-7.58(5 H, m); 7.43(2 H, t); 7.32-7.29(2 H, m); 7.01(2 H, d); 4.75(1 H, d); 4.17-4.08(2 H, m); 3.72-3.63(1 H, m); 2.80-2.72 (1 H, m); 2.70-2.61(1 H, m); 1.97-1.86(1 H, m); 1.81-1.62(3 H, m).

EXAMPLE 98

(2R)-1-(3'-(Methylaminosulfonyl)biphenyl-4-yloxy)-4-(3-pyridyl)-2-butanol oxalic acid salt

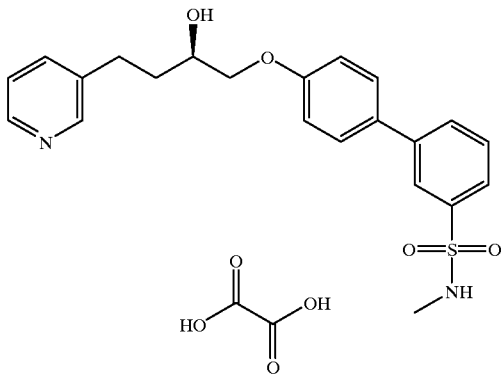

a) (2R)-1-(4-Bromophenoxy)-4-(3-pyridyl)-2-(tert-butyldimethylsilyloxy)butane

Sodium hydride (60% dispersion in mineral oil, 0.138 g) was washed with hexane (2 ml) under nitrogen. Anhydrous dimethylformamide (1 ml) was added followed by a solution of 4-bromophenol (0.596 g) in anhydrous dimethylformamide (7 ml) and the mixture stirred for 10 minutes. A solution of (2R)-2-(tert-butyldimethylsilyloxy)-4-(3-pyridyl)-1-butyl para-toluenesulfonate (1.00 g, Example 34d) in anhydrous dimethylformamide (2 ml) was then added and the mixture stirred at 60° C. for 3 hours before adding to water (50 ml). Saturated aqueous sodium chloride solution (50 ml) was added and the mixture extracted with ether (2×100 ml). The combined organic extracts were dried over anhydrous magnesium sulfate, filtered and concentrated under reduced pressure. The residue was purified by column chromatography over silica eluting with ethyl acetate:hexane (1:2) to give the sub-title compound as an oil (0.987 g).

MS (APCI) 436.2/438.2 (M+H)$^+$ $^1$H NMR (CDCl$_3$) 8.47(1 H, d); 8.45(1 H, dd); 7.51(1 H, dt); 7.37(2 H, d); 7.20(1 H, dd); 6.76(2 H, d); 4.15-4.04(1 H, m); 3.90-3.79(2 H, m); 2.84-2.62(2 H, m); 2.00-1.79 (2 H, m); 0.92(9 H, s); 0.13(3 H, s); 0.09(3 H, s).

b) Methyl 3-bromobenzenesulfonamide

3-Bromobenzenesulfonyl chloride (0.33 g) was added to a saturated solution of methylamine in methanol (50 ml). After 10 minutes, the solution was concentrated under reduced pressure. Water (20 ml) was added to the residue and the resulting solid filtered and dried in vacuo to give the sub-title compound (0.32 g).

$^1$H NMR (DMSO-d$_6$) 7.95-7.84(2 H, m); 7.79(1 H, m); 7.65(1 H, br); 2.43(3 H, s).

c) (2R)-1-(3'-(Methylaminosulfonyl)biphenyl-4-yloxy)-4-(3-pyridyl)-2-butanol oxalic acid salt A solution of n-butyllithium (2.5 M in hexanes, 0.50 ml) was added to a stirred solution of (2R)-1-(4-bromophenoxy)-4-(3-pyridyl)-2-(tert-butyldimethylsilyloxy)butane (0.50 g, Example 98a) in anhydrous tetrahydrofuran (5 ml) at −78° C. under nitrogen. After 15 minutes, the reaction mixture was added dropwise to a solution of triisopropyl borate (0.53 ml) in anhydrous tetrahydrofuran (5 ml) at −78° C. under nitrogen. The mixture was allowed to warm to room temperature and stirred for 30 minutes. Hydrochloric acid (2 M, 10 ml) was added and the mixture stirred for 30 minutes then concentrated under reduced pressure. A solution of methyl 3-bromobenzenesulfonamide (0.32 g) in ethanol (3 ml), tetrakis(triphenylphosphine)palladium(0) (60 mg), aqueous sodium carbonate (2 M, 3 ml) and toluene (12 ml) were added to the residual gum. The mixture was then heated at reflux, under nitrogen for 6 hours before being added to water (50 ml). The mixture was extracted with ethyl acetate (2×50 ml), the combined organic extracts dried over anhydrous magnesium sulfate, filtered and concentrated under reduced pressure. The residue was dissolved in tetrahydrofuran (5 ml) and tetrabutylammonium fluoride hydrate (0.50 g) was added. The mixture was stirred for 2 hours before being added to water (30 ml). The mixture was extracted with ethyl acetate (2×50 ml), the combined organic extracts dried over anhydrous magnesium sulfate, filtered and concentrated under reduced pressure. The residue was purified by column chromatography over silica eluting with ethyl acetate to give an oil (0.297 g). The latter was converted to the oxalate salt upon treatment with oxalic acid (excess) in ether and was recrystallised from ethyl acetate. The resulting hydroscopic solid was dissolved in methanol and the solution evaporated under reduced pressure to give the title compound as a foam (0.178 g).

MS (APCI) 413.1 ((M-oxalic acid)+H)$^+$ $^1$H NMR (DMSO-d$_6$) 8.49(1 H, s); 8.42(1 H, d); 7.96(1 H, s); 7.90(1 H, d); 7.73-7.62 (5 H, m); 7.49(1 H, q); 7.34(1 H, dd); 7.08(2 H, d); 3.95(2 H, d); 3.83-3.78(1 H, m); 2.87-

2.78(1 H, m); 2.76-2.65(1 H, m); 2.44(3 H, d); 1.93-1.82(1 H, m); 1.79-1.70(1 H, m).

EXAMPLE 99

(2R)-1-(3'-Hydroxybiphenyl-4-yloxy)-4-(3-pyridyl)-2-butanol

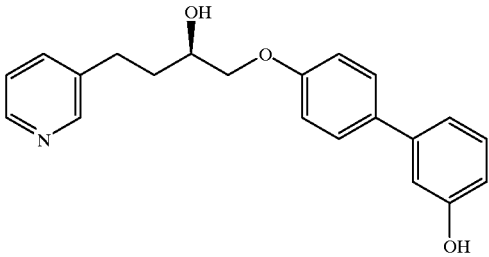

Solid (2R)-1-(3'-(Benzyloxy)biphenyl-4-yloxy)-4-(3-pyridyl)-2-butanol (0.88 g, Example 93c) was dissolved in dry ethanol (150 ml) and hydrogenolysed for 24 hours at 3 atmospheres pressure over a palladium on carbon catalyst (10%, 0.09 g). The reaction mixture was filtered through Celite® and the residue washed with ethanol. The combined filtrate and washings were concentrated under reduced pressure and the residue obtained purified by column chromatography over silica eluting with dichloromethane:methanol (98:2) to give the title compound as a white solid (0.52 g).

m.p. 169° C.

MS (APCI) 336 (M+H)$^+$ $^1$H NMR (DMSO-d$_6$) 8.46(1 H, d); 8.40(1 H, dd); 7.66(1 H, d); 7.51(2 H, d); 7.31(1 H, dd); 7.21(1 H, t); 7.00(3 H, dd); 6.96(1 H, s); 6.70(1 H, dd); 5.07(1 H, d); 3.92(2 H, d); 3.85-3.72(1 H, m); 2.81-2.77(1 H, m); 2.72-2.68(1 H, m); 1.87-1.84(1 H, m); 1.74-1.71(1 H, m).

EXAMPLE 100

(2R)-1-(2-Chlorobiphenyl-4-yloxy)-4-(3-pyridyl)-2-butanol

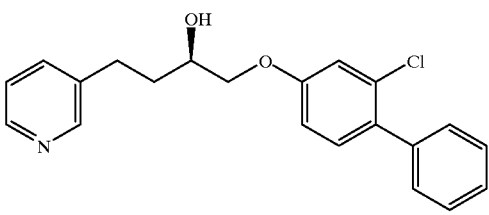

a) 2-Chlorobiphenyl-4-ol

Prepared according to the method described in Example 33a) from 4-bromo-3-chlorophenol (3.0 g), benzeneboronic acid (2.0 g), tetrakis(triphenylphosphine)palladium(0) (0.43 g), toluene (30 ml), ethanol (10 ml) and aqueous sodium carbonate (2 M, 14 ml) with heating at 120° C. for 30 minutes. After work up the residue was purified by chromatography over silica eluting with ethyl acetate:hexane (1:9) to give an impure sample of the sub-title compound (2.94 g), which was used in the next step without further purification.

MS (APCI) (~65% pure) 203.1 (M−H)$^-$ b) (2R)-1-(2-Chlorobiphenyl-4-yloxy)-4-(3-pyridyl)-2-butanol Prepared according to the method described in Example 26e) from (2R)-2-(tert-butyldimethylsilyloxy)-4-(3-pyridyl)-1-butyl para-toluenesulfonate (0.8 g), sodium hydride (60% dispersion in mineral oil, 0.10 g) and 2-chlorobiphenyl-4-ol (0.50 g) in dimethylformamide (15 ml). The adduct was dissolved in tetrahydrofuran (10 ml) and tetrabutylammonium fluoride (1.0 g) was added. The reaction was stirred at room temperature for 5 hours and was then poured into brine and extracted with ether. The combined organic extracts were dried over anhydrous magnesium sulfate, filtered and concentrated under reduced pressure. The residue was purified by reverse phase HPLC to give the title compound as a colourless gum (0.073 g).

MS (APCI) 354 (M+H)$^+$ $^1$H NMR (DMSO-d$_6$) 8.45(1 H, d); 8.0)1 H, dd); 7.65(1 H, dt); 7.5-7.36(5 H, m); 7.36-7.3(2 H, m); 7.15(1 H, d); 7.00(1 H, dd); 5.08(1 H, d); 4.0-3.95(2 H, m); 3.85-3.75(1 H, m); 2.87-2.62(2 H, m); 1.93-1.65(2 H, m).

EXAMPLE 101

(2R)-1-(3-Fluorobiphenyl-4-yloxy)-4-(3-pyridyl)-2-butanol

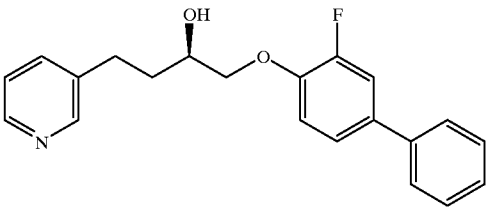

a) 3-Fluoro-4-methoxybiphenyl

Prepared according to the method as described in Example 33a) from 4-bromo-2-fluoroanisole (1.0 g), benzeneboronic acid (0.6 g), tetrakis(triphenylphosphine)palladium(0) (0.12 g), toluene (15 ml), ethanol (3 ml) and aqueous sodium carbonate (2 M, 5 ml) with heating at 120° C. for 2 hours. After work up the residue was purified by chromatography over silica eluting with ethyl acetate:hexane (1:9) to give the sub-title compound as a white solid (0.99 g).

m.p. 86–87° C.

MS (EI) 202 (M)$^+$ $^1$H NMR (DMSO-d$_6$) 7.65(2 H, dd); 7.55(1 H, dd); 7.5-7.4(3 H, m); 7.33(1 H, t); 7.25(1 H, t); 3.88(3 H, s).

b) 3-Fluorobiphenyl-4-ol

Prepared according to the method described in example 36b) from 3-fluoro-4-methoxybiphenyl (0.99 g), boron tribromide (1.0 M in dichloromethane, 9.8 ml) and dichloromethane (15 ml). After work up the residue was purified by column chromatography over silica eluting with dichloromethane:ethanol (19:1) to give the sub-title compound as a pale yellow crystalline solid (0.52 g).

m.p. 107–109° C.

MS (EI) 188 (M)$^+$ $^1$H NMR (DMSO-d$_6$) 9.97(1 H, s); 7.62(2 H, d); 7.5-7.39(3 H, m); 7.35-7.27(2 H, m); 7.02(1 H, t).

c) (2R)-1-(3-Fluorobiphenyl-4-yloxy)-4-(3-pyridyl)-2-butanol

Prepared according to the method described in Example 26e) from (2R)-2-(tert-butyldimethylsilyloxy)-4-(3-pyridyl)-1-butyl para-toluenesulfonate (1.0 g), sodium hydride (60% dispersion in mineral oil, 0.115 g) and 3-fluorobiphenyl-4-ol (0.52 g) in dimethylformamide (15 ml). The adduct was dissolved in tetrahydrofuran (10 ml) and tetrabutylammonium fluoride (1.08 g) was added. The reaction was stirred at ambient temperature for 3 hours and was then poured into brine and extracted with ether. The combined organic extracts were dried over anhydrous magnesium sulfate, filtered and concentrated under reduced pressure. The residue obtained was purified by column chromatography over silica eluting with dichloromethane:ethanol (19:1) to give the title compound as a white solid (0.25 g).

m.p. 124–125° C.

MS (APCI) 338 (M+H)+

$^1$H NMR (DMSO-$d_6$) 8.46(1 H, d); 8.4(1 H, dd); 7.65(3 H, d); 7.55(1 H, dd); 7.45(3 H, t); 7.39-7.2(3 H, m); 5.1(1 H, d); 4.0(2 H, d); 3.9-3.75(1 H, m); 2.9-2.6(2 H, m); 1.95-1.65(2 H, m).

EXAMPLE 102

(2R)-1-(3'-(Acetoxy)biphenyl-4-yloxy)-4-(3-pyridyl)-2-butanol

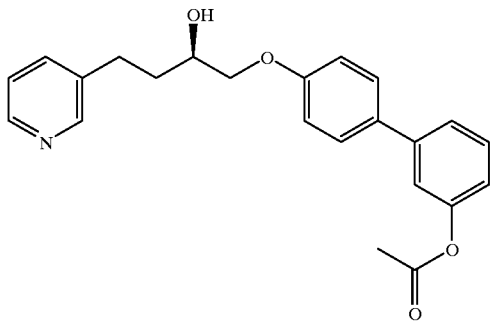

(2R)-1-(3'-Hydroxybiphenyl-4-yloxy)-4-(3-pyridyl)-2-butanol (0.34 g, Example 99) was dissolved in dichloromethane (10 ml) and cooled to 0° C. using ice and water. Triethylamine (0.14 ml) and acetic anhydride (0.09 ml) were added and the reaction mixture allowed to room temperature with stirring for 18 hours. The reaction mixture was poured into water and extracted with ethyl acetate. The combined extracts were dried over anhydrous magnesium sulfate, filtered and concentrated under reduced pressure. The residue was purified by column chromatography over silica eluting with dichloromethane:methanol (97:3) to give the title compound as an oil (0.20 g).

MS (APCI) 378 (M+H)+

$^1$H NMR (DMSO-$d_6$) 8.46(1 H, d); 8.40(1 H, dd); 7.66(1 H, dd); 7.60(2 H, d); 7.48(2 H, quintet); 7.37(1 H, t); 7.31(1 H, dd); 7.07(1 H, t); 7.03(2 H, d); 5.07(1 H, d); 3.93(2 H, d); 3.85-3.72(1 H, m); 2.90-2.62(2 H, m); 2.29(3 H, s); 1.93-1.66(2 H, m).

EXAMPLE 103

(±)-(E)-1-(4-(2-Phenylethenyl)phenoxy)-5-(3-pyridyl)-2-pentanol

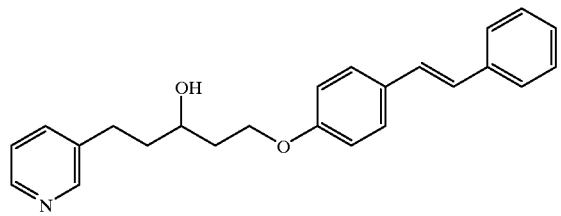

Prepared according to the method described in Example 96d) from sodium hydride (60% dispersion in mineral oil, 0.045 g), trans-4-hydroxystilbene (0.219 g) and (±)-3-hydroxy-5-(3-pyridyl)-1-pentyl para-toluenesulfonate (0.250 g) in anhydrous dimethylformamide (5 ml). The crude product was purified by column chromatography over silica eluting with methanol:dichloromethane (1:19) to give the title compound (0.167 g) as a solid which was recrystallised from ethyl acetate:hexane.

m.p. 110–111° C.

MS (APCI) 360.2 (M+H)+

$^1$H NMR (DMSO-$d_6$) 8.45(1 H, d); 8.39(1 H, dd); 7.63(1 H, dt); 7.57-7.51(4 H, m); 7.51(2 H, t); 7.32-7.21(2 H, m); 7.14(2 H, ABq); 6.93(2 H, d); 4.73(1 H, d); 4.17-4.03 (2 H, m); 3.71-2.59(1 H, m); 2.80-2.59(2 H, m); 1.96-1.83(1 H, m); 1.92-1.60(3 H, m).

EXAMPLE 104

(±)-1-(4-(Bicyclo[2,2,2]oct-1-ylmethoxy)phenoxy)-4-(3-pyridyl)-2-butanol oxalic acid salt

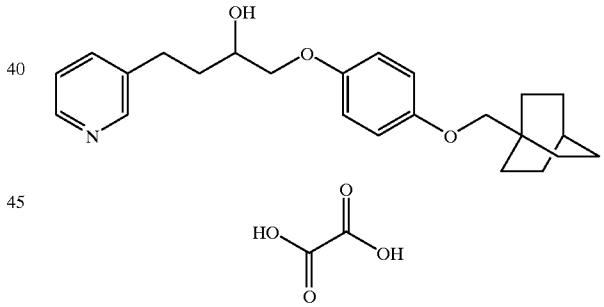

a) (±)-1-(4-Hydroxyphenoxy)-4-(3-pyridyl)-2-butanol

Prepared according to the method described in Example 99 from (±)-1-(4-benzyloxyphenoxy)-4-(3-pyridyl)-2-butanol (0.170 g) and 10% palladium on charcoal (0.060 g) in ethanol (12 ml) to give the sub-title compound as an oil (0.119 g).

MS (APCI) 260.2 (M+H)+

$^1$H NMR (DMSO-$d_6$) 8.91(1 H, s); 8.45(1 H, s); 8.39(1 H, d); 7.64(1 H, d); 7.30(1 H, dd); 6.73(2 H, d); 6.65(2 H, d); 4.97(1 H, d); 3.80-3.64(3 H, m); 2.82-3.74(1 H, m); 2.69-2.61(1 H, m); 1.84-1.77(1 H, m); 1.72-1.65(1 H, m).

b) Bicyclo[2,2,2]oct-1-ylmethyl para-toluenesulfonate

Solid para-toluenesulfonyl chloride (0.449 g) was added to a solution of bicyclo-[2,2,2]oct-1-ylmethanol (300 mg) and triethylamine (0.45 ml) in anhydrous acetonitrile (6 ml) under nitrogen. The mixture was stirred at room temperature for 16 hours then heated at reflux for 18 hours, poured into saturated aqueous sodium hydrogen carbonate solution and extracted with ether. The combined organic extracts were dried over anhydrous magnesium sulfate, filtered and concentrated under reduced pressure. The residue was purified by column chromatography over silica eluting with ether::hexane (1:9) and further purified by preparative normal-phase HPLC on a Dynamax™ Silica column with hexane::ethyl acetate gradient elution to give the sub-title compound as an oil (0.180 g).

¹H NMR (CDCl₃) 7.77(2 H, d); 7.33(2 H, d); 3.59(2 H, s); 2.45(3 H, s); 2.58-1.50(7 H, m); 1.35-1.30(6 H, m).

c) (±)-1-(4-(Bicyclo[2,2,2]oct-1-ylmethoxy)phenoxy)-4-(3-pyridyl)-2-butanol oxalic acid salt Anhydrous potassium carbonate (0.100 g) was added to a solution of bicyclo[2,2,2]oct-1-ylmethyl para-toluenesulfonate (0.180 g) and (±)-1-(4-hydroxyphenoxy)-4-(3-pyridyl)-2-butanol (0.115 g) in anhydrous dimethylformamide (3 ml). The mixture was heated at reflux under nitrogen, with stirring for 6 hours then cooled to room temperature before being poured into water (20 ml). The mixture was diluted with saturated aqueous sodium chloride solution (20 ml) and extracted with ethyl acetate (2×30 ml). The combined organic extracts were dried over anhydrous magnesium sulfate, filtered and concentrated under reduced pressure. The residue was purified by column chromatography over silica eluting with acetone:hexane (2:3) to give an oil. This oil was treated with oxalic acid (excess) in ether to give the title compound as a solid (0.167 g) which was recrystallised from ethyl acetate.

m.p. 156–157° C.

MS (APCI) 382 (M+H)⁺

¹H NMR (DMSO-d₆) 8.47(1 H, s); 8.41(1 H, d); 7.68(1 H, d); 7.34(1 H, dd); 6.81(4 H, ABq); 3.80-3.70(3 H, m); 3.46(2 H, s); 2.84-2.61(2 H, m); 1.90-1.78(1 H, m); 1.76-1.63 (1 H, m); 1.57-1.52(7 H, m); 1.51-1.42(6 H, m).

EXAMPLE 105

(±)-(E)-1-(2-Methoxy-4-(2-phenylethenyl)phenoxy)-5-(3-pyridyl)-2-pentanol

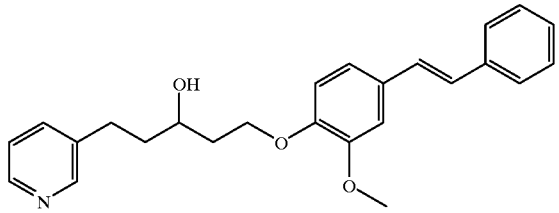

Prepared according to the method described in Example 96d) from sodium hydride (60% dispersion in mineral oil, 55 mg), trans-4-hydroxy-3-methoxystilbene (0.314 g) and (±)-3-hydroxy-5-(3-pyridyl)-1-pentyl para-toluenesulfonate (310 mg) in anhydrous dimethylformamide (6 ml). The crude product was purified by column chromatography over silica eluting with methanol:dichloromethane (1:19) to give the title compound (0.197 g) as a solid which was recrystallised from ethyl acetate:hexane.

m.p. 110.5–111° C.

MS (APCI) 390.1 (M+H)⁺

¹H NMR (DMSO-d₆) 8.45(1 H, s); 8.39(1 H, d); 7.64(1 H, d); 7.56(2 H, d); 7.36(2 H, t); 7.28(1 H, dd); 7.7.26-7.21(2 H, m); 7.15(2 H, ABq); 7.09(1 H, d); 6.95(1 H, d); 4.70(1 H, d); 4.15-4.02(2 H, m); 3.80(3 H, s); 3.72-3.60(1 H, m); 2.81-2.59(2 H, m); 1.96-1.83(1 H, m); 1.82-1.60(3 H, m).

EXAMPLE 106

(2R)-4-(3-Pyridyl)-1-(3-Trifluoromethylbiphenyl-4-yloxy)-2-butanol

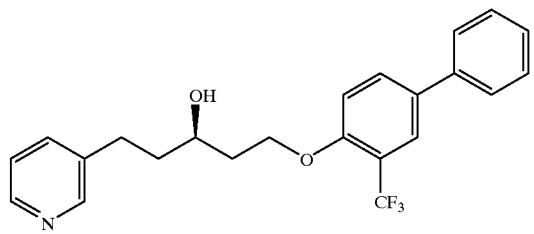

(a) (2R)-1-(4Bromo-2-trifluoromethylphenoxy)-2-(tert-butyldimethylsilyloxy)-4-(3-pyridyl)butane Prepared according to the method described in Example 26e) from (2R)-2-(tert-butyldimethylsilyloxy)-4-(3-pyridyl)-1-butyl para-toluenesulfonate (1.5 g), sodium hydride (60% dispersion in mineral oil, 0.220 g) and an impure sample of 4-bromo-2-trifluoromethylphenol (1.0 g, 66% pure, EP-A-0 648 729) in dimethylformamide (15 ml). After work up the adduct was purified by column chromatography over silica eluting with ethyl acetate:hexane (1:4) to give an impure sample of the sub-title compound as a pale yellow oil (1.02 g, ~67% pure).

MS (APCI) 506 (M+H)⁺

(b) (2R)-2-(tert-Butyldimethylsilyloxy)-4-(3-pyridyl)-1-(3-trifluoromethylbiphenyl-4-yloxy)butane Prepared according to the method as described in Example 33a) from (2R)-1-(4-bromo-2-trifluoromethylphenoxy)-2-(tert-butyldimethylsilyloxy)-4-(3-pyridyl)butane (1.0 g, ~67% pure), benzeneboronic acid (0.18 g), tetrakis(triphenylphosphine)palladium(0) (0.035 g), toluene (10 ml), ethanol (2 ml) and aqueous sodium carbonate (2 M, 1.45 ml) with heating at 120° C. for 1 hour. After work up the residue was purified by chromatography over silica eluting with ethyl acetate:hexane (1:9) to give an impure sample of the sub-title compound as a light brown oil (0.80 g, ~67% pure).

MS (APCI) 502 (M+H)⁺

(c) (2R)-4-(3-Pyridyl)-1-(3-trifluoromethylbiphenyl-4-yloxy)-2-butanol (2R)-2-(tert-Butyldimethylsilyloxy)-4-(3-pyridyl)-1-(3-trifluoromethylbiphenyl-4-yloxy)butane (0.8 g, ~67% pure) was dissolved in tetrahydrofuran (10 ml) and tetrabutylammonium fluoride (0.84 g) was added. The reaction was stirred at ambient temperature for 1 hour and was then poured into brine and extracted with ether. The combined organic extracts were dried over anhydrous magnesium sulfate, filtered, concentrated under reduced pressure. The residue obtained was purified by reverse phase HPLC to give the title compound as a white solid (0.13 g).

m.p. 82.5–83.5° C.

MS (APCI) 388 (M+H)⁺

¹H NMR (DMSO-d₆) 8.45(1 H, s); 8.40(1 H, d); 7.9(1 H, dd); 7.82(1 H, d); 7.7-7.6(3 H, m); 7.45(2 H, t); 7.4-7.25(3 H, m); 5.07(1 H, d); 4.2-4.0(2 H, m); 3.9-3.75(1 H, m); 2.9-2.6(2 H, m); 2.0-1.68(2 H, m).

EXAMPLE 107

(2R)-1-[6-(Cyclopropylmethoxy)-1-fluoro-2-naphthyloxy]-4-(3-pyridyl)-2-butanol

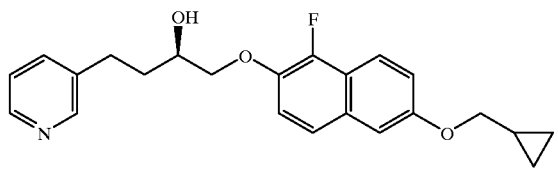

a) 6-Cyclopropylmethoxy-1-fluoro-2-hydroxynaphthalene

1-Fluoro-2,4,6-trimethylpyridinium trifluoromethanesulfonate (0.35 g) was added to a solution of 2-cyclopropylmethoxy-6-hydroxynaphthalene (0.22 g, Example 60a) in dichloromethane (10 ml). After 3 days at room temperature, the mixture was purified directly by column chromatography over silica eluting with dichloromethane to give the sub-title compound as a solid (0.12 g).

MS (APCI) 231.2 (M−H)⁻

$^1$H NMR (DMSO-d$_6$) 9.72(1 H, br); 7.78(1 H, d); 7.46(1 H, d); 7.24(1 H, s); 7.21-7.16 (2 H, m); 3.89(2 H, d); 1.36-1.22(1 H, m); 0.62-0.58(2 H, m); 0.38-0.33(2 H, m).

b) (2R)-1-[6-(Cyclopropylmethoxy)-1-fluoro-2-naphthyloxy]-4-(3-pyridyl)-2-butanol Prepared according to the method described in Example 26e) from (2R)-2-(tert-butyldimethylsilyloxy)-4-(3-pyridyl)-1-butyl para-toluenesulfonate (0.215 g), sodium hydride (60% dispersion in mineral oil, 0.02 g) and 6-cyclopropylmethoxy-1-fluoro-2-hydroxynaphthalene (0.115 g) in dimethylformamide (3 ml). The adduct was dissolved in tetrahydrofuran (5 ml) and tetrabutylammonium fluoride (0.25 g) was added. The reaction was stirred at room temperature for 2 hours and was then poured into water and extracted with ethyl acetate. The organic extracts were dried over anhydrous magnesium sulfate, filtered and concentrated under reduced pressure. The residue was purified by column chromatography eluting with acetone:hexane (2:3) to give the title compound as a solid (0.077 g).

m.p. 84–85° C.

MS (APCI) 382.1 (M+H)⁺

$^1$H NMR (DMSO-d$_6$) 8.45(1 H, d); 8.39(1 H, dd); 7.84(1 H, d); 7.64(1 H, dt); 7.58(1 H, d); 7.44(1 H, t); 7.32-7.28(2 H, m); 7.23(1 H, dd); 5.08(1 H, d); 4.12-4.02(2 H, m); 3.91(2 H, d); 3.84-3.77(1 H, m); 2.97-2.62(2 H, m); 1.96-1.83(1 H, m); 1.80-1.68(1 H, m); 1.36-1.24(1 H, m); 0.63-0.57(2 H, m); 0.39-0.35(2 H, m).

EXAMPLE 108

The compounds of Examples 1 to 107 were tested in the test described hereinbefore and were found to inhibit histamine release at a concentration of less than 10$^{-4}$ M (IC$_{50}$) in all cases.

We claim:

1. A compound of formula I,

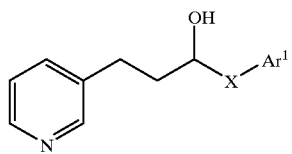

I wherein—

X represents (CH$_2$)$_n$O, (CH$_2$)$_n$S or C$_2$ alkylene;

n represents 1 or 2;

Ar$^1$ represents indanyl, naphthyl or phenyl, which latter two groups may be substituted by one or more substituents selected from the group consisting of chloro, fluoro, OR$^1$, O(CH$_2$)$_m$CONR$^{20}$R$^{21}$, C(O)R$^2$, C$_{1-6}$ alkyl (optionally substituted by one or more fluorine atoms), pyridyl, thiazinyl, phenyl and C$_{7-9}$ alkylphenyl which latter two groups are optionally substituted by one or more substituent selected from halo, nitro, OR$^3$, C$_{1-6}$ alkyl (optionally substituted by one or more fluorine atoms), C(O)R$^4$, C(O)OR$^5$, C(O)N(R$^6$)R$^7$, CN, CH$_2$OR$^{14}$, CH$_2$NR$^{15}$R$^{16}$, N(R$^8$)R$^9$, N(R$^{10}$)SO$_2$R$^{11}$, N(R$^{12}$)C(O)R$^{13}$, OC(O)R$^{19}$ and SO$_2$NR$^{17}$R$^{18}$;

m represents an integer 1 to 3;

R$^1$, R$^2$ and R$^3$ independently represent H, C$_{1-10}$ alkyl (optionally substituted by one or more fluorine atoms), C$_{7-9}$ alkylphenyl or phenyl, which latter group is optionally substituted by hydroxy; and R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$ and R$^{21}$ independently represent H, C$_{1-6}$ alkyl (optionally substituted by one or more fluorine atoms) or phenyl;

in which any alkyl group present may be interrupted by one or more oxygen atoms;

provided that when X represents CH$_2$CH$_2$, Ar$^1$ may not represent phenyl or phenyl substituted with one or more substituents OR$^1$, in which R$^1$ represents C$_{1-10}$ alkyl;

or a pharmaceutically acceptable derivative thereof.

2. A compound of formula I as defined in claim 1, wherein X represents CH$_2$O, CH$_2$S or C$_2$ alkylene and Ar$^1$ represents— naphthyl, which may be substituted by one or more substituents selected from chloro, fluoro, OR$^1$, O(CH$_2$)$_m$CONR$^{20}$R$^{21}$, and C$_{1-6}$ alkyl (optionally substituted by one or more fluorine atoms); or biphenylyl, which may be substituted on the ring adjacent to X by one or more substituents selected from chloro, fluoro, OR$^1$, O(CH$_2$)$_m$CONR$^{20}$R$^{21}$ and C$_{1-6}$ alkyl (optionally substituted by one or more fluorine atoms), and on the ring remote from X by one or more substituent selected from halo, nitro, OR$^3$, C$_{1-6}$ alkyl (optionally substituted by one or more fluorine atoms), C(O)R$^4$, C(O)OR$^5$ C(O)N(R$^6$)R$^7$, CN, CH$_2$OR$^{14}$, CH$_2$NR$^{15}$R$^{16}$, N(R$^8$)R$^9$, N(R$^{10}$)SO$_2$R$^{11}$, N(R$^{12}$)C(O) R$^{13}$, OC(O)R$^{19}$ and SO$_2$NR$^{17}$R$^{18}$;

or a pharmaceutically acceptable derivative thereof.

3. A pharmaceutical formulation including a compound of formula I as defined in claim 1 or a pharmaceutically acceptable derivative thereof, in admixture with a pharmaceutically acceptable adjuvant, diluent or carrier.

4. A method of treatment of a reversible obstructive airways disease which comprises administering a therapeutically effective amount of a compound of formula I as defined in claim 1, or a pharmaceutically acceptable derivative thereof, to a person suffering from, or susceptible to, such a disease.

5. A method as claimed in claim 4, wherein the disease is asthma.

6. A process for the preparation of compounds of formula I as defined in claim 1 which comprises:

(a) reduction of a corresponding compound of formula II,

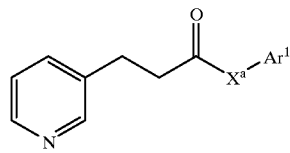

II wherein $X^a$ represents $(CH_2)_nS$, $(CH_2)_nO$ or $C_2$ alkylene and $Ar^1$ is as defined in claim 1;

(b) preparation of a compound of formula I, wherein X represents $CH_2S$, CH=CH or C≡C, by reaction of 3-(3-pyridyl)-1-propionaldehyde with a compound of formula III, MZAr¹    III wherein M represents Li, Na, K or MgHal where Hal represents Cl, Br or I, Z represents $CH_2S$, CH=CH or C≡C and $Ar^1$ is as defined in claim 1;

(c) preparation of a compound of formula I, wherein X represents $CH_2S$, $CH_2O$ or $(CH_2)_2$, by reaction of 3-(2-oxiranylethyl)pyridine either with a compound of formula IV, MYAr¹    IV or with a compound of formula VII, HYAr¹    VII wherein Y represents O, S or $CH_2$, M is as hereinbefore defined and $Ar^1$ is as defined in claim 1;

(d) preparation of a compound of formula I, wherein X represents $CH_2S$, $CH_2O$ or $(CH_2)_2$, by reaction of a compound of formula V,

V wherein M is as defined above, with a compound of formula VI,

VI wherein Y is as defined above and $Ar^1$ is as defined in claim 1;

(e) preparation of a compound of formula I, wherein X represents $CH_2S$, $CH_2O$ or $(CH_2)_2$, by reaction of α-(chloromethyl)-3-pyridinepropanol either with a compound of formula IV, MYAr¹    IV or with a compound of formula VII, HYAr¹    VII wherein Y and M are as defined above and $Ar^1$ is as defined in claim 1;

(f) preparation of a compound of formula I, wherein X represents $CH_2O$ or $CH_2S$, by reaction of a compound of formula IV or VII, as defined above, with a suitably protected and activated derivative of 4-(3-pyridyl)-1,2-butanediol;

(g) preparation of a compound of formula I, wherein X is as defined in claim 1 and $Ar^1$ represents an —$Ar^3$—$Ar^4$ group in which $Ar^3$ represents naphthylene or phenylene optionally substituted by one or more substituents selected from chloro, fluoro, $OR^1$, $O(CH_2)_mCONR^{20}R^{21}$, $C(O)R^2$, $C_{1-6}$ alkyl (optionally substituted by one or more fluorine atoms) and $Ar^4$ represents pyridyl, thiazinyl or phenyl which latter group is optionally substituted by one or more substituents selected from halo, nitro, $OR^3$, $C_{1-6}$ alkyl (optionally substituted by one or more fluorine atoms), $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$, $SO_2NR^{17}R^{18}$ by reaction of a compound of formula VIII,

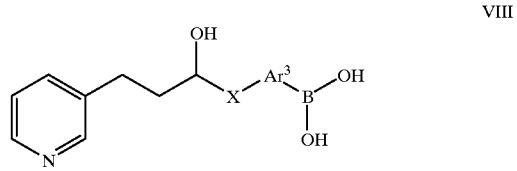

VIII wherein X and $Ar^3$ are as defined above, with an aryl halide of formula XX Ar⁴Hal    XX wherein Hal represents triflate, Cl, Br or I and $Ar^4$ is as defined above;

(h) preparation of a compound of formula I wherein X is C≡C by reaction between a compound of formula X, QAr¹    X wherein Q represents Br, I or triflate and $Ar^1$ is as defined in claim 1, with 5-(3-pyridyl)pent-1-yn-3-ol;

(i) preparation of a compound of formula I, wherein X is as defined in claim 1 and $Ar^1$ represents an —$Ar^3$—$Ar^4$ group in which $Ar^3$ and $Ar^4$ are as defined above, by reaction of a compound of formula XI,

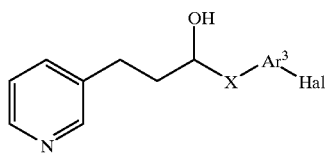

wherein Hal represents Cl, Br, I or triflate and X and $Ar^3$ are as defined above, with an arylboronic acid of formula XXI,

wherein $Ar^4$ is as defined above;

(j) reduction of a compound of formula XII,

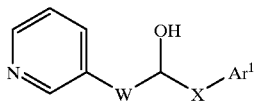

wherein W represents CH=CH or C≡C and X and $Ar^1$ are as defined in claim 1, by reduction with a suitable reducing agent;

(k) preparation of a compound of formula I, wherein X is CH=CH, by reaction of a phosphonium salt of formula XIII,

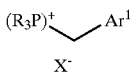

wherein R is an aryl group, $X^-$ is chloride, bromide or iodide and $Ar^1$ is as defined in claim 1, with a suitably protected derivative of 2-hydroxy-4-(3-pyridyl) butyraldehyde, or reaction of a compound of formula XXII,

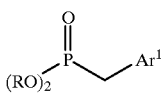

wherein R represents $C_{1-6}$ alkyl or aryl and $Ar^1$ is as defined in claim 1, with a suitably protected derivative of 2-hydroxy-4-(3-pyridyl)butyraldehyde; (1) preparation of a compound of formula I, wherein X is $(CH_2)_2O$ or $(CH_2)_2S$, by reaction between a compound of formula VII, as defined above, and an optionally protected and suitably activated derivative of 5-(3-pyridyl)-1,3-pentanediol;

(m) preparation of a compound of formula I, wherein X is $CH_2CH_2$, by reduction of a corresponding compound of formula I wherein X is C≡C;

(n) preparation of a compound of formula I, wherein X is $CH_2CH_2$, by reduction of a corresponding compound of formula I wherein X is CH=CH;

(o) preparation of a compound of formula I, wherein X is trans-CH=CH, by reduction of a corresponding compound of formula I wherein X is C≡C;

(p) preparation of a compound of formula I, wherein X is cis-CH=CH, by reduction of a corresponding compound of formula I wherein X is C≡C;

(q) preparation of a compound of formula I, wherein X is CH=CH, by reaction of a compound of formula IX, as defined above, with 5-(3-pyridyl)-1-penten-3-ol;

(r) preparation of a compound of formula I, wherein X is as defined in claim 1 and $Ar^1$ represents an $—Ar^3—Ar^6$ group in which $Ar^3$ is as defined above and $Ar^6$ represents a $C_{7-9}$ alkylphenyl group which is optionally substituted by one or more substituents selected from halo, nitro, $OR^3$, $C_{1-6}$ alkyl (optionally substituted by one or more fluorine atoms), $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$, by reaction between a compound of formula XI, as defined above, and a compound of formula XXV,

wherein U represents a $C_{2-3}$ alkylenyl group and $Ar^6$ is as defined;

(s) reduction of a compound of formula XXVI,

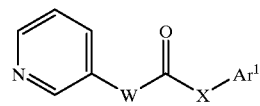

wherein X and $Ar^1$ are as defined in claim 1 and W is as defined above;

(t) preparation of a compound of formula I, wherein $Ar^1$ represents naphthyl or phenyl substituted by one or more substituents selected from chloro, fluoro, $OR^1$, $O(CH_2)_mCONR^{20}R^{21}$, $C(O)R^2$, $C_{1-6}$ alkyl (optionally substituted by one or more fluorine atoms), or by phenyl or $C_{7-9}$ alkylphenyl which latter two groups are optionally substituted by one or more substituent selected from halo, nitro, $OR^3$, $C_{1-6}$ alkyl (optionally substituted by one or more fluorine atoms), $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$ and $SO_2NR^{17}R^{18}$, from a corresponding compound of formula I including a group convertible to a halo, $OR^1$, $O(CH_2)_mCONR^{20}R^{21}$, $C(O)R^2$, alkyl, fluoroalkyl, nitro, $OR^3$, $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$ or $SO_2NR^{17}R^{18}$ group by functional group interconversion;

wherein any functional group present may be protected before reaction occurs and deprotected to give the compounds of formula I.

7. A compound of formula II

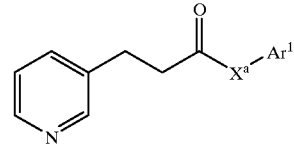

or of formula XIV,

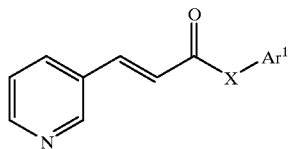

wherein $X^a$ represents $(CH_2)_nS$ or $(CH_2)_nO$ or $C_2$ alkylene, $Ar^1$ is indanyl, naphthyl or phenyl, which latter two groups may be substituted by one or more substituents selected from the group consisting of chloro, fluoro, $OR^1$, $O(CH_2)_mCONR^{20}OR^{21}$, $C(O)R^2$, $C_{1-6}$ alkyl optionally substituted by one or more fluorine atoms, pyridyl, thiazinyl, phenyl and $C_{7-9}$ alkylphenyl which latter two groups are optionally substituted by one or more substituents selected from halo, nitro, $OR^3$, $C_{1-6}$ alkyl optionally substituted by one or more fluorine atoms, $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$ and $SO_2NR^{17}R^{18}$; wherein m is an integer of 1–3; R1, R2 and R3 independently represent H, $C_{1-10}$ alkyl optionally substituted by one or more fluorine atoms, $C_{7-9}$ alkylphenyl or phenyl, which latter group is optionally substituted by hydroxy; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently represent H, $C_{1-6}$ alkyl optionally substituted by one or more fluorine atoms, or phenyl; and X is $(CH_2)_nO$, $(CH_2)_nS$ or $C_2$ alkylene, wherein n represents 1 or 2;

in which any alkyl group present may be interrupted by one or more oxygen atoms;

provided that when X represents $CH_2CH_2$, $Ar^1$ may not represent phenyl or phenyl substituted with one or more substituents $OR^1$ in which $R^1$ represents $C_{1-10}$ alkyl.

8. A compound of formula XII,

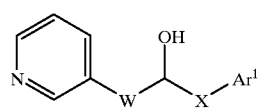

wherein W represents CH=CH or C≡C, $Ar^1$ is indanyl, naphthyl or phenyl, which latter two groups may be substituted by one or more substituents selected from the group consisting of chloro, fluoro, $OR^1$, $O(CH_2)_mCONR^{20}R^{21}$, $C(O)R^2$, $C_{1-6}$ alkyl optionally substituted by one or more fluorine atoms, pyridyl, thiazinyl, phenyl and $C_{7-9}$ alkylphenyl which latter two groups are optionally substituted by one or more substituents selected from halo, nitro, $OR^3$, $C_{1-6}$ alkyl optionally substituted by one or more fluorine atoms, $C(O)R^4$, $C(O)OR^5$, $C(O)N(R^6)R^7$, CN, $CH_2OR^{14}$, $CH_2NR^{15}R^{16}$, $N(R^8)R^9$, $N(R^{10})SO_2R^{11}$, $N(R^{12})C(O)R^{13}$, $OC(O)R^{19}$ and $SO_2NR^{17}R^{18}$, wherein m is an integer of 1–3; R1, R2 and R3 independently represent H, $C_{1-10}$ alkyl optionally substituted by one or more fluorine atoms, $C_{7-9}$ alkylphenyl or phenyl, which latter group is optionally substituted by hydroxy; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ independently represent H, $C_{1-6}$ alkyl optionally substituted by one or more fluorine atoms, or phenyl; and X is $(CH_2)_nO$, $(CH_2)_nS$ or $C_2$ alkylene, wherein n represents 1 or 2;

in which any alkyl group present may be interrupted by one or more oxygen atoms;

provided that when X represents $CH_2CH_2$, $Ar^1$ may not represent phenyl or phenyl substituted with one or more substituents $OR^1$ in which $R^1$ represents $C_{1-10}$ alkyl.

9. A compound of formula I

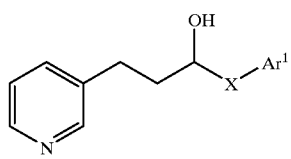

wherein:

X represents $(CH_2)_nO$, $(CH_2)_nS$ or $C_2$ alkylene;

n represents 1 or 2;

$Ar^1$ represents optionally substituted naphthyl or phenyl further including a substituent selected from amino, $O(CH_2)_mCO(O)R^{22}$ and $CH(OH)R^2$ or $Ar^1$ represents naphthyl or phenyl substituted with at least one group including phenyl or $C_{7-9}$ alkylphenyl further including a substituent selected from $CH(OH)R^4$ and $CH_2Hal$, wherein $R^{22}$ represents $C_{1-6}$ alkyl, Hal represents halogen;

m represents an integer 1 to 3;

$R^2$ represents H, $C_{1-10}$ alkyl optionally substituted by one or more fluorine atoms, $C_{7-9}$ alkylphenyl or phenyl, which latter group is optionally substituted by hydroxy;

$R^4$ represent $C_{1-6}$ alkyl optionally substituted by one or more fluorine atoms, or phenyl;

in which any alkyl group present may be interrupted by one or more oxygen atoms;

provided that when X represents $CH_2CH_2$, $Ar^1$ may not represent phenyl or phenyl substituted with one or more substituents $OR^1$, in which $R^1$ represents $C_{1-10}$ alkyl;

or a pharmaceutically acceptable derivative thereof.

10. A pharmaceutical formulation including a compound of formula I as defined in claim 2, or a pharmaceutically acceptable derivative thereof, in admixture with a pharmaceutically acceptable adjuvant, diluent or carrier.

11. A method of treatment of a reversible obstructive airways disease which comprises administering a therapeutically effective amount of a compound of formula I as defined in claim 2 or a pharmaceutically acceptable derivative thereof to a person suffering from, or susceptible to, such a disease.

12. A method as claimed in claim 11, wherein the disease is asthma.

13. 4-(3-pyridyl)-1,2-butanediol.

14. (2R) 4-(3-pyridyl)-1,2-butanediol.

* * * * *